United States Patent
Kreft et al.

(10) Patent No.: US 7,166,622 B2
(45) Date of Patent: Jan. 23, 2007

(54) SUBSTITUTED PHENYLSULFONAMIDE INHIBITORS OF BETA AMYLOID PRODUCTION

(75) Inventors: Anthony Frank Kreft, Langhorne, PA (US); Derek Cecil Cole, New City, NY (US); Kevin Roger Woller, Ayer, MA (US); Joseph Raymond Stock, Monroe, NY (US); Kristina Martha Kutterer, Westwood, NJ (US); Dennis Martin Kubrak, Philadelphia, PA (US); Charles William Mann, North Wales, PA (US); William Jay Moore, Collegeville, PA (US); David Scott Casebier, Carlisle, MA (US)

(73) Assignees: Wyeth, Madison, NJ (US); ArQule, Inc., Woburn, MA (US)

( * ) Notice: Subject to any disclaimer, the term of this patent is extended or adjusted under 35 U.S.C. 154(b) by 312 days.

(21) Appl. No.: 10/457,641

(22) Filed: Jun. 9, 2003

(65) Prior Publication Data

US 2004/0006050 A1    Jan. 8, 2004

Related U.S. Application Data

(60) Provisional application No. 60/387,690, filed on Jun. 11, 2002.

(51) Int. Cl.
| | |
|---|---|
| C07C 311/17 | (2006.01) |
| C07D 209/14 | (2006.01) |
| C07D 271/12 | (2006.01) |
| C07D 307/52 | (2006.01) |
| C07D 317/08 | (2006.01) |
| A61K 31/18 | (2006.01) |
| A61K 31/34 | (2006.01) |
| A61K 31/357 | (2006.01) |
| A61K 31/4245 | (2006.01) |

(52) U.S. Cl. .............. 514/361; 514/364; 514/415; 514/452; 514/459; 514/602; 514/604; 548/125; 548/506; 549/430; 549/495; 564/84; 564/90; 564/92; 564/93

(58) Field of Classification Search ......... 548/125, 548/506; 549/495, 430; 564/84, 90, 92, 564/93; 514/361, 459, 602, 604, 364, 415, 514/452
See application file for complete search history.

(56) References Cited

U.S. PATENT DOCUMENTS

| 4,070,176 A | 1/1978 | Oshio et al. |
| 4,113,463 A * | 9/1978 | Oshio et al. ........ 504/182 |
| 5,571,821 A | 11/1996 | Chan et al. |
| 5,591,761 A | 1/1997 | Chan et al. |
| 5,594,021 A | 1/1997 | Chan et al. |
| 5,852,007 A | 12/1998 | Chatterjee |
| 5,962,490 A | 10/1999 | Chan et al. |
| 5,977,117 A | 11/1999 | Chan et al. |
| 6,030,991 A | 2/2000 | Chan et al. |
| 6,248,775 B1 | 6/2001 | Vazquez et al. |
| 6,265,428 B1 | 7/2001 | Chan et al. |
| 6,331,637 B1 | 12/2001 | Chan et al. |
| 6,342,610 B1 | 1/2002 | Chan et al. |
| 6,376,523 B1 | 4/2002 | Chan et al. |
| 6,541,498 B1 | 4/2003 | Chan et al. |
| 6,610,734 B1 | 8/2003 | Kreft et al. |
| 2003/0013892 A1 | 1/2003 | Resnick et al. |
| 2004/0097572 A1 | 5/2004 | Smith et al. |
| 2005/0038099 A1 | 2/2005 | Tung et al. |
| 2005/0245573 A1 | 11/2005 | Neitzel et al. |
| 2006/0063799 A1 | 3/2006 | Gilligan |

FOREIGN PATENT DOCUMENTS

| DE | 838 004 | 5/1952 |
| DE | 25 44 859 | 4/1976 |
| EP | 0 081 425 B1 | 6/1983 |
| EP | 0 611 756 A2 | 8/1994 |
| EP | 1 088 821 A1 | 4/2001 |
| WO | WO-00/50391 A1 | 8/2000 |
| WO | WO-01/23379 A1 | 4/2001 |
| WO | 2005/090296 A2 | 9/2005 |

OTHER PUBLICATIONS

Ito et al., Chemical Abstracts, 120:270114, 1994.*

(Continued)

Primary Examiner—Fiona T. Powers
(74) Attorney, Agent, or Firm—Howson & Howson LLP; Rebecca R. Barrett; Yang Xu

(57) ABSTRACT

Compounds of Formula I,

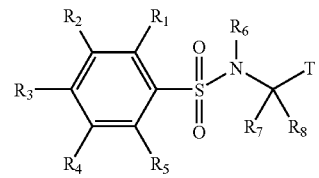

wherein $R_1$–$R_8$ are defined herein are provided, together with pharmaceutically acceptable salts, hydrates, metabolites, and/or prodrugs thereof. Uses of these compounds for inhibiting beta amyloid production and for the prevention and treatment of Alzheimer's Disease and Down's syndrome are described.

17 Claims, No Drawings

OTHER PUBLICATIONS

Li et al., "The Amyloid Precursor Protein of Alzheimer Disease in Human Brain and Blood", J. Leukocyte Biol., 66: 567 (Oct. 1999).

Näslund et al., "Correlation Between Elevated Levels of Amyloid β-Peptide in the Brain and Cognitive Decline", J. Am. Med. Assoc., 283(12): 1571 (Mar. 22/29, 2000).

Small et al., "Alzheimer's Disease and the Amyloid β Protein: What Is the Role of Amyloid?", J. Neurochem., 73(2):443 (Aug. 1999).

Dodart et al., "The β-Amyloid Precursor Protein and its Derivatives: From Biology to Learning and Memory Processes", Rev. in the Neurosci., 11(2-3):75-93 (2000).

Wolfe, "Secretase Targets for Alzheimer's Disease: Identification and Therapeutic Potential", J. Med. Chem., 44(13): 2039 (Jun. 21, 2001).

Goate, "Monogenetic Determinants of Alzheimer's Disease: *APP* Mutations", Cell. Mol. Life Sci., 54:897-901 (Sep. 1998).

Sabbagh et al., "β-Amyloid and Treatment Opportunities for Alzheimer's Disease", Alzheimer's Dis. Rev., 3:1-19 (1997).

Skovronsky et al., "β-Secretase Revealed: Starting Gate for Race to Novel Therapies for Alzheimer's Disease", Trends Pharmacol. Sci., 21:161-163 (2000).

Sinha et al., "Purification and Cloning of Amyloid Precursor Protein β-Secretase from Human Brain", Nature, 402:537 (Dec. 2, 1999).

Ghosh et al., "Design of Potent Inhibitors for Human Brain Memapsin 2 (β-Secretase)", J. Am. Chem. Soc., 122:3522-3523 (2000).

Esler et al., "Transition-State Analogue Inhibitors of γ-Secretase Bind Directly to Presenilin-1", Nature Cell Biol., 2:428 (Jul. 2000).

Li et al., "Photoactivated γ-Secretase Inhibitors Directed to the Active Site Covalently Label Presenilin 1", Nature, 405: 689 (Jun. 8, 2000).

Olson et al., "Chapter 4. Secretase Inhibitors as Therapeutics for Alzheimer's Disease", Ann. Reports in Med. Chem., 35:31 (2000).

Dovey et al., "Functional Gamma-Secretase Inhibitors Reduce Beta-Amyloid Peptide Levels in Brain", J. Neurochem., 76:173-181 (Jan. 2001).

Augelli-Szafran et al., "Chapter 3. β-Amyloid as a Target for Alzheimer's Disease Therapy", Ann. Reports in Med. Chem., 34:21 (1999).

Moore et al., "Inhibition of β-Amyloid Formation as a Therapeutic Strategy", Exp. Opin. Ther. Patents, 9(2):135-146 (1999).

Varghese et al., "Chapter 2. Alzheimer's Disease: Recent Advances on the Amyloid Hypothesis", Ann. Reports Med. Chem., 32:11 (1997).

Larner et al., "Alzheimer's Disease: Towards Therapeutic Manipulation of the Amyloid Precursor Protein and Amyloid β-Peptides", Exp. Opin. Ther. Patents, 7(10): 1115-1127 (1997).

Rishton et al., "Fenchylamine Sulfonamide Inhibitors of Amyloid βPeptide Production by the γ-Secretase Proteolytic Pathway: Potential Small-Molecule Therapeutic Agents for the Treatment of Alzheimer's Disease", J. Med. Chem., 43:2297 (Jun. 15, 2000).

Hertler et al., "Free-Radical Chain Isomerization of N-Vinylsulfonamides", J. Org. Chem., 39(22):3219 (1974).

Cho et al., "Catalytic Enantioselective Reactions. Part 12. Enantioselective Addition of Diethylzinc to Aldehydes Catalyzed by Zinc Complexes Modified with Chiral β-Sulfonamidoalcohols", Syn. Commun., 29(3):521-531 (1999).

Ito et al., "Enantioselective Addition of Diethylzinc to Aldehydes in the Presence of Chiral Titanium Reagent Modified with N-Sulfonylated Amino Alcohol", Synlett., 7:573-574 (1992).

Itsuno et al., "Enantioselective Synthesis of Optically Active Homoallylamines by Nucleophilic Addition of Chirally Modified Allylboranes to N-silylamines", J. Chem. Soc. Perkin Trans. 1:2011-2016 (1999).

Defauw et al., "Synthesis and Protein Kinase C Inhibitory Activities of Acyclic Balanol Analogs that are Highly Selective for Protein Kinase C Over Protein Kinase A", J. Med. Chem., 39:5215-5227 (Dec. 1996).

Findeis et al., "Modified Peptide Inhibitors of Amyloid-Beta-Polymerization", Am. Chem. Soc. Biochem. 38(21): 6791-6800 (May 25, 1999).

Abstract of Japanese Patent No. JP-5-148233 (Jun., 15 1993).

Abstract of Japanese Patent No. JP-11-343279 (Dec. 14, 1999).

Abstract of European Patent No. 081 425 (Jun., 15 1983).

Rishton et al., "Computational Approaches to the Prediction of Blood-Brain Barrier Permeability: A Comparative Analysis of Central Nervous System Drugs Versus Secretase Inhibitors for Alzheimer's Disease", Curr. Opinion. Drug Discovery & Development, 9(3): 303 (May, 2006).

\* cited by examiner

SUBSTITUTED PHENYLSULFONAMIDE INHIBITORS OF BETA AMYLOID PRODUCTION

CROSS-REFERENCE TO RELATED APPLICATIONS

This application claims the benefit of U.S. patent application Ser. No. 60/387,690, filed Jun. 11, 2002, which is incorporated by reference herein.

BACKGROUND OF THE INVENTION

This invention relates to small molecular compounds which inhibit beta amyloid production and have utility in the treatment of Alzheimer's disease.

Alzheimer's Disease (AD) is the most common form of dementia (loss of memory) in the elderly. The main pathological lesions of AD found in the brain consist of extracellular deposits of beta amyloid protein in the form of plaques and angiopathy and intracellular neurofibrillary tangles of aggregated hyperphosphorylated tau protein. Recent evidence has revealed that elevated beta amyloid levels in the brain not only precede tau pathology but also correlate with cognitive decline. Further suggesting a causative role for beta amyloid in AD, recent studies have shown that aggregated beta amyloid is toxic to neurons in cell culture and has a detrimental effect on memory. This suggests that reducing beta amyloid levels is a viable therapeutic strategy for the treatment of AD.

Beta amyloid protein is composed mainly of 39 to 42 amino acid peptides and is produced from a larger precursor protein called amyloid precursor protein (APP) by the sequential action of the proteases beta and gamma secretase. Although rare, cases of early onset AD have been attributed to genetic mutations in APP that lead to an overproduction of either total beta amyloid protein or its more aggregation-prone 42 amino acid isoform. Furthermore, people with Down's Syndrome possess an extra chromosome that contains the gene that encodes APP and thus have elevated beta amyloid levels and invariably develop AD later in life.

There continues to be a need for compositions useful in inhibiting beta amyloid production and in the prevention and treatment of Alzheimer's Disease.

SUMMARY OF THE INVENTION

In one aspect, a method of lowering beta amyloid levels is provided which includes delivering to a patient a phenylsulfonamide compound and monitoring the beta amyloid levels in the patient.

In another aspect, a method of lowering beta amyloid levels is provided which includes delivering to a patient a compound of formula I:

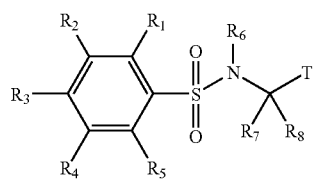

In a further aspect, a method of preventing or treating Alzheimer's disease is provided which includes delivering to a patient, a compound of formula I:

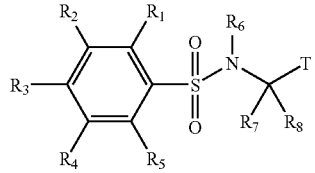

In yet another aspect, a compound of formula Ia is provided, wherein formula Ia is:

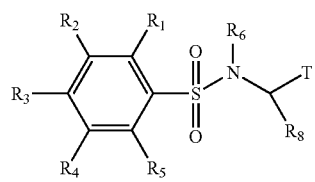

In a further aspect, a compound of formula Ib is provided, wherein formula Ib is:

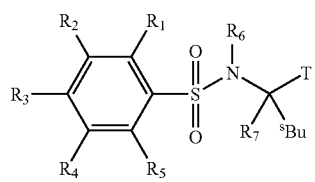

Other aspects and advantages of the present invention are described further in the following detailed description of the preferred embodiments thereof.

DETAILED DESCRIPTION OF THE INVENTION

The present invention provides methods of monitoring beta amyloid production in patients at risk for, or suffering from, AD and other diseases resulting from elevated levels of beta amyloid protein in the brain.

The present invention also provides methods of lowering beta amyloid levels which includes delivering to a patient a pharmaceutically acceptable amount of a compound of the invention and monitoring the levels of beta-amyloid in the patient.

By the term "patient" as used herein is meant to describe a mammal which has been diagnosed as having or is at risk of having one or more of the conditions for which modulation of beta amyloid levels is desirable. Preferably, the patient is a human, domestic animal, including canines and felines, or livestock and more preferably is a human. Thus, the compounds are useful for treatment and/or prevention of a number of human and veterinary conditions.

By the term "lowering beta amyloid levels" as used herein is meant to describe decreasing or inhibiting beta amyloid production in a patient. A variety of conditions can be treated by lowering beta amyloid production in a patient and include Alzheimer's Disease, dementia, Down's Syndrome, and mild cognitive impairment, among others.

As used herein, the term "prevention" encompasses precluding the onset of symptoms in a patient who has been identified with or is at risk for a condition resulting from elevated levels of beta amyloid protein in the brain. The patient may not have been diagnosed with the same or have not yet presented any symptoms thereof.

1. Compositions of the Invention

In one embodiment, the present invention provides compounds of formula I:

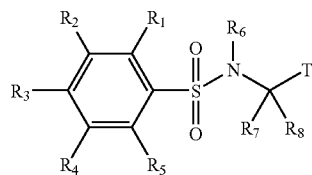

I wherein:

$R_1$ is selected from the group consisting of H, halogen, and O;

$R_2$ is selected from the group consisting of H, halogen, and N=N;

$R_3$ is selected from the group consisting of H and halogen;

$R_4$ is selected from the group consisting of H, halogen, amino, and N=N;

$R_5$ is selected from the group consisting of H, halogen, methoxy, methyl, and O;

or $R_1$ and $R_2$; $R_2$ and $R_3$; $R_4$ and $R_5$; or $R_3$ and $R_4$ are fused to form a carbon-based, naphthalene ring with the benzene ring;

$R_6$ is selected from the group consisting of H, lower alkyl, lower alkenyl, 3-phenyl-2-propyn-1-yl, benzyl, substituted benzyl, $CH_2$ cycloalkyl, $CH_2$-2-furan, $(CH_2)_2SCH_3$, and $(CH_2)_2NHBOC$;

$R_7$ is selected from the group consisting of H, lower alkyl, and cycloalkyl;

$R_8$ is selected from the group consisting of lower alkyl, substituted alkyl, cycloalkyl, phenyl, substituted phenyl, benzyl, substituted benzyl, $CH_2$ cycloalkyl, $CH_2$-3-indole, CH(lower alkyl)-2-furan, CH(lower alkyl)-4-methoxyphenyl, CH(lower alkyl) phenyl, and CH(OH)-4-$SCH_3$-phenyl;

or $R_7$ and $R_8$ are fused to form a saturated carbon-based ring;

T is

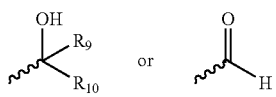

$R_9$ and $R_{10}$ are H; or $R_9$ is H and $R_{10}$ is selected from the group consisting of lower alkyl, $CF_3$, lower alkenyl, methyl-substituted alkenyl, lower alkynyl, cycloalkyl, substituted phenyl, 1-naphthyl, and $CH_2CH_2$-1,3-dioxolane; or $R_9$ and $R_{10}$ are independently selected from the group consisting of lower alkyl, lower alkenyl, phenyl, 4-substituted-phenyl, and 1-naphthyl;

wherein:

(i) when $R_5$ is a methoxy; $R_2$ is halogen and $R_1$, $R_3$, and $R_4$ are H;

(ii) when $R_5$ is a methyl; $R_1$ is halogen and $R_2$, $R_3$, and $R_4$ are H;

(iii) when $R_4$ is an amino; $R_3$ is halogen and $R_1$, $R_2$, and $R_5$ are H;

(iv) when $R_2$ is N=N and $R_1$ is O; $R_2$ is bound to $R_1$ to form a heterocyclic ring;

(v) when $R_4$ is N=N and $R_5$ is O; $R_4$ is bound to $R_5$ to form a heterocyclic ring; and (vi) at least one of $R_1$, $R_2$, $R_3$, $R_4$, and $R_5$ is halogen unless $R_1$ and $R_2$; $R_2$ and $R_3$; $R_4$ and $R_5$; or $R_3$ and $R_4$ are fused to form a carbon-based, naphthalene ring with the benzene ring;

or a pharmaceutically acceptable salt, metabolite, hydrate, or prodrug thereof.

In another embodiment, the compound is of formula Ia:

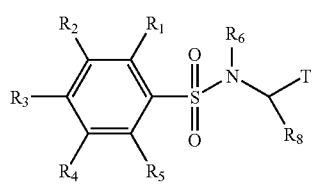

Ia wherein:

$R_1$ is selected from the group consisting of H, halogen, and O;

$R_2$ is selected from the group consisting of H, halogen, and N=N;

$R_3$ is selected from the group consisting of H and halogen;

$R_4$ is selected from the group consisting of H, halogen, amino, and N=N;

$R_5$ is selected from the group consisting of H, halogen, methoxy, methyl, and O;

$R_6$ is selected from the group consisting of H, lower alkyl, lower alkenyl, 3-phenyl-2-propyn-1-yl, benzyl, substituted benzyl, $CH_2$ cycloalkyl, $CH_2$-2-furan, $(CH_2)_2SCH_3$, and $(CH_2)_2NHBOC$;

$R_8$ is selected from the group consisting of n-propyl, iso-propyl, iso-butyl, n-butyl, t-butyl, substituted butyl, optionally substituted hexyl, optionally substituted heptyl, cycloalkyl, $CH_2$ cycloalkyl, CH(lower alkyl)-2-furan, CH(lower alkyl)-4-methoxyphenyl, CH(lower alkyl) phenyl, CH(OH)-4-$SCH_3$-phenyl, and $(CH_2)_2$—S— lower alkyl;

T is

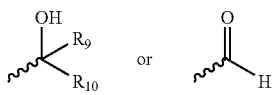

$R_9$ and $R_{10}$ are H; or $R_9$ is H and $R_{10}$ is selected from the group consisting of lower alkyl, lower alkenyl, methyl-substituted alkenyl, lower alkynyl, $CF_3$, cycloalkyl, substituted phenyl, 1-naphthyl, and $CH_2CH_2$-1,3-dioxolane; or $R_9$ and $R_{10}$ are independently selected from the group consisting of lower alkyl, lower alkenyl, phenyl, 4-substituted-phenyl, and 1-naphthyl;

wherein:
(i) when $R_5$ is a methoxy; $R_2$ is halogen and $R_1$, $R_3$, and $R_4$ are H;
(ii) when $R_5$ is a methyl; $R_1$ is halogen and $R_2$, $R_3$, and $R_4$ are H;
(iii) when $R_4$ is an amino; $R_3$ is halogen and $R_1$, $R_2$, and $R_5$ are H;
(iv) when $R_2$ is N=N and $R_1$ is O; $R_2$ is bound to $R_1$ to form a heterocyclic ring;
(v) when $R_4$ is N=N and $R_5$ is O; $R_4$ is bound to $R_5$ to form a heterocyclic ring; and
(vi) one or more of $R_1$ to $R_5$ is a halogen;

or a pharmaceutically acceptable salt, metabolite, hydrate, or prodrug thereof.

In a further embodiment, the compound is of formula I:

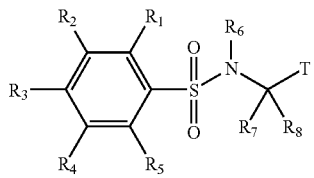

wherein:
$R_1$ is selected from the group consisting of H, halogen, and O;
$R_2$ is selected from the group consisting of H, halogen, and N=N;
$R_3$ is selected from the group consisting of H and halogen;
$R_4$ is selected from the group consisting of H, halogen, amino, and N=N;
$R_5$ is selected from the group consisting of H, halogen, methoxy, methyl, and O; or
$R_1$ and $R_2$ or $R_4$ and $R_5$ are fused to form a carbon-based, unsaturated ring;
$R_6$ is selected from the group consisting of H, lower alkyl, lower alkenyl, 3-phenyl-2-propyn-1-yl, benzyl, substituted benzyl, $CH_2$ cycloalkyl, $CH_2$-2-furan, $(CH_2)_2SCH_3$, and $(CH_2)_2NHBOC$;
$R_7$ is selected from the group consisting of H, lower alkyl, and cycloalkyl;
$R_8$ is selected from the group consisting of benzyl and substituted benzyl;
T is

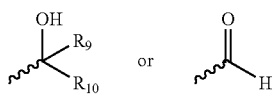

$R_9$ and $R_{10}$ are H; or
$R_9$ is H and $R_{10}$ is selected from the group consisting of lower alkyl, lower alkenyl, methyl-substituted alkenyl, $CF_3$, lower alkynyl, cycloalkyl, substituted phenyl, 1-naphthyl, and $CH_2CH_2$-1,3-dioxolane; or
$R_9$ and $R_{10}$ are independently selected from the group consisting of lower alkyl, lower alkenyl, phenyl, 4-substituted-phenyl, and 1-naphthyl;
wherein:
(i) when $R_5$ is a methoxy; $R_2$ is halogen and $R_1$, $R_3$, and $R_4$ are H;

(ii) when $R_5$ is a methyl; $R_1$ is halogen and $R_2$, $R_3$, and $R_4$ are H;
(iii) when $R_4$ is an amino; $R_3$ is halogen and $R_1$, $R_2$, and $R_5$ are H;
(iv) when $R_2$ is N=N and $R_1$ is O; $R_2$ is bound to $R_1$ to form a heterocyclic ring;
(v) when $R_4$ is N=N and $R_5$ is O; $R_4$ is bound to $R_5$ to form a heterocyclic ring; and
(vi) one or more of $R_1$ to $R_5$ is a halogen;

or a pharmaceutically acceptable salt, metabolite, hydrate, or prodrug thereof.

In yet another embodiment, the compound is of formula Ib:

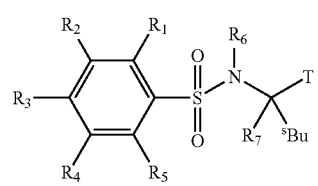

wherein:
$R_1$ is selected from the group consisting of H, halogen, and O;
$R_2$ is selected from the group consisting of H, halogen, and N=N;
$R_3$ is selected from the group consisting of H, bromine, fluorine, and iodine;
$R_4$ is selected from the group consisting of H, halogen, amino, and N=N;
$R_5$ is selected from the group consisting of H, halogen, methoxy, methyl, and O;
$R_6$ is selected from the group consisting of H, lower alkyl, lower alkenyl, 3-phenyl-2-propyn-1-yl, benzyl, substituted benzyl, $CH_2$ cycloalkyl, $CH_2$-2-furan, $(CH_2)_2SCH_3$, and $(CH_2)_2NHBOC$;
$R_7$ is selected from the group consisting of H, lower alkyl, and cycloalkyl;
T is

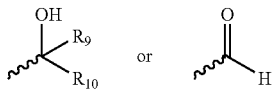

$R_9$ and $R_{10}$ are H; or
$R_9$ is H and $R_{10}$ is selected from the group consisting of lower alkyl, lower alkenyl, methyl-substituted alkenyl, $CF_3$, lower alkynyl, cycloalkyl, substituted phenyl, 1-naphthyl, and $CH_2CH_2$-1,3-dioxolane; or
$R_9$ and $R_{10}$ are independently selected from the group consisting of lower alkyl, lower alkenyl, phenyl, 4-substituted-phenyl, and 1-naphthyl;
wherein:
(i) when $R_5$ is a methoxy; $R_2$ is halogen and $R_1$, $R_3$, and $R_4$ are H;
(ii) when $R_5$ is a methyl; $R_1$ is halogen and $R_2$, $R_3$, and $R_4$ are H;
(iii) when $R_4$ is an amino; $R_3$ is halogen and $R_1$, $R_2$, and $R_5$ are H;
(iv) when $R_2$ or $R_4$ is N=N; $R_1$ or $R_5$ is O and $R_2$ or $R_4$ is bound to $R_1$ or $R_5$ to form a heterocyclic ring; and
(v) one or more of $R_1$ to $R_5$ is a halogen;

or a pharmaceutically acceptable salt, metabolite, hydrate, or prodrug thereof.

In a further embodiment, the compound is of formula I:

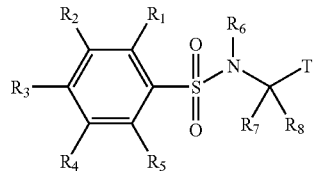

I wherein:
R$_1$ is selected from the group consisting of H, halogen, and O;
R$_2$ is selected from the group consisting of H, halogen, and N=N;
R$_3$ is selected from the group consisting of H and halogen;
R$_4$ is selected from the group consisting of H, halogen, amino, and N=N;
R$_5$ is selected from the group consisting of H, halogen, methoxy, methyl, and O;
R$_6$ is selected from the group consisting of H, lower alkyl, lower alkenyl, 3-phenyl-2-propyn-1-yl, benzyl, substituted benzyl, CH$_2$ cycloalkyl, CH$_2$-2-furan, (CH$_2$)$_2$SCH$_3$, and (CH$_2$)$_2$NHBOC;
R$_7$ is selected from the group consisting of lower alkyl and cycloalkyl;
R$_8$ is selected from the group consisting of cycloalkyl, phenyl, substituted phenyl, CH$_2$ cycloalkyl, CH(lower alkyl)-2-furan, CH(lower alkyl)-4-methoxyphenyl, CH(lower alkyl) phenyl, and CH(OH)-4-SCH$_3$-phenyl;
T is

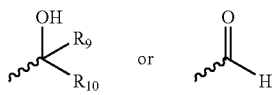

R$_9$ and R$_{10}$ are H; or
R$_9$ is H and R$_{10}$ is selected from the group consisting of lower alkyl, lower alkenyl, methyl-substituted alkenyl, lower alkynyl, CF$_3$, cycloalkyl, substituted phenyl, 1-naphthyl, and CH$_2$CH$_2$-1,3-dioxolane; or
R$_9$ and R$_{10}$ are independently selected from the group consisting of lower alkyl, lower alkenyl, phenyl, 4-substituted-phenyl, and 1-naphthyl;
wherein:
(i) when R$_5$ is a methoxy; R$_2$ is halogen and R$_1$, R$_3$, and R$_4$ are H;
(ii) when R$_5$ is a methyl; R$_1$ is halogen and R$_2$, R$_3$, and R$_4$ are H;
(iii) when R$_4$ is an amino; R$_3$ is halogen and R$_1$, R$_2$, and R$_5$ are H;
(iv) when R$_2$ is N=N and R$_1$ is O; R$_2$ is bound to R$_1$ to form a heterocyclic ring; and
(v) when R$_4$ is N=N and R$_5$ is O; R$_4$ is bound to R$_5$ to form a heterocyclic ring; and
(vi) one or more of R$_1$ to R$_5$ is a halogen;

or a pharmaceutically acceptable salt, metabolite, hydrate, or prodrug thereof.

In yet a further embodiment, the compound is of formula I:

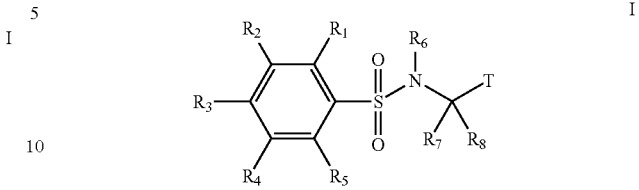

I wherein:
R$_1$ is selected from the group consisting of H, halogen, and O;
R$_2$ is selected from the group consisting of H, halogen, and N=N;
R$_3$ is selected from the group consisting of H and halogen;
R$_4$ is selected from the group consisting of H, halogen, amino, and N=N;
R$_5$ is selected from the group consisting of H, halogen, methoxy, methyl, and O; or
R$_1$ and R$_2$; R$_2$ and R$_3$; R$_4$ and R$_5$; or R$_3$ and R$_4$ are fused to form a carbon-based, naphthalene ring with the benzene ring;
R$_6$ is selected from the group consisting of H, lower alkyl, lower alkenyl, 3-phenyl-2-propyn-1-yl, benzyl, substituted benzyl, CH$_2$ cycloalkyl, CH$_2$-2-furan, (CH$_2$)$_2$SCH$_3$, and (CH$_2$)$_2$NHBOC;
R$_7$ is selected from the group consisting of H, lower alkyl, and cycloalkyl;
R$_8$ is selected from the group consisting of cycloalkyl, phenyl, substituted phenyl, benzyl, substituted benzyl, CH$_2$ cycloalkyl, CH(lower alkyl)-2-furan, CH(lower alkyl)-4-methoxyphenyl, CH(lower alkyl) phenyl, and CH(OH)-4-SCH$_3$-phenyl;
or
R$_7$ and R$_8$ are fused to form a saturated carbon-based ring;
T is

wherein:
(i) when R$_5$ is a methoxy; R$_2$ is halogen and R$_1$, R$_3$, and R$_4$ are H;
(ii) when R$_5$ is a methyl; R$_1$ is halogen and R$_2$, R$_3$, and R$_4$ are H;
(iii) when R$_4$ is an amino; R$_3$ is halogen and R$_1$, R$_2$, and R$_5$ are H;
(iv) when R$_2$ is N=N and R$_1$ is O; R$_2$ is bound to R$_1$ to form a heterocyclic ring;
(v) when R$_4$ is N=N and R$_5$ is O; R$_4$ is bound to R$_5$ to form a heterocyclic ring;
(vi) when each of R$_1$, R$_2$, R$_4$, R$_5$, and R$_6$ is H, R$_3$ is halogen, and R$_7$ is H, then R$_8$ is C$_5$ to C$_8$ alkyl or R$_7$ and R$_8$ are fused to form a saturated carbon-based ring;
(vii) when each of R$_3$, R$_4$, R$_5$, R$_6$, and R$_7$ is H and R$_1$ and R$_2$ are fused to form a carbon-based naphthalene ring, then R$_8$ is selected from the group consisting of lower alkyl, cycloalkyl, phenyl, substituted phenyl, benzyl, substituted benzyl, CH$_2$ cycloalkyl, CH(lower alkyl)-

2-furan, CH(lower alkyl)-4-methoxyphenyl; CH(lower alkyl) phenyl, and CH(OH)-4-SCH$_3$-phenyl;

(viii) when each of R$_1$, R$_2$, R$_4$, R$_5$, and R$_6$ is H and R$_3$ is halogen, then R$_7$ and R$_8$ are not both CH$_3$; and (ix) at least one of R$_1$, R$_2$, R$_3$, R$_4$, and R$_5$ is halogen unless R$_1$ and R$_2$; R$_2$ and R$_3$; R$_4$ and R$_5$; or R$_3$ and R$_4$ are fused to form a carbon-based, naphthalene ring with the benzene ring;

or a pharmaceutically acceptable salt, metabolite, hydrate, or prodrug thereof.

In another embodiment, the compound is of formula I:

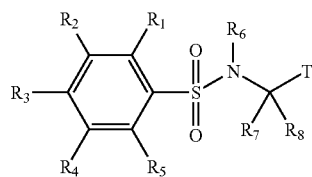

I wherein:

R$_1$ is selected from the group consisting of H, halogen, and O;

R$_2$ is selected from the group consisting of H, halogen, and N═N;

R$_3$ is selected from the group consisting of H and halogen;

R$_4$ is selected from the group consisting of H, halogen, amino, and N═N;

R$_5$ is selected from the group consisting of H, halogen, methoxy, methyl, and O;

or

R$_1$ and R$_2$; R$_2$ and R$_3$; R$_4$ and R$_5$; or R$_3$ and R$_4$ are fused to form a carbon-based, naphthalene ring with the benzene ring;

R$_6$ is selected from the group consisting of lower alkyl, lower alkenyl, 3-phenyl-2-propyn-1-yl, benzyl, substituted benzyl, CH$_2$ cycloalkyl, CH$_2$-2-furan, (CH$_2$)$_2$SCH$_3$, and (CH$_2$)$_2$NHBOC;

R$_7$ and R$_8$ are fused to form a saturated carbon-based ring;

T is

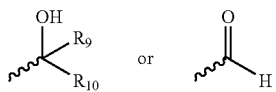

R$_9$ and R$_{10}$ are H; or

R$_9$ is H and R$_{10}$ is selected from the group consisting of lower alkyl, lower alkenyl, methyl-substituted alkenyl, CF$_3$, lower alkynyl, cycloalkyl, substituted phenyl, 1-naphthyl, and CH$_2$CH$_2$-1,3-dioxolane; or R$_9$ and R$_{10}$ are independently selected from the group consisting of lower alkyl, lower alkenyl, phenyl, 4-substituted-phenyl, and 1-naphthyl;

wherein:

(i) when R$_5$ is a methoxy; R$_2$ is halogen and R$_1$, R$_3$, and R$_4$ are H;

(ii) when R$_5$ is a methyl; R$_1$ is halogen and R$_2$, R$_3$, and R$_4$ are H;

(iii) when R$_4$ is an amino; R$_3$ is halogen and R$_1$, R$_2$, and R$_5$ are H;

(iv) when R$_2$ is N═N and R$_1$ is O; R$_2$ is bound to R$_1$ to form a heterocyclic ring;

(v) when R$_4$ is N═N and R$_5$ is O; R$_4$ is bound to R$_5$ to form a heterocyclic ring; and (vi) at least one of R$_1$, R$_2$, R$_3$, R$_4$, and R$_5$ is halogen unless R$_1$ and R$_2$; R$_2$ and R$_3$; R$_4$ and R$_5$; or R$_3$ and R$_4$ are fused to form a carbon-based, naphthalene ring with the benzene ring;

or a pharmaceutically acceptable salt, metabolite, hydrate, or prodrug thereof

In yet a further embodiment, the compound is selected from the group consisting of 2-bromo-N-[(1S,2S)-1-(hydroxymethyl)-2-methylbutyl]benzenesulfonamide, 3-bromo-N-[(1S,2S)-1-(hydroxymethyl)-2-methylbutyl]benzenesulfonamide, 3-chloro-N-[(1S,2S)-1-(hydroxymethyl)-2-methylbutyl]benzenesulfonamide, 4-chloro-N-[(1S,2S)-1-(hydroxymethyl)-2-methylbutyl]-1,2,3-benzoxadiazole-7-sulfonamide, 2-chloro-4-fluoro-N-[(1S,2S)-1-(hydroxymethyl)-2-methylbutyl]benzenesulfonamide, 5-chloro-N-[(1S,2S)-1-(hydroxymethyl)-2-methylbutyl]-2-methoxybenzenesulfonamide, 2-chloro-N-[(1S,2S)-1-(hydroxymethyl)-2-methylbutyl]-6-methylbenzenesulfonamide, 3,5-dichloro-N-[(1S,2S)-1-(hydroxymethyl)-2-methylbutyl]benzenesulfonamide, 2,4-difluoro-N-[(1S,2S)-1-(hydroxymethyl)-2-methylbutyl]benzenesulfonamide, 4-fluoro-N-[(1S,2S)-1-(hydroxymethyl)-2-methylbutyl]benzenesulfonamide, 2-fluoro-N-[(1S,2S)-1-(hydroxymethyl)-2-methylbutyl]benzenesulfonamide, N-[(1S,2S)-1-(hydroxymethyl)-2-methylbutyl]naphthalene-1-sulfonamide, N-[(1S,2S)-1-(hydroxymethyl)-2-methylbutyl]naphthalene-2-sulfonamide, 3-amino-4-chloro-N-[(1S,2S)-1-(hydroxymethyl)-2-methylbutyl]benzenesulfonamide, N-[(1S)-1-benzyl-2-hydroxyethyl]-4-bromo benzenesulfonamide, 4-bromo-N-[(1S)-1-cyclohexyl-2-hydroxyethyl]benzenesulfonamide, 4-bromo-N-[(1R)-2-hydroxy-1-(4-hydroxyphenyl)ethyl]benzenesulfonamide, 4-bromo-N-[(1S)-1-(hydroxymethyl)-3-methylbutyl]benzenesulfonamide, 4-bromo-N-[(1S)-2-hydroxy-1-(1H-indol-2-ylmethyl)ethyl]benzenesulfonamide, 4-bromo-2,5-difluoro-N-[(1S,2S)-1-(hydroxymethyl-2-methylbutyl]benzenesulfonamide, 2,5-dibromo-N-[(1S,2S)-1-(hydroxymethyl)-2-methylbutyl]benzenesulfonamide, 3,4-dibromo-N-[(1S,2S)-1-(hydroxymethyl)-2-methylbutyl]benzenesulfonamide, 2,3-dichloro-N-[(1S,2S)-1-(hydroxymethyl)-2-methylbutyl]benzenesulfonamide, 3,4-dichloro-N-[(1S,2S)-1-(hydroxymethyl)-2-methylbutyl]benzenesulfonamide, 2,4,5-trichloro-N-[(1S,2S)-1-(hydroxymethyl)-2-methylbutyl]benzenesulfonamide, 4-bromo-2,5-difluoro-N-[(1S)-1-(hydroxymethyl)-2-methylpropyl]benzenesulfonamide, 3,4-dichloro-N-[(1S)-1-(hydroxymethyl)-2-methylpropyl]benzenesulfonamide, 2,4,6-trichloro-N-[(1S)-1-(hydroxymethyl)-2-methylpropyl]benzenesulfonamide, 3,4-dibromo-N-[(11S)-1-(hydroxymethyl)-2,2-dimethylpropyl]benzenesulfonamide, 3,4-dichloro-N-[(1S)-1-(hydroxymethyl)-2,2-dimethylpropyl]benzenesulfonamide, 2,4,5-trichloro-N-[(1S)-1-(hydroxymethyl)-2,2-dimethylpropyl]benzenesulfonamide, 2,4,6-trichloro-N-[(1 S)-1-(hydroxymethyl)-2,2-dimethylpropyl]benzenesulfonamide, 4-bromo-N-[(1R,2R)-1-(hydroxymethyl)-2-methylbutyl]benzenesulfonamide, 4-bromo-N-[(1 S)-1-(hydroxymethyl)-1,2-dimethylpropyl]benzenesulfonamide, 4-bromo-N-[-1-(hydroxymethyl)-2-phenylpropyl]benzenesulfonamide, 4-bromo-N-[(1S,2R)-1-(hydroxymethyl)-2-methylbutyl]benzenesulfonamide, 4-chloro-N-[(1S)-1-(hydroxymethyl)-1,2-dimethylpropyl]benzenesulfonamide, 4-chloro-N-[1-(hydroxymethyl)-2- phenylpropyl]benzenesulfonamide, 4-chloro-N-[(1S,2R)-1-(hydroxymethyl)-2-methylbutyl]benzenesulfonamide, N-allyl-4-chloro-N-[(1S,2S)-1-(hydroxymethyl)-2-methylbutyl]benzenesulfonamide, N-([1,1'-biphenyl]-4-ylmethyl)-4-chloro-N-[(1S,2S)-1-(hydroxymethyl)-2-methylbutyl]benzenesulfonamide, tert-butyl 2-{([(4-chlorophenyl)sulfonyl][(1S,2S)-1-(hydroxymethyl)-2-methylbutyl]amino} ethyl carbamate, 4-chloro-N-(4-chlorobenzyl)-N-[(1S,2S)-1-(hydroxymethyl)-2-methylbutyl]benzenesulfonamide, 4-chloro-N-(cyclobutylmethyl)-N-[(1S,2S)-1-(hydroxymethyl)-2-methylbutyl] benzenesulfonamide, 4-chloro-N-(3,4-dimethoxybenzyl)-N-[(1S,2S)-1-(hydroxymethyl)-2-methylbutyl]benzenesulfonamide, 4-chloro-N-(2-furylmethyl)-N-[(1S,2S)-1-(hydroxymethyl)-2-methylbutyl]benzenesulfonamide, 4-chloro-N-[(1S,2S)-1-(hydroxymethyl)-2-methylbutyl]-N-[2-(methylthio)ethyl]benzenesulfonamide, 4-chloro-N-[(1S,2S)-1-(hydroxymethyl)-2-methylbutyl]-N-(3-phenylprop-2-ynyl)benzenesulfonamide, 4-chloro-N-[(1S,2R)-1-(hydroxymethyl)-2-(4-methoxyphenyl) propyl]benzenesulfonamide, 4-chloro-N-[(1S,2R)-1-(hydroxymethyl)-2-methyloctyl]benzenesulfonamide, 4-chloro-N-[(1S,2R)-1-(hydroxymethyl)-2-phenylpropyl]benzenesulfonamide, 4-chloro-N-[(1S)-2-ethyl-1-(hydroxymethyl)butyl]benzenesulfonamide, 4-chloro-N-[(1S,2R)-2-ethyl-1-(hydroxymethyl)-4-methylpentyl]benzenesulfonamide, 4-chloro-N-[(1S,2S)-1-(hydroxymethyl)-2-methylpentyl]benzenesulfonamide, 4-chloro-N-[(1S,2S)-2-ethyl-1-(hydroxymethyl)pentyl]benzenesulfonamide, 4-chloro-N-[(1S,2R)-1-(hydroxymethyl)-4-methyl-2-propylpentyl]benzenesulfonamide, 4-chloro-N-[(1S,2R)-1-(hydroxymethyl)-2-(4-methoxyphenyl) pentyl]benzenesulfonamide, 4-chloro-N-[(1S,2R)-1-(hydroxymethyl)-2-propyloctyl]benzenesulfonamide, 4-chloro-N-[(1S,2R)-1-(hydroxymethyl)-2-phenylpentyl]benzenesulfonamide, 4-chloro-N-[(1S,2S)-1-(hydroxymethyl)-2-methylheptyl]benzenesulfonamide, 4-chloro-N-[(1S,2S)-2-ethyl-1-(hydroxymethyl)-heptyl]benzenesulfonamide, 4-chloro-N-[(1S,2R)-1-(hydroxymethyl)-2-pentyloctyl]benzenesulfonamide, 4-chloro-N-[(1S,2S)-1-(hydroxymethyl)-2-phenylpropyl]benzenesulfonamide, 4-chloro-N-[(1S,2S)-1-(hydroxymethyl)-4-methyl-2-phenylpentyl]benzenesulfonamide, 4-chloro-N-[(1S,2S)-1-(hydroxymethyl)-2-phenyloctyl]benzenesulfonamide, 4-chloro -N-[(1S,2R)-2-(2-furyl)-1-(hydroxymethyl)butyl]benzenesulfonamide, 4-chloro -N-[(1S,2R)-2-(2-furyl)-1-(hydroxymethyl)-4-methyl pentyl]benzenesulfonamide, 4-chloro-N-[(1S,2R)-2-(2-furyl)-1-(hydroxymethyl)octyl]benzenesulfonamide, 4-chloro-N-[(1S,2S)-1-(hydroxymethyl)-2,3-dimethylbutyl]benzenesulfonamide, 4-chloro-N-[(1S,2S)-1-(hydroxymethyl)-2-isopropyloctyl]benzenesulfonamide, 4-bromo-N-[(1S,2R)-1-(hydroxymethyl)-2-(4-methoxyphenyl) propyl]benzenesulfonamide, 4-bromo-N-[(1S,2R)-1-(hydroxymethyl)-2-methyloctyl] benzenesulfonamide, 4-bromo-N-[(1S,2R)-2-ethyl-1-(hydroxymethyl)-4-methylpentyl]benzenesulfonamide, 4-bromo-N-[(1S,2R)-1-(hydroxymethyl)-2-(4-methoxyphenyl) butyl]benzenesulfonamide, 4-bromo-N-[(1S,2R)-2-ethyl-1-(hydroxymethyl)octyl]benzenesulfonamide, 4-bromo-N-[(1S,2S)-1-(hydroxymethyl)-2-methylpentyl]benzenesulfonamide, 4-bromo-N-[(1S,2S)-2-ethyl-1-(hydroxymethyl) pentyl]benzenesulfonamide, 4-bromo-N-[(1S,2R)-1-(hydroxymethyl)-4-methyl-2-propylpentyl]benzenesulfonamide, 4-bromo-N-[(1S,2R)-1-(hydroxymethyl)-2-propyloctyl]benzenesulfonamide, 4-bromo-N-[(1S,2S)-1-(hydroxymethyl)-2-methylheptyl]benzenesulfonamide, 4-bromo-N-[(1S,2S)-2-ethyl-1-(hydroxymethyl) heptyl]benzenesulfonamide, 4-bromo-N-[(1S,2S)-1-(hydroxymethyl)-2-phenylpropyl]benzenesulfonamide, 4-bromo-N-[(1S,2S)-1-(hydroxymethyl)-2-phenylbutyl]benzenesulfonamide, 4-bromo-N-[(1S,2R)-2-(2-furyl)-1-(hydroxymethyl)propyl]benzenesulfonamide, 4-bromo-N-[(1S,2R)-2-(2-furyl)-1-(hydroxymethyl)butyl]benzenesulfonamide, 4-bromo-N-[(1S,2R)-2-(2-furyl)-1-(hydroxymethyl)-4-methylpentyl]benzenesulfonamide, 4-bromo-N-[(1S,2S)-1-(hydroxymethyl)-2-isopropyl-4-methylpentyl]benzenesulfonamide, 4-chloro-N-[(1S,2S)-2-ethyl-1-(hydroxymethyl) octyl]benzenesulfonamide, 4-chloro-N-[(1S,2R)-2-ethyl-1-(hydroxymethyl)octyl] benzenesulfonamide, 4-chloro-N-methyl-N-[(1S,2S)-1-(hydroxymethyl)-2-methylbutyl]benzenesulfonamide, 4-chloro-N-[(1S,2S)-1-(hydroxymethyl)-2-methylbutyl]-benzenesulfonamide, 4-chloro-N-[(1S)-1-(hydroxymethyl)-3-methylbutyl]benzenesulfonamide, 4-chloro-N-[(1R,2S)-2-hydroxy-1-methyl-2-phenylethyl]benzenesulfonamide, 4-bromo-N-[1-(hydroxymethyl)cyclopentyl]benzenesulfonamide, 4-chloro-N-[(1S)-2-cyclohexyl-1-(hydroxymethyl)ethyl]benzenesulfonamide, N-{(1S)-1-[4-(benzyloxy)benzyl]-2-hydroxyethyl}-4-chlorobenzenesulfonamide, 4-chloro-N-[(1R)-1-(hydroxymethyl)-1-methylpropyl]benzenesulfonamide, 4-bromo-N-[(1S,2S)-1-(hydroxymethyl)-2-methylbutyl]-benzenesulfonamide, 4-bromo-N-[1-(hydroxymethyl) pentyl]benzenesulfonamide, 4-bromo-N-[(1R,2S)-2-hydroxy-1-methyl-2-phenylethyl]benzenesulfonamide, 4-bromo-N-[(1S)-2-hydroxy-1-phenylethyl]benzenesulfonamide, 4-bromo-N-[(1R)-1-(hydroxymethyl)-3-methylbutyl]benzenesulfonamide, 4-chloro-N-[1-(hydroxymethyl)cyclopentyl]benzenesulfonamide, 4-bromo-N-[1-(hydroxymethyl)butyl]benzenesulfonamide, 3-chloro-N-[1-(hydroxymethyl)butyl]benzenesulfonamide, 3-chloro-N-[(1S)-2-cyclohexyl-1-(hydroxymethyl)ethyl]benzenesulfonamide, 3-chloro-N-[(1R)-1-(hydroxymethyl)-3-(methylthio)propyl]benzenesulfonamide, 3-chloro-N-[(1S)-1-(hydroxymethyl) propyl]benzene sulfonamide, 2-fluoro-N-[(1S)-1-(hydroxymethyl)-3-methylbutyl]benzenesulfonamide, 2-fluoro-N-[1-(hydroxymethyl)pentyl] benzenesulfonamide, 2-fluoro-N-[(1 S,2 S)-2-hydroxy-1-methyl-2-phenylethyl] benzenesulfonamide, 2-fluoro-N-[(1S)-2-hydroxy-1-phenylethyl]benzene sulfonamide, 2-fluoro-N-[(1R)-1-(hydroxymethyl)-3-methylbutyl]benzenesulfonamide, 2-fluoro-N-[1-(hydroxymethyl)cyclopentyl]benzenesulfonamide, N-[(1S)-2-cyclohexyl-1-(hydroxymethyl) ethyl]-2-fluorobenzenesulfonamide, 2-fluoro-N-{(1S,2S)-2-hydroxy-1-(hydroxymethyl)-2-[4-(methylthio)phenyl] ethyl}benzenesulfonamide, 2-fluoro-N-[(1S)-1-(hydroxy 1-methylethyl]benzenesulfonamide, N-[(1S)-1-benzyl-2-hydroxyethyl]-2-fluorobenzenesulfonamide, 2-fluoro-N-[(1S)-1-(hydroxymethyl)-2-methylpropyl]benzenesulfonamide, 4-bromo-N-[1-(hydroxymethyl)cyclohexyl] benzenesulfonamide, 4-bromo-N-[2-(hydroxymethyl)bicyclo[2.2.1.]hept-2-yl]benzenesulfonamide, 4-bromo-N-[1-(hydroxymethyl)-2,3-dihydro-1H-inden-1-yl] benzenesulfonamide, 4-chloro-N-[1-(hydroxymethyl)cyclohexyl]benzenesulfonamide, 4-chloro-N-[1-(hydroxymethyl)-2,3-dihydro-1H-inden-1-yl] benzenesulfonamide, 4-chloro-N-(1-cyclobutyl-2-hydroxy-1-phenylethyl)benzenesulfonamide, 4-fluoro-N-[(1S,2S)-1-(1-hydroxyethyl)-2-methylbutyl]benzenesulfonamide, N-{(1S,2S)-1-[cyclopentyl(hydroxy)methyl]-2-methylbutyl}-4-fluorobenzenesulfonamide, 4-fluoro-N-{(1S)-2-hydroxy-1-[(1S)-1-methylpropyl]octyl}benzenesulfonamide, 4-fluoro-N-{(1S)-2-hydroxy-1-[(1S)-1-methylpropyl]

heptyl}benzenesulfonamide, 4-fluoro-N-{(1S)-2-hydroxy-1-[(1S)-1-methylpropyl]hexyl}benzenesulfonamide, 4-fluoro-N{(1S,2S)-1-[hydroxy-(2-methylphenyl)methyl]-2-methylbutyl}benzenesulfonamide, 4-fluoro-N-{(1S)-2-hydroxy-3,3-dimethyl-1-[(1S)-1-methylpropyl] butyl}benzenesulfonamide, 4-fluoro-N-{(1S)-2-hydroxy-1-[(1S)-1-methylpropyl]-3-butenyl}benzenesulfonamide, 4-fluoro-N-{(1S)-2-hydroxy-1-[(1S)-1-methylpropyl]-4-pentenyl}benzenesulfonamide, 4-fluoro-N-{(1S)-2-hydroxy-1-[(1S)-1-methylpropyl]butyl}benzenesulfonamide, N-{(1S,2S)-1-[(4-chlorophenyl)(hydroxy)methyl]-2-methylbutyl}-4-fluorobenzenesulfonamide, 4-fluoro-N-{(1S)-2-hydroxy-4-methyl 1-[(1S)-1-methylpropyl]-3-pentenyl}benzenesulfonamide, 4-fluoro-N-{(1S)-2-hydroxy-3-methyl-1-[(1S)-1-methylpropyl]-3-butenyl}benzenesulfonamide, 4-fluoro-N-{(1S,2S)-1-[hydroxy(4-methoxyphenyl)methyl]-2-methylbutyl}benzenesulfonamide, N-{(1S)-4-(1,3-dioxan-2-yl)-2-hydroxy-1-[(1S)-1-methylpropyl]butyl}-4-fluorobenzenesulfonamide, 4-fluoro-N-{(1S)-2-hydroxy-1-[(1S)-1-methylpropyl]-5-hexenyl}benzenesulfonamide, 4-fluoro-N-((1S,2 S)-1-{hydroxy[4-(methylsulfanyl)phenyl]methyl}-2-methylbutyl)benzenesulfonamide, N-{(1S,2S)-1-[[4-(dimethylamino)phenyl](hydroxy)methyl]-2-methylbutyl}-4-fluorobenzenesulfonamide, 4-fluoro-N-{(1S,2S)-1-[hydroxy(1-naphthyl)methyl]-2-methylbutyl}benzenesulfonamide, 4-bromo-N-[(1S,2S)-1-(1-hydroxyethyl)-2-methylbutyl]benzenesulfonamide, 4-bromo-N-1-{(1S,2S)-1-[cyclopentyl(hydroxy)methyl]-2-methylbutyl}benzenesulfonamide, 4-bromo-N-{(1S)-2-hydroxy-1-[(1S)-1-methylpropyl]heptyl}benzenesulfonamide, 4-bromo-N-{(1S)-2-hydroxy-1-[(1S)-1-methylpropyl]hexyl}benzenesulfonamide, 4-bromo-N-{(1S)-2-hydroxy-3,3-dimethyl-1-[(1S)-1-methylpropyl]butyl}benzenesulfonamide, 4-bromo-N-{(S)-2-hydroxy-4-methyl-1-[(1S)-1-methylpropyl]pentyl}benzenesulfonamide, 4-bromo-N-{(1S)-2-hydroxy-1-[(1S)-1-methylpropyl]-3-butenyl}benzenesulfonamide, 4-bromo-N-{(1S)-2-hydroxy-1-[(1S)-1-methylpropyl]-4-pentenyl}benzenesulfonamide, 4-bromo-N-{(1S)-2-hydroxy-1-[(1S)-1-methylpropyl]butyl}benzenesulfonamide, 4-bromo-N-{(1S,2S)-1-[(4-fluorophenyl)(hydroxy)methyl]-2-methylbutyl}benzenesulfonamide, 4-bromo-N-{(1S,2S)-1-[(4-chlorophenyl)(hydroxy)methyl]-2-methylbutyl}benzenesulfonamide, 4-bromo-N-{(1S)-2-hydroxy-4-methyl-1-[(1S)-1-methylpropyl]-3-pentenyl}benzenesulfonamide, 4-bromo-N-{(1S)-2-hydroxy-3-methyl-1-[(1S)-1-methylpropyl]-3-butenyl}benzenesulfonamide, 4-bromo-N-{(11 S,2S)-1-[hydroxy(4-methoxyphenyl)methyl]-2-methylbutyl}benzenesulfonamide, 4-bromo-N-{(1S,3E)-2-hydroxy-3-methyl-1-[(1S)-1-methylpropyl]-3-pentenyl}benzenesulfonamide, 4-bromo-N-{(1S)-4-(1,3-dioxan-2-yl)-2-hydroxy-1-[(1S)-1-methylpropyl]butyl} benzenesulfonamide, 4-bromo-N-{(1S)-2-hydroxy-1-[(1S)-1-methylpropyl]-5-hexenyl}benzenesulfonamide, 4-bromo-N-{(1S)-2-hydroxy-1-[(1S)-1-methylpropyl]-3-pentynyl}benzenesulfonamide, 4-bromo-N-((1S,2 S)-1-{hydroxy-[4-(methylsulfanyl)phenyl]methyl}-2-methylbutyl) benzenesulfonamide, 4-bromo-N-{(1S,2S)-1-[[4-(dimethylamino)phenyl](hydroxy) methyl]-2-methylbutyl} benzenesulfonamide, 4-chloro-N-[(1S,2S)-1-formyl-2-methylbutyl] benzenesulfonamide, 4-chloro-N-[(1S,2S)-1-(1-hydroxyethyl)-2-methylbutyl]benzenesulfonamide, 4-chloro-N-{(1S,2S)-1-[cyclopentyl (hydroxy)methyl]-2-methylbutyl}benzenesulfonamide, 4-chloro-N-{(1S)-2-hydroxy-1-[(1S)-1-methylpropyl] octyl}benzenesulfonamide, 4-chloro-N-{(1S)-2-hydroxy-1-[(1S)-1-methylpropyl]heptyl}benzenesulfonamide, 4-chloro-N-{(1S)-2-hydroxy-1-[(1S)-1-methylpropyl] hexyl}benzenesulfonamide, 4-chloro-N-{(1S)-2-hydroxy-3-methyl-1-[(1S)-1-methylpropyl] butyl}benzenesulfonamide, 4-chloro-N-{(1S,2S)-1-[hydroxy(2-methylphenyl)methyl]-2-methylbutyl}benzenesulfonamide, 4-chloro-N-{(1S)-2-hydroxy-3,3-dimethyl-1-[(1S)-1-methylpropyl] butyl}benzenesulfonamide, 4-chloro-N-{(1S)-2-hydroxy-4-methyl-1-[(1S)-1-methylpropyl] pentyl}benzenesulfonamide, 4-chloro-N-{(1S)-2-hydroxy-1-[(1S)-1-methylpropyl]-3-butenyl}benzenesulfonamide, 4-chloro-N-{(1S)-2-hydroxy-1-[(1S)-1-methylpropyl]-4-pentenyl}benzenesulfonamide, 4-chloro-N-{(1S)-2-hydroxy-1-[(1S)-1-methylpropyl] butyl}benzenesulfonamide, 4-chloro-N-{(1S,2S)-1-[(4-chlorophenyl) (hydroxy)methyl]-2-methylbutyl}benzenesulfonamide, 4-chloro-N-{(1S,2S)-1-[hydroxy(4-methoxyphenyl) methyl]-2-methylbutyl}benzenesulfonamide, 4-chloro-N-{(1S)-4-(1,3-dioxan-2-yl)-2-hydroxy-1-[(1S)-1-methylpropyl]butyl} benzenesulfonamide, 4-chloro-N-{(1S)-2-hydroxy-1-[(1S)-1-methylpropyl]-5-hexenyl}benzenesulfonamide, 4-chloro-N-{(1S)-2-hydroxy-1-[(1S)-1-methylpropyl]-3-pentynyl}benzenesulfonamide, 4-chloro-N-((1S,2S)-1-{hydroxy[4-(methylsulfanyl) phenyl]methyl}-2-methylbutyl) benzenesulfonamide, 4-chloro-N-{(1S,2S)-1-[[4-(dimethylamino)phenyl](hydroxy)methyl]-2-methylbutyl}benzenesulfonamide, 4-chloro-N-{(1S,2S)-1-[hydroxy(1-naphthyl)methyl]-2-methylbutyl}benzenesulfonamide, 3-chloro-N-[(1S,2S)-1-(1-hydroxyethyl)-2-methylbutyl]benzenesulfonamide, 3-chloro-N-{(1S,2S)-1-[cyclopentyl(hydroxy)methyl]-2-methylbutyl}benzenesulfonamide, 3-chloro-N-{(1S)-2-hydroxy-1-[(1S)-1-methylpropyl]octyl}benzenesulfonamide, 3-chloro-N-{(1S)-2-hydroxy-1-[(1S)-1-methylpropyl] heptyl}benzenesulfonamide, 3-chloro-N-{(1S)-2-hydroxy-1-[(1S)-1-methylpropyl]hexyl}benzenesulfonamide, 3-chloro-N-{(1S)-2-hydroxy-3-methyl-1-[(1S)-1-methylpropyl]butyl}benzenesulfonamide, 3-chloro-N-{(1S)-2-hydroxy-3,3-dimethyl-1-[(1S)-1-methylpropyl] butyl}benzenesulfonamide, 3-chloro-N-{(1S)-2-hydroxy-4-methyl-1-[(1S)-1-methylpropyl] pentyl}benzenesulfonamide, 3-chloro-N-{(1 S)-2-hydroxy-1-[(1S)-1-methylpropyl]-3-butenyl}benzenesulfonamide, 3-chloro-N-{(1S)-2-hydroxy-1-[(1S)-1-methylpropyl]-4-pentenyl}benzenesulfonamide, 3-chloro-N-{(1S)-2-hydroxy-1-[(1S)-1-methylpropyl]butyl}benzenesulfonamide, 3-chloro-N-{(1S,2S)-1-[(4-chlorophenyl)(hydroxy)methyl]-2-methylbutyl}benzenesulfonamide, 3-chloro-N-{(1S)-2-hydroxy-4-methyl-1-[(1S)-1-methylpropyl]-3-pentenyl}benzenesulfonamide, 3-chloro-N-{(1S,2S)-1-[hydroxy(4-methoxyphenyl)methyl]-2-methylbutyl}benzenesulfonamide, 3-chloro-N-{(1S)-4-(1,3-dioxan-2-yl)-2-hydroxy-1-[(1S)-1-methylpropyl] butyl}benzenesulfonamide, 3-chloro-N-{(1S)-2-hydroxy-1-[(1S)-1-methylpropyl]-5-hexenyl}benzenesulfonamide, 3-chloro-N-((1S,2S)-1-{hydroxy[4-(methylsulfanyl) phenyl]methyl}-2-methylbutyl)benzenesulfonamide, N-{((S,2S)-1-[cyclopentyl(hydroxy) methyl]-2-methylbutyl}-2-fluorobenzenesulfonamide, 2-fluoro-N-{(1S)-2-hydroxy-1-[(1S)-1-methylpropyl]octyl}benzenesulfonamide, 2-fluoro-N-{(1S)-2-hydroxy-1-[(1S)-1-methylpropyl] heptyl}benzenesulfonamide, 2-fluoro-N-{(1S)-2-hydroxy-1-[(1S)-1-methylpropyl]hexyl}benzenesulfonamide, 2-fluoro-N-{(1S)-2-hydroxy-1-[(1S)1-methylpropyl]-3-butenyl}benzenesulfonamide, 2-fluoro-N-{(1S,2S)-1-[(4- fluorophenyl) (hydroxy)methyl]-2-methylbutyl}benzenesulfonamide, N-{(1S,2S)-1-[(4-chlorophenyl) (hydroxy)methyl]-2-methylbutyl}-2-fluorobenzenesulfonamide, 2-fluoro-N-{(1S,2S)-1-[hydroxy(4-methoxyphenyl)methyl]-2-methylbutyl} benzenesulfonamide, N-{(1S)-4-(1,3-dioxan-2-yl)-2-hydroxy-1-[(1S)-1-methylpropyl]butyl}-2-fluorobenzenesulfonamide, 4-bromo-N-[(1S,2 S)-1-(1-hydroxy-1-methylethyl)-2-methylbutyl]benzenesulfonamide, 4-bromo-N-{(1S)-2-hydroxy-1-[(1S)-1-methylpropyl]-2-pentylheptyl}benzenesulfonamide, 4-bromo-N-{(1S)-2-butyl-2-hydroxy-1-[(1S)-1-methylpropyl] hexyl}benzenesulfonamide, 4-bromo-N-{(1S)-2-hydroxy-2-isobutyl-4-methyl-1-[(1S)-1-methylpropyl]pentyl} benzenesulfonamide, 4-bromo-N-{(1S,2S)-1-[hydroxy (diphenyl)methyl]-2-methylbutyl}benzenesulfonamide, N-{(1S)-2-allyl-2-hydroxy 1-[(1S)-1-methylpropyl]-4-pentenyl}-4-bromo benzenesulfonamide, 4-bromo-N-{(1S)-2-ethyl-2-hydroxy-1-[(1S)-1-methylpropyl] butyl}benzenesulfonamide, N-{(1S,2S)-1-[bis(4-chlorophenyl) (hydroxy)methyl]-2-methylbutyl}-4-bromobenzenesulfonamide, 4-bromo-N-{(1S)-2-hydroxy-2-isopropenyl-3-methyl-1-[(1S)-1-methylpropyl]-3-butenyl}benzenesulfonamide, 4-bromo-N-{(1S,3E)-2-hydroxy-3-methyl-2-[(1E)-1-methyl-1-propenyl]-1-[(1S)-1-methylpropyl]-3-pentenyl}benzenesulfonamide, 4-bromo-N-{(1S)-2-(3-butenyl)-2-hydroxy-1-[(1S)-1-methylpropyl]-5-hexenyl}benzenesulfonamide, 4-bromo-N-((1S,2S)-1-{hydroxy[di(1-naphthyl)]methyl}-2-methylbutyl) benzenesulfonamide, 4-chloro-N-[(1S,2S)-1-(1-hydroxy-1-methylethyl)-2-methylbutyl]benzenesulfonamide, 4-chloro-N-{(1S)-2-hexyl-2-hydroxy-1-[(1S)-1-methylpropyl] octyl}benzenesulfonamide, N-{(1S)-2-butyl-2-hydroxy-1-[(1S)-1-methylpropyl]hexyl}-4-chlorobenzenesulfonamide, 4-chloro-N-{(1S)-2-hydroxy-2-isobutyl-4-methyl-1-[(1S)-1-methylpropyl]pentyl}benzenesulfonamide, 4-chloro-N-{(1S,2S)-1-[hydroxy(diphenyl)methyl]-2-methylbutyl}benzenesulfonamide, N-{(1S)-2-allyl-2-hydroxy-1-[(1S)-1-methylpropyl]-4-pentenyl}-4-chloro benzenesulfonamide, 4-chloro-N-{(1S)-2-ethyl-2-hydroxy-1-[(1S)-1-methylpropyl] butyl}benzenesulfonamide, 4-chloro-N-{(1S)-2-hydroxy-2-isopropenyl-3-methyl-1-[(1S)-1-methylpropyl]-3-butenyl}benzenesulfonamide, 4-chloro-N-((1S,2 S)-1-{hydroxy [bis(4-methoxyphenyl)]methyl}-2-methylbutyl)benzenesulfonamide, 4-chloro-N-{(1S,3E)-2-hydroxy-3-methyl-2-[(1E)-1-methyl-1-propenyl]-1-[(1S)-1-methylpropyl]-3-pentenyl}benzenesulfonamide, N-{(1S)-2-(3-butenyl)-2-hydroxy-1-[(1S)-1-methyl propyl]-5-hexenyl}-4-chlorobenzenesulfonamide, 4-chloro-N-((1S,2S)-1-{hydroxy[di(1-naphthyl)]methyl}-2-methylbutyl) benzenesulfonamide, 4-fluoro-N-[(1S,2S)-1-(1-hydroxy-1-methylethyl)-2-methylbutyl]benzenesulfonamide, 4-fluoro-N-{(1S)-2-hexyl-2-hydroxy-1-[(1S)-1-methylpropyl] octyl}benzenesulfonamide, 4-fluoro-N-{(1S)-2-hydroxy-1-[(1S)-1-methylpropyl]-2-pentylheptyl}benzenesulfonamide, N-{(1S)-2-butyl-2-hydroxy-1-[(1S)-1-methylpropyl]hexyl}-4-fluorobenzenesulfonamide, 4-fluoro-N-{(1S)-2-hydroxy-2-isopropyl-3-methyl-1-[(1S)-1-methylpropyl] butyl}benzenesulfonamide, 4-fluoro-N-{(1S)-2-hydroxy-2-isobutyl-4-methyl-1-[(1S)-1-methylpropyl] pentyl}benzenesulfonamide, N-{(1S)-2-allyl-2-hydroxy-1-[(1S)-1-methylpropyl]-4-pentenyl}-4-fluoro benzenesulfonamide, N-{(1S)-2-ethyl-2-hydroxy-1-[(1S)-1-methylpropyl]butyl}-4-fluorobenzenesulfonamide, 4-fluoro-N-{(1S)-2-hydroxy-2-isopropenyl-3-methyl-1-[(1S)-1-methylpropyl]-3-butenyl}benzenesulfonamide, 4-fluoro-N-((1S,2S)-1-{hydroxy[bis(4-methoxyphenyl)]methyl}-2-methylbutyl) benzenesulfonamide, 4-fluoro-N-{(1S,3E)-2-hydroxy-3-methyl-2-[(1E)-1-methyl-1-propenyl]-1-[(1S)-1-methylpropyl]-3-pentenyl}benzenesulfonamide, N-{(1S)-2-(3-butenyl)-2-hydroxy-1-[(1S)-1-methylpropyl]-5-hexenyl}-4-fluorobenzenesulfonamide, N-{(1S,2S)-1-[bis[4-(dimethylamino)phenyl](hydroxy)methyl]-2-methylbutyl}-4-fluorobenzenesulfonamide, 4-fluoro-N-((1S,2S)-1-{hydroxy[di(1-naphthyl)]methyl}-2-methylbutyl) benzenesulfonamide, 3-chloro-N-{(1S)-2-hexyl-2-hydroxy-1-[(1S)-1-methylpropyl]octyl}benzenesulfonamide, 3-chloro-N-{(1S)-2-hydroxy-1-[(1S)-1-methylpropyl]-2-pentylheptyl}benzenesulfonamide, N-{(1S)-2-butyl-2-hydroxy-1-[(1S)-1-methylpropyl]hexyl}-3-chlorobenzenesulfonamide, 3-chloro-N-{(1S)-2-hydroxy-2-isobutyl-4-methyl-1-[(1S)-1-methylpropyl] pentyl}benzenesulfonamide, 3-chloro-N-{(1S,2S)-1-[hydroxy(diphenyl)methyl]-2-methylbutyl}benzenesulfonamide, N-{(1S)-2-allyl-2-hydroxy-1-[(1S)-1-methylpropyl]-4-pentenyl}-3-chloro benzenesulfonamide, 3-chloro-N-{(1S)-2-ethyl-2-hydroxy-1-[(1S)-1-methylpropyl]butyl}benzenesulfonamide, N-{(1S,2S)-1-[bis(4-chlorophenyl)(hydroxy)methyl]-2-methylbutyl}-3-chloro benzenesulfonamide, 3-chloro-N-{(1S)-2-hydroxy-2-isopropenyl-3-methyl-1-[(18)-1-methylpropyl]-3-butenyl}benzenesulfonamide, 3-chloro-N-((1S,2S)-1-{hydroxy [bis(4-methoxyphenyl)]methyl}-2-methylbutyl) benzenesulfonamide, 3-chloro-N-{(1S,3E)-2-hydroxy-3-methyl-2-[(1 F)-1-methyl-1-propenyl]-1-[(1S)-1-methylpropyl]-3-pentenyl}benzenesulfonamide, N-{(1S)-2-(3-butenyl)-2-hydroxy-1-[(1S)-1-methylpropyl]-5-hexenyl}-3-chlorobenzenesulfonamide, 2-fluoro-N-{(1S)-2-hexyl-2-hydroxy-1-[(18)-1-methylpropyl] octyl}benzenesulfonamide, 2-fluoro-N-{(1S)-2-hydroxy-1-[(1S)-1-methylpropyl]-2-pentylheptyl}benzenesulfonamide, 2-fluoro-N-{(1S,2 S)-1-[hydroxy (diphenyl)methyl]-2-methylbutyl}benzenesulfonamide, N-{(1S)-2-allyl-2-hydroxy-1-[(1S)-1-methylpropyl]-4-pentenyl}-2-fluorobenzenesulfonamide, N-{(1S)-2-ethyl-2-hydroxy-1-[(1S)-1-methylpropyl]butyl}-2-fluorobenzenesulfonamide, N-{(1S,2S)-1-[bis(4-fluorophenyl)(hydroxy)methyl]-2-methylbutyl}-2-fluorobenzenesulfonamide, N-{(1S,2S)-1-[bis(4-chlorophenyl)(hydroxy)methyl]-2-methylbutyl}-2-fluoro benzenesulfonamide, 2-fluoro-N-{(1S)-2-hydroxy-2-isopropenyl-3-methyl-1-[(1S)-1-methylpropyl]-3-butenyl}benzenesulfonamide, 2-fluoro-N-((1S,2S)-1-{hydroxy[bis(4-methoxyphenyl)]methyl}-2-methylbutyl) benzenesulfonamide, 2-fluoro-N-{(1S,3E)-2-hydroxy-3-methyl-2-[(1E)-1-methyl-1-propenyl]-1-[(1S)-1-methylpropyl]-3-pentenyl}benzenesulfonamide, N-{(1S)-2-(3-butenyl)-2-hydroxy-1-[(1S)-1-methylpropyl]-5-hexenyl}-2-fluorobenzenesulfonamide, 4-chloro-N-[(1S)-1-cyclohexyl-2-hydroxyethyl]benzenesulfonamide, 4-chloro-N-[(1S)-2-hydroxy-1-phenylethyl]benzenesulfonamide, 4-chloro-N-[(1S)-1-(hydroxymethyl)-2-methylpropyl]benzenesulfonamide, 4-bromo-N-[(1S)-1-(hydroxymethyl)-2-methylpropyl]benzenesulfonamide, 4-iodo-N-[(1S,2S)-1-(hydroxymethyl)-2-methylbutyl]benzenesulfonamide, and 4-chloro-N-[(1S)-1-(hydroxymethyl)-2,2-dimethylpropyl] benzenesulfonamide; or a pharmaceutically acceptable salt, hydrate, metabolite, or prodrug thereof.

In another embodiment, the compound is 4-chloro-N-[(1S)-2-ethyl-1-(hydroxymethyl)butyl]benzenesulfonamide or a pharmaceutically acceptable salt, metabolite, hydrate, or prodrug thereof The compounds of the invention can contain one or more asymmetric carbon atoms and some of the compounds can contain one or more asymmetric (chiral) centers and can thus give rise to optical isomers and diastereomers. While shown without respect to stereochemistry, when the compounds can contain one or more chiral centers, preferably at least one of the chiral centers is of S-stereochemistry. Most preferably, the carbon atom to which N, T, $R_7$ and $R_8$ are attached is of S-stereochemistry. Thus, the invention includes such optical isomers and diastereomers; as well as the racemic and resolved, enantiomerically pure stereoisomers; as well as other mixtures of the R and S stereoisomers, and pharmaceutically acceptable salts, hydrates, metabolites, and prodrugs thereof.

The term "alkyl" is used herein to refer to both straight- and branched-chain saturated aliphatic hydrocarbon groups having about one to about ten carbon atoms, preferably one to eight carbon atoms and, most preferably, one to six carbon atoms. The term "lower alkyl" is used herein to refer to straight- and branched-chain saturated aliphatic hydrocarbon groups having about one to about six carbon atoms. The term "alkenyl" is used herein to refer to straight- and branched-chain alkyl groups having at least one carbon-carbon double bond and about two to about eight carbon atoms, preferably two to six carbon atoms. The term "alkynyl" is used herein to refer to straight- and branched-chain alkyl groups having at least one carbon-carbon triple bond and about two to about eight carbon atoms, preferably two to six carbon atoms.

The terms "substituted alkyl", "substituted alkenyl", and "substituted alkynyl" refer to alkyl, alkenyl, and alkynyl as just described having from one to three substituents selected from the group consisting of halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, and arylthio, which groups can be optionally substituted. These substituents can be attached to any carbon of an alkyl, alkenyl, or alkynyl group provided that the attachment constitutes a stable chemical moiety.

The term "aryl" is used herein to refer to a carbocyclic aromatic system, which can be a single ring, or multiple aromatic rings fused or linked together as such that at least one part of the fused or linked rings forms the conjugated aromatic system. The aryl groups include, but are not limited to, phenyl, naphthyl, biphenyl, anthryl, tetrahydronaphthyl, and phenanthryl.

The term "substituted aryl" refers to aryl as just defined having one or more substituents including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio. Preferably, a substituted aryl group is substituted with one to about four substituents.

The term "heterocyclic" is used herein to describe a stable 4- to 7-membered monocyclic or a stable multicyclic heterocyclic ring which is saturated, partially unsaturated, or wholly unsaturated. The heterocyclic ring has in its backbone carbon atoms and one or more heteroatoms including N, O, and S atoms. Preferably, the heterocyclic ring has about 1 to about 4 heteroatoms in the backbone of the ring. When the heterocyclic ring contains nitrogen or sulfur atoms in the backbone of the ring, the nitrogen or sulfur atoms can be oxidized. The heterocyclic ring also includes any multicyclic ring in which any of the above defined heterocyclic rings is fused to an aryl ring. The heterocyclic ring can be attached at any heteroatom or carbon atom provided the resultant structure is chemically stable.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Oxygen-containing rings include, but are not limited to, furyl, tetrahydrofuranyl, pyranyl, pyronyl, and dioxinyl rings. Nitrogen-containing rings include, without limitation, pyrrolyl, pyrazolyl, imidazolyl, triazolyl, pyridyl, piperidinyl, 2-oxopiperidinyl, pyridazinyl, pyrimidinyl, pyrazinyl, piperazinyl, azepinyl, triazinyl, pyrrolidinyl, and azepinyl rings. Sulfur-containing rings include, without limitation, thienyl and dithiolyl rings. Mixed heteroatom containing rings include, but are not limited to, oxathiolyl, oxazolyl, thiazolyl, oxadiazolyl, oxatriazolyl, dioxazolyl, oxathiazolyl, oxathiolyl, oxazinyl, oxathiazinyl, morpholinyl, thiamorpholinyl, thiamorpholinyl sulfoxide, oxepinyl, thiepinyl, and diazepinyl rings. Fused heteroatom-containing rings include, but are not limited to, benzofuranyl, benzo[b]thienyl or benzo[c]thienyl, indolyl, benazazolyl, purindinyl, pyranopyrrolyl, isoindazolyl, indoxazinyl, benzoxazolyl, anthranilyl, benzopyranyl, quinolinyl, isoquinolinyl, benzodiazonyl, naphthyridinyl, benzothienyl, pyridopyridinyl, benzoxazinyl, xanthenyl, acridinyl, and purinyl rings.

As used herein, an N-substituted piperidinyl group can be defined as a substituted heterocyclic group. Among particularly desirable substituents are N-alkyl-, N-aryl-, N-acyl-, and N-sulfonyl piperidinyl groups. One particularly suitable N-acyl-piperidinyl group is N-t-butyloxycarbonyl (BOC)-piperidine. However, other suitable substituents can be readily identified by one of skill in the art.

The term "substituted heterocyclic" is used herein to describe a heterocyclic group having one or more substituents including halogen, CN, OH, $NO_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, and arylthio. Preferably, a substituted heterocyclic group has 1 to about 4 substituents.

The term "alkoxy" is used herein to refer to the O(alkyl) group, where the point of attachment is through the oxygen-atom and the alkyl group is optionally substituted. The term "aryloxy" is used herein to refer to the O(aryl) group, where the point of attachment is through the oxygen-atom and the aryl group is optionally substituted.

The term "alkylcarbonyl" is used herein to refer to the CO(alkyl) group, where the point of attachment is through the carbon-atom of the carbonyl moiety and the alkyl group is optionally substituted.

The term "alkylcarboxy" is used herein to refer to the COO(alkyl) group, where the point of attachment is through the carbon-atom of the carboxy group and the alkyl group is optionally substituted.

The term "aminoalkyl" is used herein to refer to secondary and tertiary amines where the point of attachment is through the nitrogen-atom and the alkyl groups are optionally substituted. Preferably, the alkyl groups contain one to eight carbon atoms and can be either same or different.

The term "halogen" refers to Cl, Br, F, or I.

The term "ring" structure, e.g., when $R_3$ and $R_4$ can form a ring structure, includes a monocyclic structure, a bridged cyclo structure, and fused cyclo structures, unless the type of ring structure is otherwise specified.

The compounds of the present invention encompass tautomeric forms of the structures provided herein characterized by the bioactivity of the exemplary compounds and drawn structures. Further, the compounds of the present invention can be used in the form of salts derived from pharmaceutically or physiologically acceptable acids, bases, alkali metals and alkaline earth metals.

Physiologically acceptable acids include those derived from inorganic and organic acids. A number of inorganic acids are known in the art and include hydrochloric, hydrobromic, hydroiodic, sulfuric, nitric, and phosphoric acids, among others. Similarly, a variety of organic acids are known in the art and include, without limitation, lactic, formic, acetic, fumaric, citric, propionic, oxalic, succinic, glycolic, glucuronic, maleic, furoic, glutamic, benzoic, anthranilic, salicylic, tartaric, malonic, mallic, phenylacetic, mandelic, embonic, methanesulfonic, ethanesulfonic, panthenoic, benzenesulfonic, toluenesulfonic, stearic, sulfanilic, alginic, and galacturonic acids, among others.

Physiologically acceptable bases include those derived from inorganic and organic bases. A number of inorganic bases are known in the art and include aluminum, calcium, lithium, magnesium, potassium, sodium, and zinc hydroxide compounds, among others. A number of organic bases are known in the art and include, without limitation, N,N,-dibenzylethylenediamine, chloroprocaine, choline, diethanolamine, ethylenediamine, meglumine, and procaine, among others.

Physiologically acceptable alkali salts and alkaline earth metal salts can include, without limitation, sodium, potassium, calcium and magnesium salts in the form of esters, hydroxides, and carbamates. Other conventional "pro-drug" forms can also be utilized which, when delivered in such form, convert to the active moiety in vivo.

These salts, as well as other compounds of the invention can be in the form of esters, carbamates and other conventional "pro-drug" forms, which, when administered in such form, convert to the active moiety in vivo. In a currently preferred embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233–241, ed., John Wiley & Sons (1996).

The compounds discussed herein also encompass "metabolites" which are unique products formed by processing the compounds of formula I, Ia, or Ib by the cell or patient. Preferably, metabolites are formed in vivo.

The compounds of the present invention can be prepared in a number of ways well known to one skilled in the art. The compounds of the present invention can be prepared using the methods described below, together with synthetic methods known in the synthetic organic arts or variations of these methods by one skilled in the art. See, generally, Comprehensive Organic Synthesis, "Selectivity, Strategy & Efficiency in Modern Organic Chemistry", ed., I. Fleming, Pergamon Press, New York (1991); Comprehensive Organic Chemistry, "The Synthesis and Reactions of Organic Compounds", ed. J. F. Stoddard, Pergamon Press, New York (1979). Preferred methods include, but are not limited to, those outlined below.

In certain embodiments, it may be desirable to utilize chirally pure α-amino acids, 1,2-aminoalcohols, N-sulfonyl α-amino acids, and N-sulfonyl 1,2-aminoalcohols in the reactions described herein for the production of the phenylsulfonamides of the invention. A number of methods for producing these compounds are known in the art. Among desirable methodologies are those described in U.S. patent application Ser. No. 60/339,264, filed Dec. 11, 2001, and later filed as U.S. patent application Ser. No. 10/304,322 and International Patent Application PCT/US02/38119, both filed Nov. 26, 2002, "Process for the Synthesis of Chirally Pure α-Amino-Alcohols"; U.S. patent application Ser. No. 10/014,304, filed Dec. 11, 2001, entitled "Heterocyclic Sulfonamide Inhibitors of Beta Amyloid Production", published as US-2002-0183361-A on Dec. 5, 2002; and U.S. patent application Ser. No. 10/166,896, filed Jun. 11, 2002 and later published Jan. 16, 2003 as US-2003-0013892-A1, entitled "Production of Chirally Pure α-Amino Acids and N-Sulfonyl α-Amino Acids".

A first method of preparation for the compounds of the invention consists of reaction of a 1,2-aminoalcohol II with the appropriate sulfonyl halide in the presence of a base such as triethylamine (TEA) and in a suitable solvent to afford compounds of formula III. For compounds where $R_9$ and $R_{10}$ are hydrogen, oxidation of the N-sulfonyl primary alcohol with pyridinium chlorochromate (PCC) or under Swern conditions then affords the corresponding aldehyde IV which can be reacted with Grignard reagents to afford the secondary alcohols V as a mixture of diastereomers which can be separated by high performance liquid chromatography (HPLC) or other suitable methods (Scheme 1).

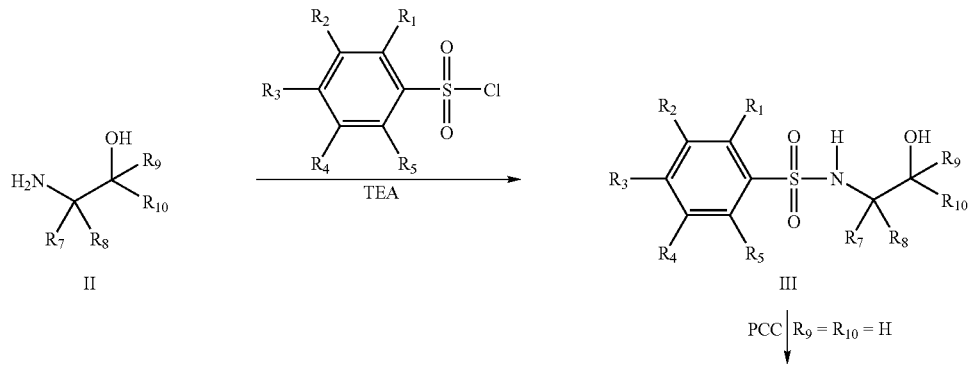

-continued

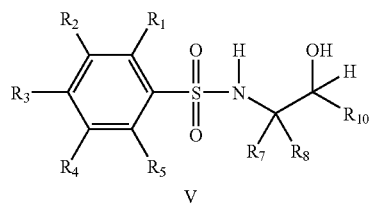 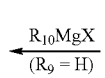 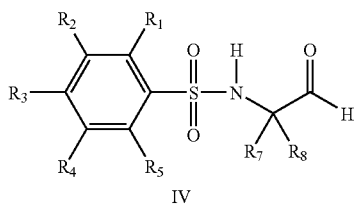

A second method of preparation involves reaction of an α-amino acid or ester IX with the appropriate sulfonyl halide in the presence of a base such as triethylamine and in a suitable solvent to afford compounds of formula X (Scheme 2). The intermediate N-sulfonyl acid X (Rx=H) can be converted to the corresponding primary alcohol VIII ($R_9$=$R_{10}$=H) utilizing standard methodology such as LiAlH$_4$ (LAH), B$_2$H$_6$ or cyanuric chloride/NaBH$_4$. The intermediate N-sulfonyl ester X (Rx=alkyl, Bn) can also be reduced to the corresponding primary alcohol VIII utilizing standard methodology such as LiAlH$_4$. Alternatively, the intermediate N-sulfonyl ester X (Rx=alkyl, Bn) can be converted to the aldehyde IV with diisobutyl aluminumhydride (DiBAL). Finally, the intermediate N-sulfonyl ester X (Rx=alkyl, Bn) can be reacted with 2 equivalents of Grignard reagent to afford the tertiary alcohols III with $R_9$=$R_{10}$. Alternatively, for tertiary alcohols III with $R_9$ not equal to $R_{10}$, the corresponding Weinreb amide (see Scheme 7) of the N-sulfonyl acid can be prepared and subsequently reacted with $R_9$MgX and $R_{10}$MgX.

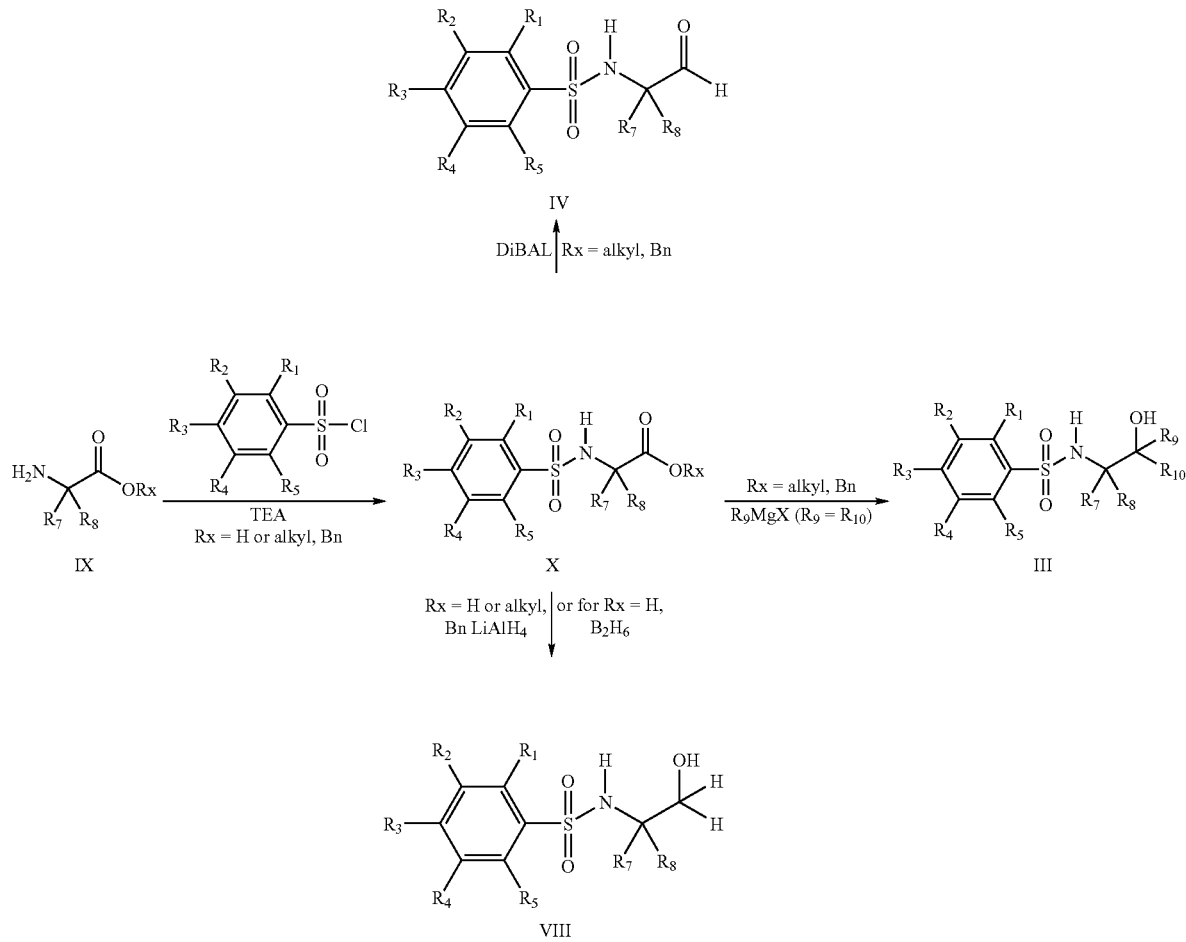

In a variation of the second method to prepare the primary alcohols, an α-amino acid or ester (or N-protected derivative thereof) VI is first converted to the corresponding primary 1,2-aminoalcohol VII (using the methodology outlined in the previous paragraph), which is subsequently, after deprotection (if necessary), reacted with the appropriate sulfonyl halide (Scheme 3) to afford compounds of formula VIII.

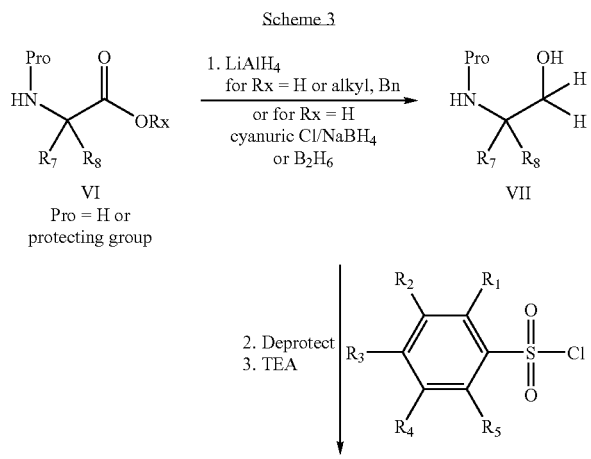

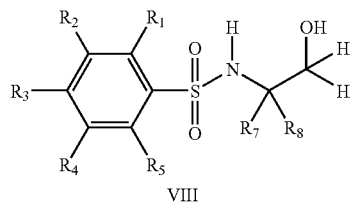

For the preparation of compounds derived from unnatural α-amino acids containing beta branching in the amino acid side chain, a method of preparation based on the work of Hruby (Tet. Lett. 38: 5135–5138 (1997)), incorporated by reference, is outlined in Scheme 4. This route entails formation of the α,β-unsaturated amide XII of the Evans chiral auxiliary from an α,β-unsaturated acid XI, followed by conjugate addition of an organocuprate, trapping of the resulting enolate anion XIII with N-bromosuccinimide (NBS), displacement of the bromide XIV with azide anion to afford XV, followed by reduction to the 1,2-aminoalcohol and subsequent sulfonylation to afford the target compound XVI.

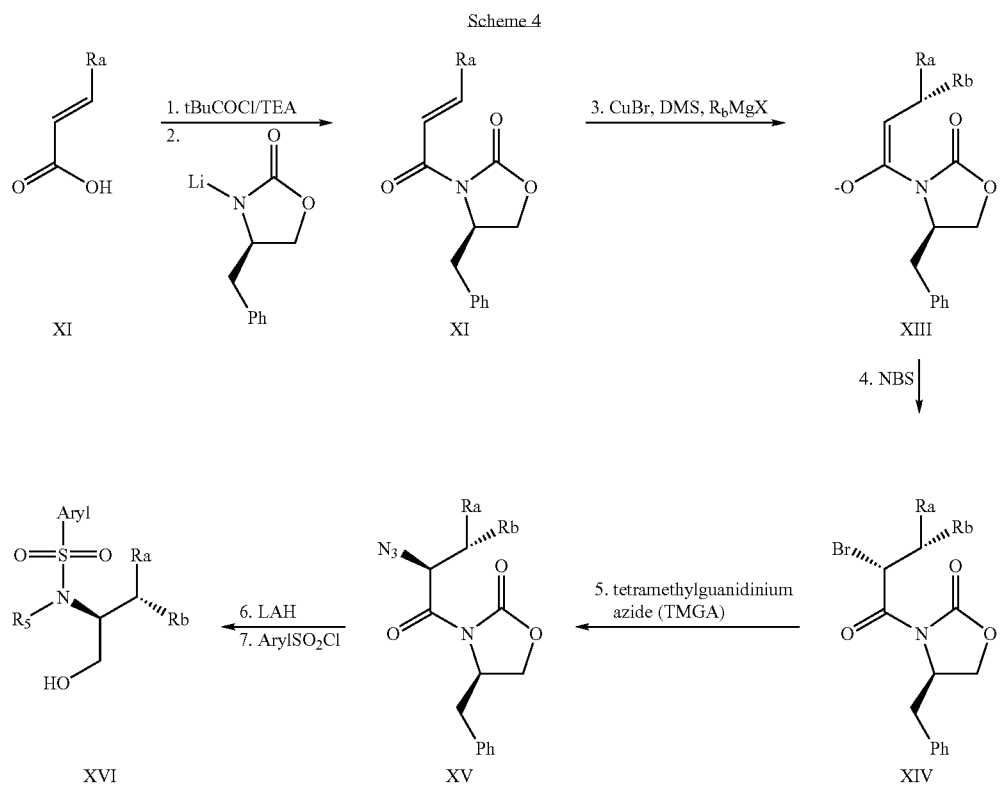

For the preparation of N-alkylated sulfonamides XVII ($R_6$ can be alkyl, substituted alkyl, allyl, substituted allyl, benzyl, or substituted benzyl), the sulfonamide ester X can be N-alkylated by either treatment with a suitable base such as sodium hydride followed by the alkylating agent $R_6X$ or by employing Mitsunobu conditions ($R_6OH/DEAD$, TPP). $LiBH_4$ reduction of the N-alkylated sulfonamide ester affords the N-alkylated sulfonamide in the primary alcohol series XVII (Scheme 5). These primary alcohols XVII can be converted to N-alkylated analogs of the secondary alcohols V or aldehyde IV series by chemistry that has been outlined above. Alternatively, the N-alkylated sulfonamide esters, or their corresponding Weinreb amides, can be treated with Grignard reagents to afford the N-alkylated analogs of the tertiary alcohols III (where $R_9$ and $R_{10}$ are non-hydrogen).

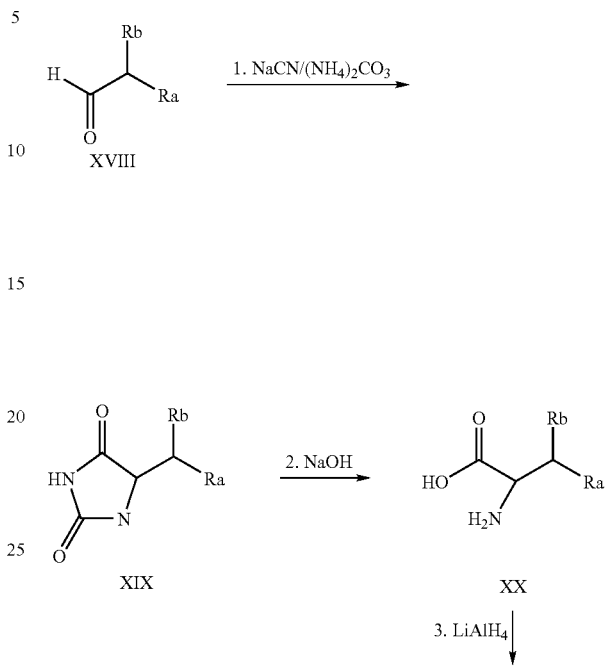

Scheme 6

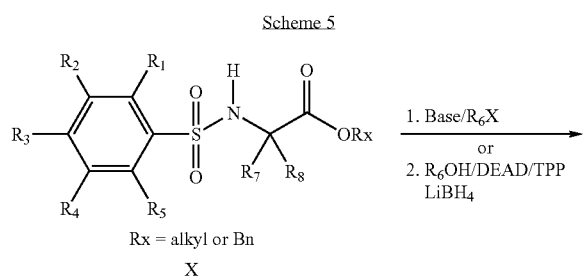

Scheme 5

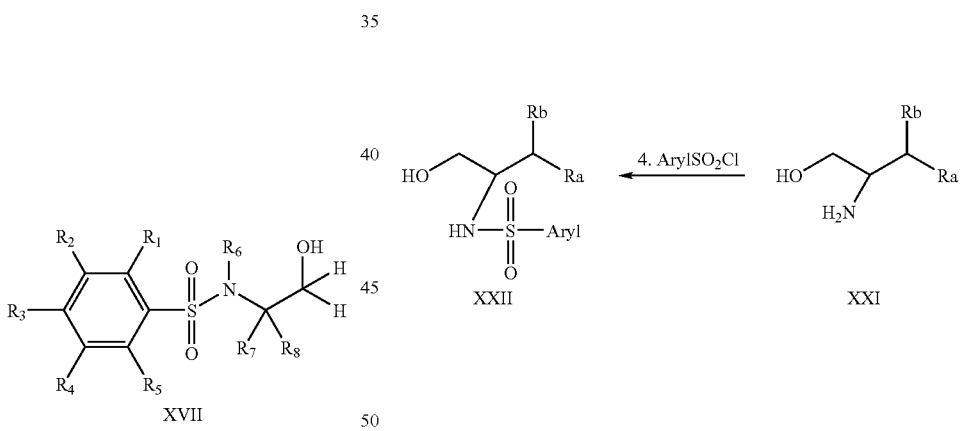

An alternate preparation of sulfonamides derived from unnatural 1,2-aminoalcohols utilizes the Bucherer modification of the Strecker α-amino acid synthesis (Scheme 6). In this route, an aldehyde XVIII is reacted with cyanide anion and ammonium carbonate to afford the hydantoin XIX, which is hydrolyzed to the α-amino acid XX. This compound is then reduced to XXI and sulfonylated to afford the desired compounds of formula XXII.

As previously noted (Scheme 1), the preparation of sulfonamides derived from 1,2-aminoalcohols in the secondary alcohol series V results in the formation of a diastereomeric mixture. An alternate method of preparation of these compounds that results in the production of a pure diastereomer is outlined in Scheme 7 for compounds derived from L-isoleucine. This method, which utilizes chemistry previously employed by Roux (Tetrahedron 50: 5345–5360 (1994)), consists of addition of Grignard reagents to the Weinreb amide XXIII (derived from the requisite α-amino acid) followed by stereospecific reduction of the ketone XXIV to afford a single diastereomeric N-protected 1,2-aminoalcohol XXV. Deprotection of this compound followed by reaction with sulfonyl chlorides affords the pure diastereomeric sulfonamide secondary alcohols of formula XXVI.

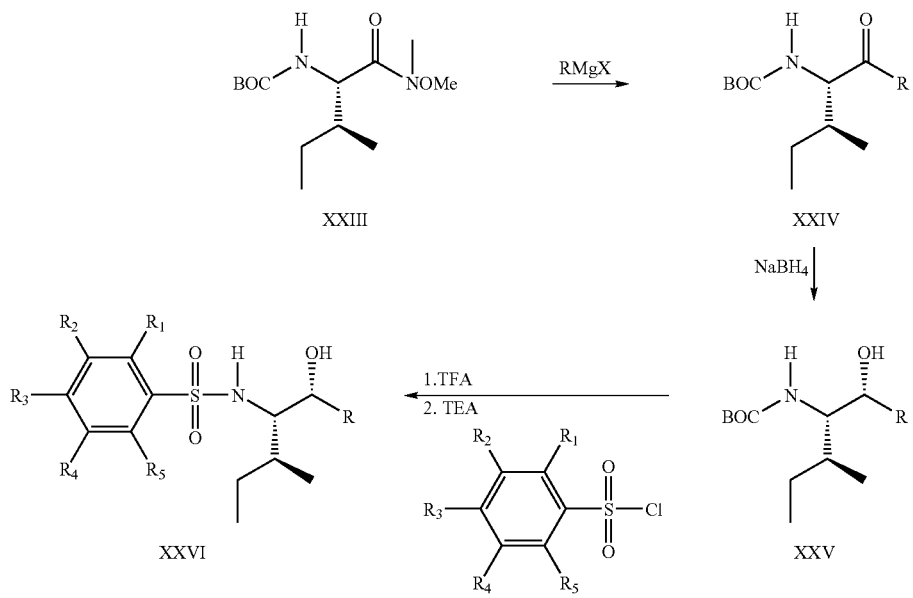

Scheme 7

Where catalysts or solvents are included in a reaction step of this invention, it is expected that other catalysts or solvents known in the art, but not mentioned herein, can be used. Those skilled in the art will readily be able to determine suitable catalysts, solvents and reaction conditions for each reaction step included in the invention.

The invention includes certain types of reactions, such as enolate trapping, hydrolysis, and reduction reactions that are generally known in the art, but previously had not been applied in the novel manner of the present invention. Variations in the specific methods of accomplishing individual steps of the invention can be apparent to those in the art. Although all of these possible variations cannot be set forth herein, such variations are contemplated to be within the scope of the present invention.

II. Formulations of the Invention

The compounds described herein can be formulated in any form suitable for the desired route of delivery using a pharmaceutically effective amount of one or more of the compounds of the invention. For example, the compositions of the invention can be delivered by a route such as oral, dermal, transdermal, intrabronchial, intranasal, intravenous, intramuscular, subcutaneous, parenteral, intraperitoneal, sublingual, intracranial, epidural, intratracheal, intranasal, vaginal, rectal, or by sustained release. Preferably, delivery is oral.

A pharmaceutically effective amount of a compound used according to the present invention can vary depending on the specific compound, mode of delivery, severity of the condition being treated, and any other active ingredients used in the formulation or the selected regimen. The dosing regimen can be adjusted to provide the optimal therapeutic response. Several divided doses can be delivered daily or a single daily dose can be delivered. The dose can however be proportionally reduced or increased as indicated by the exigencies of the therapeutic situation.

As described herein, a pharmaceutically useful amount of a compound of the invention is that amount of a compound which alleviates the symptoms of the disease, e.g., AD, or which prevents the onset of symptoms, or the onset of more severe symptoms. Generally, an individual dose (i.e., per unit, e.g., tablet) of a compound of the invention can be in the range from about 1 µg/kg to about 10 g/kg, more preferably 10 mg/kg to about 5 g/kg, and most preferably about 1 mg/kg to about 200 mg/kg. Desirably, these amounts are provided on a daily basis. However, the dosage to be used in the treatment or prevention of a specific cognitive deficit or other condition can be subjectively determined by the attending physician. The variables involved include the specific cognitive deficit and the size, age and response pattern of the patient.

The compounds of the invention can be combined with one or more pharmaceutically acceptable carriers or excipients including, without limitation, solid and liquid carriers which are compatible with the compounds of the present invention. Such carriers can include adjuvants, syrups, elixirs, diluents, binders, lubricants, surfactants, granulating agents, disintegrating agents, emollients, solubilizers, suspending agents, fillers, glidants, compression aids, encapsulating materials, emulsifiers, buffers, preservatives, thickening agents, colors, viscosity regulators, stabilizers, osmoregulators, and combinations thereof. Optionally, one or more of the compounds of the invention can be mixed with other active agents.

Adjuvants can include, without limitation, flavoring agents, sweeteners, coloring agents, preservatives, and supplemental antioxidants, which can include vitamin E, ascorbic acid, butylated hydroxytoluene (BHT) and butylated hydroxyanisole (BHA).

Elixers and syrups can be prepared from acceptable sweeteners such as sugar, saccharine or a biological sweetener, a flavoring agent, and/or solvent. In one embodiment, a syrup can contain about 10 to about 50% of a sugar carrier. In another embodiment, the elixir can contain about 20 to about 50% of an ethanol carrier.

Diluents can include materials in which the compound can be dispersed, dissolved, or incorporated. Preferably, the diluents include water, lower monovalent alcohols, monohydric alcohols, polyhydric alcohols, and low molecular weight glycols and polyols, including propylene glycol, diethylene glycol, polyethylene glycol, polypropylene glycol, glycerol, butylene glycol, 1,2,4-butanetriol, sorbitol esters, 1,2,6-hexanetriol, ethanol, isopropanol, sorbitol esters, butanediol, ethyl oleate, isopropyl myristate, ether propanol, ethoxylated ethers, propoxylated ethers, oils such as corn, peanut, fractionated coconut, arachis, sesame oils, dimethylsulfoxide (DMSO), dimethylformamide (DMF), waxes, preferably low-melting waxes, dextrin, and combinations thereof. Preferably, the diluent is water.

Binders can include, without limitation, cellulose, methylcellulose, hydroxymethylcellulose, polypropylpyrrolidone, polyvinylpyrrolidone, polyvinylpyrrolidine, gelatin, gum arabic, polyethylene glycol, starch, sugars such as sucrose, kaolin, cellulose kaolin, and lactose, among others.

Lubricants can include magnesium stearate, light anhydrous silicic acid, talc and sodium lauryl sulfate, among others.

Granulating agents can include, without limitation, silicon dioxide, microcrystalline cellulose, starch, calcium carbonate, pectin, crospovidone, and polyplasdone, among others.

Disintegrating agents can include starch, carboxymethylcellulose, hydroxypropylstarch, substituted hydroxypropylcellulose, sodium bicarbonate, calcium phosphate, and calcium citrate, among others Emollients can include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

Alternatively, the use of sustained delivery devices can be desirable, in order to avoid the necessity for the patient to take medications on a daily basis. The term "sustained delivery" is used herein to refer to delaying the release of an active agent, i.e., a compound of the invention, until after placement in a delivery environment, followed by a sustained release of the agent at a later time. A number of sustained delivery devices are known in the art and include hydrogels (U.S. Pat. Nos. 5,266,325; 4,959,217; 5,292,515), osmotic pumps (U.S. Pat. Nos. 4,295,987 and 5,273,752 and European Patent No. 314,206, among others); hydrophobic membrane materials, such as ethylenemethacrylate (EMA) and ethylenevinylacetate (EVA); bioresorbable polymer systems (International Patent Publication No. WO 98/44964 and U.S. Pat. Nos. 5,756,127 and 5,854,388); and other bioresorbable implant devices composed of, for example, polyesters, polyanhydrides, or lactic acid/glycolic acid copolymers (U.S. Pat. No. 5,817,343). For use in such sustained delivery devices, the compounds of the invention can be formulated as described herein.

III. Formulation Delivery

The present invention provides methods of providing the compounds of the invention to a patient. The compounds can be delivered by a route such as oral, dermal, transdermal, intrabronchial, intranasal, intravenous, intramuscular, subcutaneous, parenteral, intraperitoneal, sublingual, intracranial, epidural, intratracheal, intranasal, vaginal, rectal, or by sustained release. Preferably, delivery is oral.

In one embodiment, the compositions are delivered orally in solid or liquid form by powder, tablet, capsule, microcapsules, dispersible powder, granule, suspension, syrup, elixir, and aerosol.

Desirably, when the compound is delivered orally, it is sub-divided in a dose containing appropriate quantities of the active ingredient. The unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. Preferably, the powders and tablets contain up to 99% of the active ingredient.

In another embodiment, the compounds are delivered intravenously, intramuscularly, subcutaneously, parenterally and intraperitoneally in the form of sterile injectable solutions, suspensions, dispersions, and powders which are fluid to the extent that easy syringe ability exits. Such injectable compositions are sterile, stable under conditions of manufacture and storage, and free of the contaminating action of microorganisms such as bacteria and fungi.

Injectable formations can be prepared by combining the compound with a liquid. The liquid can be selected from among water, glycerol, ethanol, propylene glycol and polyethylene glycol, oils, and mixtures thereof, and more preferably the liquid carrier is water. In one embodiment, the oil is vegetable oil. Optionally, the liquid carrier contains about a suspending agent.

In a further embodiment, the compounds are delivered rectally or vaginally in the form of a conventional suppository.

In yet another embodiment, the compositions are delivered intranasally or intrabronchially in the form of an aerosol.

In a further embodiment, the compositions are delivered transdermally or by sustained release through the use of a transdermal patch containing the composition and an optional carrier that is inert to the compound, is nontoxic to the skin, and allows for delivery of the compound for systemic absorption into the blood stream. Such a carrier can be a cream, ointment, paste, gel, or occlusive device. The creams and ointments can be viscous liquid or semisolid emulsions. Pastes can include absorptive powders dispersed in petroleum or hydrophilic petroleum. Further, a variety of occlusive devices can be utilized to release the active reagents into the blood stream and include semi-permeable membranes covering a reservoir contain the active reagents, or a matrix containing the reactive reagents.

IV. Methods of Use

The compounds of the present invention have utility for the prevention and treatment of disorders involving beta amyloid production, including cerebrovascular diseases, and the prevention and treatment of AD by virtue of their ability to reduce beta amyloid production.

In preliminary studies using protease specific assays, the compounds of the invention have been shown to exhibit specific inhibition with respect to protease activity. Thus, the compounds of the present invention are useful for treatment and prevention of a variety of conditions in which modulation of beta amyloid levels provides a therapeutic benefit. Such conditions include, e.g., amyloid angiopathy, cerebral amyloid angiopathy, systemic amyloidosis, Alzheimer's Disease (AD), hereditary cerebral hemorrhage with amyloidosis of the Dutch type, inclusion body myositis, Down's syndrome and mild cognitive impairment, among others.

The compounds of the present invention have also been shown to inhibit beta amyloid production. In one embodiment, a subject or patient can be monitored for circulating levels of the compounds and/or beta-amyloid levels, from time to time following administration of a compound of the invention, or during the course of treatment. A variety of assays can be utilized for this purpose, including those described below. Additionally, cellular, cell-free and in vivo screening methods, as well as radioimmunoassays and enzyme-linked immunosorbent assay (ELISA) to detect inhibitors of beta amyloid production are known in the art (See, e.g., P. D. Mehta, et al., Techniques in Diagnostic Pathology, vol. 2, eds., Bullock et al, Academic Press, Boston, pages 99–112 (1991), International Patent Publication No. WO 98/22493, European Patent No. 0 652 009, and U.S. Pat. Nos. 5,703,129 and 5,593,846).

The compounds can further be utilized in generating reagents useful in diagnosis of conditions associated with abnormal levels of beta amyloid. For example, the compounds of Formula I can be used to generate antibodies which would be useful in a variety of diagnostic assays. Methods for generating monoclonal, polyclonal, recombinant, and synthetic antibodies or fragments thereof, are well known to those of skill in the art. See, e.g., E. Mark and Padlin, "Humanization of Monoclonal Antibodies", Chapter 4, The Handbook of Experimental Pharmacology, Vol. 113, The Pharmacology of Monoclonal Antibodies, Springer-Verlag (June, 1994); Kohler and Milstein and the many known modifications thereof; International Patent Application No. PCT/GB85/00392; British Patent Application Publication No. GB2188638A; Amit et al., Science, 233:747–753 (1986); Queen et al., Proc. Nat'l. Acad. Sci. USA, 86:10029–10033 (1989); International Patent Publication No. WO 90/07861; and Riechmann et al., Nature, 332:323–327 (1988); Huse et al, Science, 246:1275–1281 (1988). Alternatively, the compounds of Formula I can themselves be used in such diagnostic assays. Regardless of the reagent selected (e.g., antibody or compound of Formula I), suitable diagnostic formats including, e.g., radioimmunoassays and enzyme-linked immunosorbent assays (ELISAs), are well known to those of skill in the art and are not a limitation on this embodiment of the invention.

The following examples are provided to illustrate the production and activity of representative compounds of the invention and to illustrate their performance in a screening assay. One skilled in the art will appreciate that although specific reagents and conditions are outlined in the following examples, these reagents and conditions are not a limitation on the present invention.

EXAMPLES

Example 1

2-Bromo-N-[(1S,2S)-1-(hydroxymethyl)-2-methyl-butyl]benzenesulfonamide

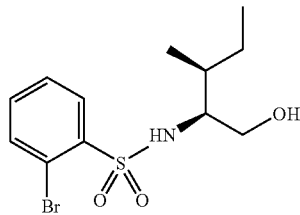

To a solution of (S) isoleucinol (23 mg, 0.2 mmol) in THF (3 mL) was added triethylamine (46 µL, 0.24 mmol) and 2-bromobenzenesulfonyl chloride (51 mg, 0.2 mmol). The solution was stirred for 8 to 16 hours, then concentrated. The residue was dissolved in MeOH (1.5 mL) and purified by semi-preparative RP-HPLC using the following conditions:

Column: Phenomenex C18 Luna 21.6 mm×60 mm, 5µ

Solvent A: Water (0.02% TFA buffer)

Solvent B: Acetonitrile (0.02% TFA buffer)

Solvent Gradient: Time 0:10% B; 2.5 min: 10% B; 14 min: 90% B.

Flow Rate: 22.5 mL/min

The product peak was collected based on UV absorption and concentrated to give Example 1 (37.7 mg).

The following compounds (Table 1; Examples 1-13) were prepared using 2-bromobenzenesulfonyl chloride, 3-bromobenzenesulfonyl chloride, 3-chloro benzenesulfonyl chloride, 4-chloro-7-chlorosulfonyl-2,1,3-benzoxadiazole, 2-chloro-4-fluorobenzenesulfonyl chloride, 5-chloro-2-methoxy-benzenesulfonyl chloride, 2-chloro-6-methylbenzenesulfonyl chloride, 3,5-dichlorobenzenesulfonyl chloride, 2,4-difluoro benzenesulfonyl chloride, 4-fluorobenzenesulfonyl chloride, 2-fluorobenzenesulfonyl chloride, 1-naphthalenesulfonyl chloride, and 2-naphthalenesulfonyl chloride and following the procedure outlined in Example 1. This procedure is outlined in the following Scheme.

TABLE 1

LCMS Data[1]

| $RSO_2Cl$ | Example | Molecular ion and retention time |
|---|---|---|
| 2-bromobenzenesulfonyl chloride | 1 | (338.0 M + H); 2.850 min |
| 3-bromobenzenesulfonyl chloride | 2 | (338.0 M + H); 3.014 min |
| 3-chlorobenzenesulfonyl chloride | 3 | (292.1 M + H); 2.949 min |
| 4-chloro-7-chlorosulfonyl-2,1,3-benzoxadiazole | 4 | (334.1 M + H); 3.073 min |
| 2-chloro-4-fluorobenzenesulfonyl chloride | 5 | (311.1 M + H); 2.910 min |
| 5-chloro-2-methoxy-benzenesulfonyl chloride | 6 | (322.1 M + H); 3.018 min |
| 2-chloro-6-methylbenzenesulfonyl chloride | 7 | (306.1 M + H); 3.017 min |
| 3,5-dichlorobenzenesulfonyl chloride | 8 | (326.0 M + H); 3.320 min |
| 2,4-difluorobenzenesulfonyl chloride | 9 | (294.1 M + H); 2.740 min |
| 4-fluorobenzenesulfonyl chloride | 10 | (277.1 M + H); 2.691 min |
| 2-fluorobenzenesulfonyl chloride | 11 | (276.1 M + H); 2.608 min |
| 1-naphthalenesulfonyl chloride | 12 | (308.1 M + H); 3.087 min |
| 2-naphthalenesulfonyl chloride | 13 | (308.1 M + H); 3.103 min |

[1]LCMS conditions: Hewlett Packard 1100 MSD; YMC ODS-AM 2.0 mm × 50 mm 5µ column at 23° C.; 3 µL injection; Solvent A: 0.02% TFA/water; Solvent B: 0.02% TFA/acetonitrile; Gradient: Time 0: 95% A; 0.3 min: 95% A; 4.7 min: 10% A; 4.9 min: 95% A. Flow rate 1.5 mL/min; Detection: 254 nm DAD; API-ES Scanning Mode Positive 150–700; Fragmentor 70 mV.

Example 14

3-Amino-4-chloro-N-[(1S,2S)-1-(hydroxymethyl)-2-methylbutyl]benzenesulfonamide

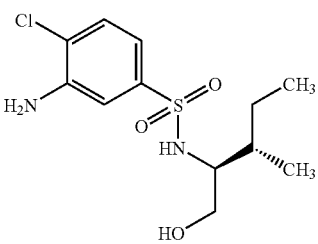

A. Preparation of 3-Nitro-4-chloro-N-[(1S,2 S)-1-(hydroxymethyl)-2-methylbutyl]benzenesulfonamide To a solution of S-isoleucinol (3.0 g, 25.6 mmol), triethylamine (2.85 g, 28.2 mmol) and methylene chloride (30 mL) at 0° C., was added a solution of 4-chloro-3-nitro-benzenesulfonyl chloride (6.55 g, 25.6 mmol) in $CH_2Cl_2$ (30 mL). After 15 minutes, the ice bath was removed and the reaction allowed to reach 25° C. After 16 hours, the reaction was quenched by pouring into a saturated sodium bicarbonate solution (125 mL). The organic phase was separated and washed sequentially with 1N HCl solution (100 mL), distilled water and brine, dried over $MgSO_4$ and evaporated to give a crude solid that was recrystallized from ethyl acetate-hexane (5.52 g, 64%). MS (+ESI) 354 ($[M+NH_4]^+$). Anal. Calc'd for $C_{12}H_{17}ClN_2O_5S$: C, 42.80; H, 5.09; N, 8.32; Found: C, 42.82; H, 5.05; N, 8.23.

B. Preparation of 3-Amino-4-chloro-N-[(1S,2S)-1-(hydroxymethyl)-2-methylbutyl]benzenesulfonamide A standard hydrogenation bottle was charged with 3-nitro-4-chloro-N-[(1S,2S)-1-(hydroxymethyl)-2-methylbutyl]benzenesulfonamide (0.50 g, 1.48 mmol), 10% palladium on carbon (0.05 g), methanol (25 mL) and hydrogen gas. It was shaken on a Parr hydrogenation apparatus for 50 minutes. The reaction mixture was filtered and the solvent evaporated to produce a crude oil that was flash chromatographed (eluant: ethyl acetate-hexane, 3–2) to afford the product as a solid, mp 89–92° C. (0.12 g, 26%). MS (+APCI) 307.03 ($[M+H]^+$). Anal. Calc'd for $C_{12}H_{19}ClN_2O_3S$: C, 46.98; H, 6.24; N, 9.13; Found: C, 47.44; H, 6.32; N, 8.88.

Example 15

N-[(1S)-1-benzyl-2-hydroxyethyl]-4-bromobenzenesulfonamide

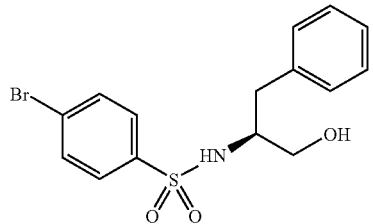

To a solution of (S)-(–) 2-amino-3-phenyl-1-propanol (37 mg, 0.25 mmol) in THF (3 mL) was added triethylamine (58 uL, 0.3 mmol) and 4-bromobenzenesulfonyl chloride (63 mg, 0.25 mmol). The solution was stirred for 8 to 16 hours, then concentrated. The residue was dissolved in MeOH (1.5 mL) and purified by semi-preparative RP-HPLC using the conditions described in Example 1 to give Example 15 (9.8 mg). This procedure is outlined in the following Scheme.

TABLE 2

(LCMS Data[1]: Molecular ion and retention time)

| $R_1R_2NH$ | |
|---|---|
| (S)-(–) 2-amino-3-phenyl-1-propanol | Example 15; (372.0 M + H); 3.110 min |

Example 16

4-Bromo-N-[(1S)-1-cyclohexyl-2-hydroxyethyl]benzenesulfonamide

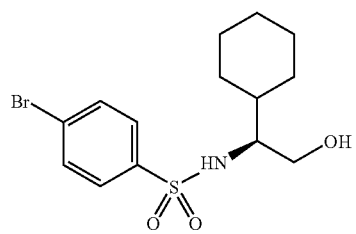

To a solution of 4-bromobenzenesulfonyl chloride (102 mg, 0.4 mmol) in THF (1 mL) was added L-cyclohexylglycine (77.4 mg, 0.4 mmol) in 1 N sodium hydroxide (1 mL). The reaction was shaken at 25° C. for 16 hours, then concentrated.

The residue was dissolved in THF (1 mL) and lithium aluminum hydride (1 M solution in THF, 0.8 mmol, 0.8 mL) was added and the reaction shaken for 2 hours. Water (240 μL), 15% sodium hydroxide (240 μL) and water (960 μL)

were added with shaking between each addition. The reaction mixture was filtered and the filtrate concentrated and purified as described for Example 1 to give Example 16 (1.9 mg). This procedure is outlined in the following Scheme.

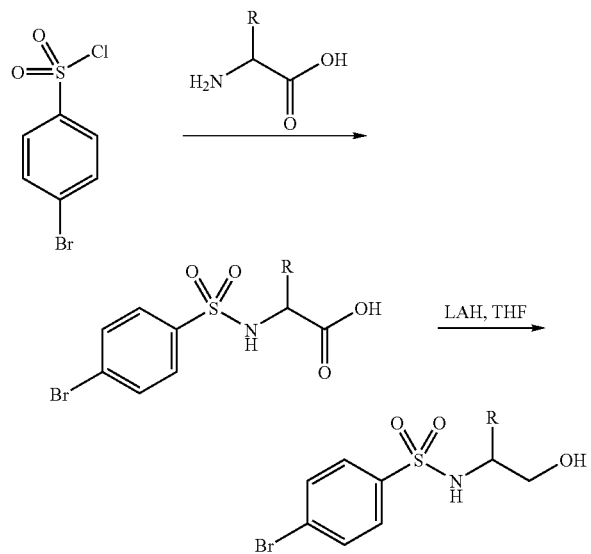

The following compounds (Examples 16–19, Table 3) were prepared using 4-bromobenzensulfonyl chloride with L-cyclohexylglycine, D-4-hydroxyphenylglycine, D-methionine, and L-tryptophan and following the procedure outlined in Example 16.

TABLE 3

(LCMS Data[1]: Molecular ion and retention time)

| Amino Acid | Example | Molecular Ion | Retention time (min) |
|---|---|---|---|
| L-cyclohexylglycine | 16 | (364.0 M + H) | 3.216 |
| D-4-hydroxy phenylglycine | 17 | (374.0 M + H) | 2.371 |
| D-methionine | 18 | (355.0 M + H) | 2.692 |
| L-tryptophan | 19 | (411.0 M + H) | 3.004 |

Example 20

4-Bromo-2,5-difluoro-N-[(1S,2S)-1-(hydroxymethyl)-2methylbutyl]benzenesulfonamide

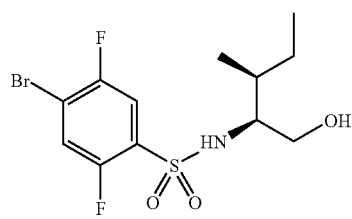

To a solution of (S)-isoleucinol (23 mg, 0.2 mmol) in THF (3 mL) was added triethylamine (46 μL, 0.24 mmol) and 4-bromo-2,5-difluorobenzenesulfonyl chloride (58 mg, 0.2 mmol). The solution was stirred for 8 to 16 hours. The solvent was removed and the residue purified as described for Example 1 to give Example 20 (4.7 mg).

The following compounds (Table 4) were prepared using (S)-(+)-isoleucinol, (S)-(+)-2-amino-3-methyl-1-butanol, and (S)-tert-leucinol with 4-bromo-2,5-difluoro benzenesulfonyl chloride, 2,5-dibromobenzenesulfonyl chloride, 3,4-dibromo benzenesulfonyl chloride, 2,3-dichlorobenzenesulfonyl chloride, 3,4-dichloro benzenesulfonyl chloride, 2,4,5-trichlorobenzenesulfonyl chloride, and 2,4,6-trichloro benzenesulfonyl chloride and following the procedure outlined in Example 20.

This procedure is outlined in the following Scheme.

TABLE 4

(LCMS Data[1]: Molecular ion and retention time)

| RSO₂Cl | (S)-(+)-isoleucinol | (S)-(+)-2-amino-3-methyl-1-butanol | (S)-tert-leucinol |
|---|---|---|---|
| 4-bromo-2,5-difluorobenzenesulfonyl chloride | Ex. 20 (374.0 M + H); 3.663 min | Ex. 26 (358.0 M + H); 3.006 min | |
| 2,5-dibromobenzenesulfonyl chloride | Ex. 21 (417.9 M + H); 3.340 min | | |
| 3,4-dibromobenzenesulfonyl chloride | Ex. 22 (415.9 M + H); 3.387 min | | Ex. 29 (415.9 M + H); 3.357 min |
| 2,3-dichlorobenzenesulfonyl chloride | Ex. 23 (328.0 M + H); 3.152 min | | |
| 3,4-dichlorobenzenesulfonyl chloride | Ex. 24 (328.0 M + H); 3.314 min | Ex. 27 (312.0 M + H); 3.105 min | Ex. 30 (326.0 M + H); 3.041 min |
| 2,4,5-trichlorobenzenesulfonyl chloride | Ex. 25 (362.0 M + H); 3.533 min | | Ex. 31 (362.0 M + H); 3.505 min |
| 2,4,6-trichlorobenzenesulfonyl chloride | | Ex. 28 (348.0 M + H); 3.210 min | Ex. 32 (362.0 M+ H); 3.404 min |

Example 33

4-Bromo-N-[(1R,2R)-1-(hydroxymethyl)-2-methylbutyl]benzenesulfonamide

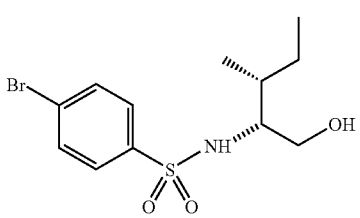

To a solution of D-isoleucine (32.8 mg, 0.25 mmol) in THF (2 mL) was added lithium aluminum hydride (1 M solution in THF) (0.8 mL, 0.8 mmol) and the solution was heated at 60° C. for 4 hours. The solution was then stirred at 25° C. for 8 to 16 hours. The reaction was quenched by addition of water (45 μL), 15% aqueous sodium hydroxide (45 μL) and water (105 μL) with vigorous stirring between each addition. The mixture was then filtered and concentrated.

To the residue in THF (3 mL) was added triethylamine (69 μL, 0.50 mmol) and 4-bromobenzenesulfonyl chloride (63.9 mg, 0.25 mmol). The solution was stirred for 8 to 16 hours, then concentrated and the residue purified as described for Example 1 to give 50.8 mg.

The following compounds (Examples 33–39, Table 5) were prepared using 4-bromobenzenesulfonyl chloride, and 4-chlorobenzenesulfonyl chloride, with D-isoleucine, L-α-methyl-valine, β-methyl-DL-phenylalanine, and L-allo-isoleucine and following the procedure outlined in Example 33. This procedure is outlined in the following Scheme.

TABLE 5

(LCMS Data[1]: Molecular ion and retention time)

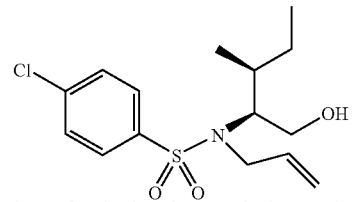

| | RSO$_2$Cl | |
|---|---|---|
| Amino Acid | 4-bromobenzenesulfonyl chloride | 4-chlorobenzenesulfonyl chloride |
| D-isoleucine | Ex. 33 (336.0 M + H); 2.858 min | |
| L-α-methyl-valine | Ex. 34 (338.0 M + H); 2.872 min | Ex. 37 (292.0 M + H); 2.806 min |
| β-methyl-DL-phenylalanine | Ex. 35 (386.0 M + H); 3.089 min | Ex. 38 (342.0 M + H); 3.035 min |
| L-allo-isoleucine | Ex. 36 (336.0 M + H); 2.828 min | Ex. 39 (292.0 M + H); 2.763 min |

Example 40

N-Allyl-4-chloro-N-[(1S,2 S)-1-(hydroxymethyl)-2-methylbutyl]benzenesulfonamide

To a solution of L-isoleucine methyl ester hydrochloride (1.82 g, 10 mmol) and 4-chlorobenzenesulfonyl chloride (2.11 g, 10 mmol) in CH$_2$Cl$_2$ was added triethylamine (4.18 mL, 30 mmol). The mixture was stirred at 25° C. for 16 hours, then filtered and concentrated. The crude product was purified by flash chromatography over silica gel using 10% ethyl acetate in hexane to give N-4-chlorobenzenesulfonyl L-isoleucine methyl ester 3.53 g.

To a solution of N-4-chlorobenzenesulfonyl L-isoleucine methyl ester (80 mg, 0.25 mmol) in a mixture of DCM (1.5 mL) and THF (1.5 mL) was added allyl alcohol (17 μL, 0.25 mmol), triphenylphosphine (66 mg, 0.25 mmol) and diethylazodicarboxylate (39 μL, 0.25 mmol). The reaction was shaken at 25° C. for 24 hours.

Lithium borohydride (11 mg, 0.5 mmol) was added to this reaction solution and the reaction was shaken at 45° C. for 24 hours then quenched by addition of water (2 mL) and extracted into ethyl acetate (3.5 mL). The organic phase was evaporated and the residue purified as described for Example 1 to give 11.6 mg.

The following compounds (Examples 40–48, Table 6) were prepared using allyl alcohol, 4-biphenylmethanol, t-butyl N-(2-hydroxyethyl)-carbamate, p-chlorobenzyl alcohol, cyclobutanemethanol, 3,4-dimethoxybenzyl alcohol, furfuryl alcohol, 2-(methylthio)ethanol, and 3-phenyl-2-propyn-1-ol and following the procedure outlined in Example 40. This procedure is outlined in the following Scheme.

TABLE 6

(LCMS Data[1])

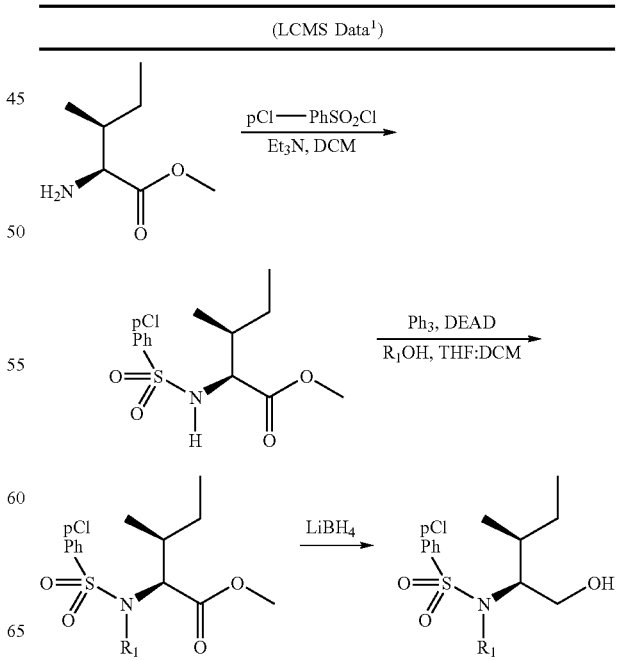

TABLE 6-continued (LCMS Data[1])

| $R_1OH$ | Example | Molecular Ion | Retention Time |
|---|---|---|---|
| allyl alcohol | 40 | 332.24 M + H | 3.57 min |
| 4-biphenylmethanol | 41 | 458.0 M + H | 4.225 min |
| t-butyl N-(2-hydroxyethyl)-carbamate | 42 | 435.33 M + H | 3.68 min |
| p-chlorobenzyl alcohol | 43 | 416.14 M + H | 3.97 min |
| cyclobutanemethanol | 44 | 360.31 M + H | 3.97 min |
| 3,4-dimethoxybenzyl alcohol | 45 | 442.1 M + H | 3.333 min |
| furfuryl alcohol | 46 | 372.1 M + H | 3.403 min |
| 2-(methylthio)ethanol | 47 | 366.27 M + H | 3.69 min |
| 3-phenyl-2-propyn-1-ol | 48 | 406.33 M + H | 4.05 min |

Example 49

4-Chloro-N-[(1S,2R)-1-(hydroxymethyl)-2-(4-methoxyphenyl)propyl]benzenesulfonamide

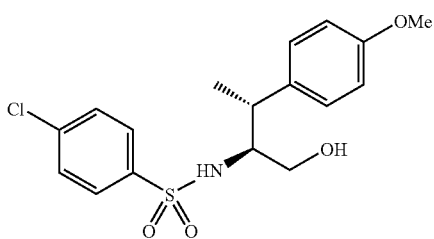

Part 1:

A solution of 2-pentenoic acid (4.05 mL, 40 mmol) in THF (100 mL) was cooled to −78° C. Triethylamine (5.85 mL, 42 mmol) and trimethylacetyl chloride (pivaloyl chloride) (5.17 mL, 42 mmol) were added via syringe in that order. The dry ice bath was replaced with an ice bath and the reaction stirred at 0° C. for 1 hour, then the reaction was recooled to −78° C. In a separate flask 4-(R)-4-benzyl-2-oxazolidinone (7.0 g, 40 mmol) was dissolved in THF (100 mL) and cooled to −78° C., then n-butyl lithium (1.6 M, 25 mL) was added via syringe. The mixture was stirred for 20 minutes then the above reaction mixture was added by removing the septum and pouring quickly from one flask to the other (Note* attempts to transfer reaction mixture via cannula failed due to the suspended triethylammonium chloride in the mixture).

The resulting mixture was stirred at −78° C. for 30 minutes then allowed to warm to 25° C. for 1 to 2 hours before quenching with saturated aqueous NH$_4$Cl solution (100 mL). Volatiles were removed on the rotary evaporator and the aqueous slurry was diluted with water (200 mL) and extracted with ethyl acetate (2×200 mL). The combined organic phase was dried over MgSO$_4$, filtered and concentrated. The product may crystallize out of solution and be of high purity. If purification is required, the crude product can be purified by flash chromatography using 20–30% ethyl acetate in hexane.

Part 2:

To a copper (I) bromide-dimethyl sulfide complex (246 mg, 1.2 mmol) in THF/DMS (2:1, 15 mL), cooled to −40° C., was added 4-methoxyphenyl magnesium bromide (4.8 mL 0.5 M solution in THF, 2.4 mmol). The solution was allowed to stir for 10 minutes while warming to −15° C. The mixture was recooled to −40° C. and the product from Part 1 (245 mg, 1 mmol) in THF (6 mL) was added. The solution was stirred at 25° C. for 8 to 16 hours. The solution was cooled to −78° C. and N-bromosuccinimide (356 mg, 2 mmol) in THF (2 mL) was added. The solution was allowed to warm to 0° C. and shaken at 0° C. for 3 hours. The reaction was quenched with a 1:1 solution of saturated ammonium carbonate and 0.5 N potassium bisulfate (5 mL). The organic phase was decanted off and concentrated.

Part 3:

To the product from Part 2 dissolved in acetonitrile (5 mL) was added tetramethylguanidine azide (0.6 mL, 4 mmol). The solution was stirred for 72 to 120 hours. The solution was concentrated to dryness, redissolved in CH$_2$Cl$_2$ and 1 N HCl (2 mL) was added. The layers were separated and the organic layer was filtered through a pad of silica gel, washed with CH$_2$Cl$_2$ (5 mL) and concentrated.

Part 4:

To the product from Part 3 (131 mg, 1 mmol) in THF (5 mL) at 0° C. was added lithium aluminum hydride (1 M solution in THF) (2 mL, 2 mmol) and the solution stirred at 25° C. for 4 hours. The reaction was quenched by addition of water (114 μL), 15% aqueous sodium hydroxide (114 μL), and water (266 μL) with vigorous stirring between each addition. The mixture was then filtered and concentrated.

Part 5:

To the solution from Part 4 (0.5 mmol) in THF (2 mL) was added triethylamine (83.7 μL, 0.6 mmol) and 4-chlorobenzenesulfonyl chloride (130.8 mg, 0.5 mmol). The solution was stirred for 8 to 16 hours, then concentrated. The solvent was removed and the residue purified as described for Example 1 to give 50.8 mg.

The following compounds (Examples 49–70, Table 7) were prepared using 4-chlorobenzenesulfonyl chloride with crotonic acid, 2-pentenoic acid, 2-hexenoic acid, 2-octenoic acid, cinnamic acid, furylacrylic acid, and 4-methyl-2-pentenoic acid and methyl, ethyl, isobutyl, 4-methoxyphenyl, hexyl and phenyl magnesium bromide and following the procedure outlined in Example 49. This procedure is outlined in the following Scheme.

TABLE 7

(LCMS Data[1]: Molecular ion and retention time)

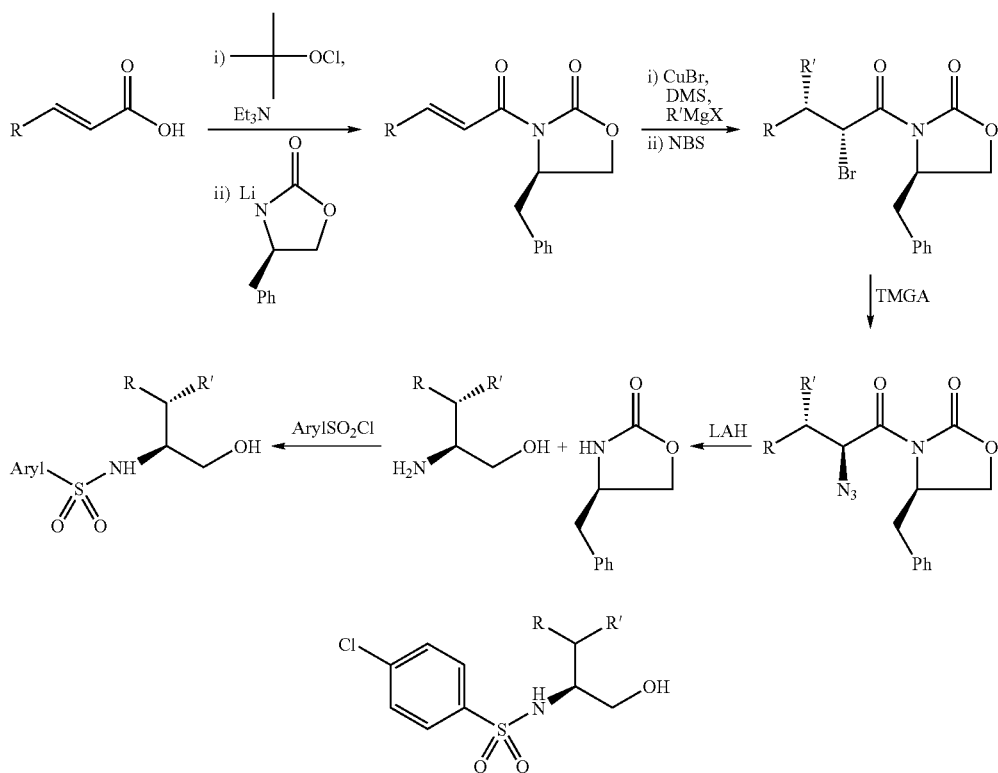

| R | R'MgX | | | | | |
|---|---|---|---|---|---|---|
| | methyl | Ethyl | isobutyl | 4-methoxy-phenyl | n-hexyl | phenyl |
| Methyl | | | | Ex. 49 (370.0 M + H); 3.168 min | Ex. 50 (348.1 M + H); 4.017 min | Ex. 51 (340.0 M + H); 3.244 min |
| Ethyl | | Ex. 52 (306.0 M + H); 3.189 min | Ex. 53 (334.0 M + H); 3.648 min | | | |
| n-propyl | Ex. 54 (306.0 M + H); 3.215 min | Ex. 55 (320.0 M + H); 3.372 min | Ex. 56 (348.1 M + H); 3.891 min | Ex. 57 (398.1 M + H); 3.635 min | Ex. 58 (376.1 M + H); 4.415 min | Ex. 59 (368.1 M + H); 3.706 min |
| n-pentyl | Ex. 60 (334.1 M + H); 3.746 min | Ex. 61 (348.1 M + H); 3.949 min | | | Ex. 62 (404.2 M + H); 4.834 min | |
| Phenyl | Ex. 63 (340.0 M + H); 3.259 min | | Ex. 64 (382.1 M + H); 3.876 min | | Ex. 65 (410.1 M + H); 4.366 min | |
| 2-furyl | | Ex. 66 (344.0 M + H); 3.225 min | Ex. 67 (372.1 M + H); 3.649 min | | Ex. 68 (400.1 M + H); 4.152 min | |
| i-propyl | Ex. 69 (306.0 M + H); 3.199 min | | | | Ex. 70 (376.1 M + H); 4.414 min | |

The following compounds (Examples 71–87, Table 8) were prepared using 4-bromobenzenesulfonyl chloride with crotonic acid, 2-pentenoic acid, 2-hexenoic acid, 2-octenoic acid, cinnamic acid, b-(3-pyridyl)-acrylic acid, furylacrylic acid, and 4-methyl-2-pentenoic acid and methyl, ethyl, isobutyl, 4-methoxyphenyl, and hexyl magnesium bromide and following the procedure outlined in Example 49.

TABLE 8

(LCMS Data[1]: Molecular ion and retention time)

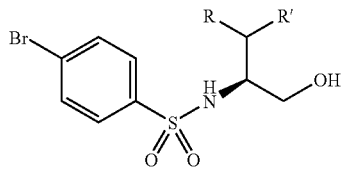

| R | R' | | | | |
|---|---|---|---|---|---|
| | Methyl | ethyl | Isobutyl | 4-methoxyphenyl | n-hexyl |
| Methyl | | | | Ex. 71 (414.0 M + H); 3.230 min | Ex. 72 (394.0 M + H); 4.071 min |
| Ethyl | | | Ex. 73 (380.0 M + H); 3.710 min | Ex. 74 (430.0 M + H); 3.460 min | Ex. 75 (406.1 M + H); 4.256 min |
| n-propyl | Ex. 76 (352.0 M + H); 3.291 min | Ex. 77 (364.0 M + H); 3.422 min | Ex. 78 (394.0 M + H); 3.949 min | | Ex. 79 (422.1 M + H); 4.466 min |
| n-pentyl | Ex. 80 (380.0 M + H); 3.797 min | Ex. 81 (392.1 M + H); 4.007 min | | | |
| Phenyl | Ex. 82 (386.0 M + H); 3.328 min | Ex. 83 (398.0 M + H); 3.546 min | | | |
| 2-furyl | Ex. 84 (376.0 M + H); 3.057 min | Ex. 85 (388.0 M + H); 3.305 min | Ex. 86 (418.0 M + H); 3.712 min | | |
| i-propyl | | | Ex. 87 (394.0 M + H); 3.948 min | | |

Example 88

4-Chloro-N-[(1 S,2S)-2-ethyl-1-(hydroxymethyl) octyl]benzenesulfonamide

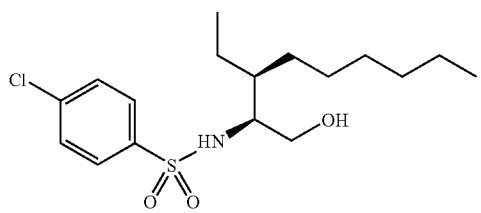

Following the procedure outlined in Example 49 (Part 1 and 2),2-pentenoic acid was coupled with 4-(R)-4-benzyl-2-oxazolidinone to give (R)-3-(2'-pentenyl)-4-benzyl-2-oxazolidinone. Addition of hexyl magnesium bromide was followed by trapping by N-bromosuccinimide. After workup, flash chromatography over silica gel using 5% ether in hexane, gave approximately a 2:1 mixture of (1R-2R):(1R-2S)-3-(2'-bromo-3'ethylnonanyl)-4-benzyl-2-oxazolidinone. Each isomer was converted to the corresponding sulfonylated amino alcohol following the procedure in Example 49, (Steps 3–5).

TABLE 9

(LCMS Data[1]: Molecular ion and retention time)

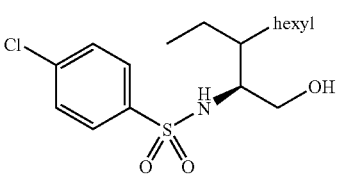

| Isomer | Example | Molecular Ion | Retention Time (min) |
|---|---|---|---|
| 1S-2S | 88 | 363 M + H | 4.24 min |
| 1S-2R | 89 | 363 M + H | 4.24 min |

Example 90

4-Chloro-N-methyl-N-[(1S,2S)-1-(hydroxymethyl)-2-methylbutyl]benzenesulfonamide

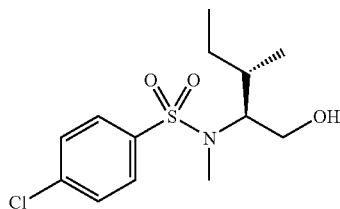

To a solution of 4-chloro-N-[(1S,2S)-1-(hydroxymethyl)-2-methylbutyl]benzenesulfonamide (0.10 g, 0.343 mmol) dissolved in DMF (2.0 mL) was added potassium carbonate (47 mg, 0.343 mmol). After 30 minutes, the reaction mixture was cooled to 0° C. and iodomethane (50 µL, 0.686 mmol) was added. After 2 hours, the ice bath was removed and the reaction mixture was stirred at 25° C. for 24 hours. The insolubles were then filtered off and the DMF solution was diluted with EtOAc (50 mL) and washed sequentially with 10% citric acid (50 mL) and saturated brine (50 mL), dried over MgSO$_4$ and evaporated to a clear oil which was washed with Et$_2$O and then purified by flash chromatography (eluant: 95-5 CHCl$_3$/iPrOH) to afford the desired product as a clear oil (71 mg, 68%). Mass Spectrum (+APCI): 306 ([M+H]$^+$). Anal: Calc'd for $C_{13}H_{20}ClNO_3S$: C, 51.06; H, 6.59; N, 4.58. Found: C, 51.15; H, 6.73; N, 4.36.

Example 91

4-Chloro-N-[(1S,2S)-1-(hydroxymethyl)-2-methylbutyl]benzenesulfonamide

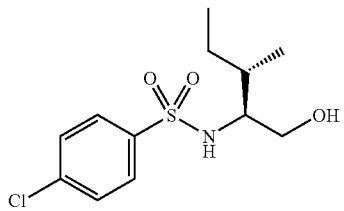

To a solution of (S)-isoleucinol (17.6 mg, 0.15 mmol) in CH$_3$CN (600 µL) was added Et$_3$N (300 µL, 1 M in CH$_3$CN) and 4-chlorobenzenesulfonyl chloride (21.07 mg, 0.1 mmol) as a solution in CH$_3$CN (400 µL). The vial was capped and shaken for 8 to 12 hours at 40° C. The solvent was removed, and the oil was dissolved in EtOAc (1 mL). The resulting solution was washed with 1M HCl (2×1 mL). The solvent was removed in vacuo, and the residue dissolved in 1.6 mL DMSO (0.03 M).

The following compounds (Examples 91–119, Table 10) were prepared using 4-chloro, 4-bromo, 3-chloro, and 3-fluorobenzenesulfonyl chloride with (S)-isoleucinol, L-leucinol, DL-2-amino-1-hexanol, (1S, 2R)-(+)-phenylpropanolamine, (S)-(+)-2-phenylglycinol, (R)-(−)-leucinol, 1-amino-1-cyclopentanemethanol, DL-2-amino-1-pentanol, (S)-2-amino-3-cyclohexyl-1-propanol, H-tyrosinol(bzl), (R)-(+)-methioninol, (S)-(+)-2-amino-1-butanol, (1S,2S)-(+)-thiomicamine, L-alaninol, L-phenylalaninol, L-valinol, and (R)-(+)-2-amino-2-methyl-1-butanol following the procedure outlined in Example 91. This procedure is outlined in the following Scheme.

TABLE 10

(LCMS Data[2]: Molecular ion and retention time)

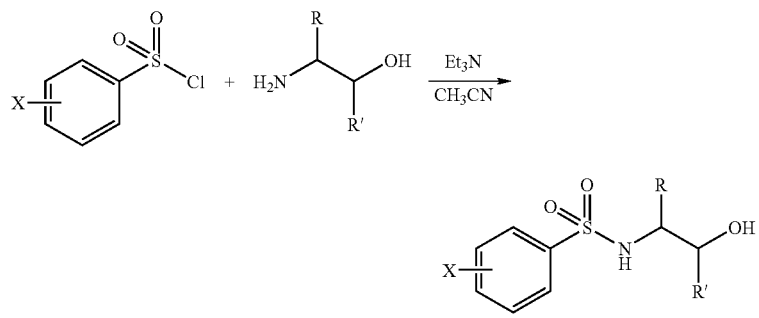

| Aminoalcohol | 4-chloro-Ph | 4-bromo-Ph | 3-chloro-Ph | 3-fluoro-Ph |
|---|---|---|---|---|
| (S)-isoleucinol | Ex. 91<br>290.54 (M − H)<br>0.96 min | Ex. 98<br>334.48 (M − H)<br>1.00 min | | |
| L-leucinol | Ex. 92<br>290.53 (M − H)<br>0.96 min | | | Ex. 109<br>274.57 (M − H)<br>0.87 min |
| DL-2-amino-1-hexanol | | Ex. 99<br>334.49 (M − H)<br>1.02 min | | Ex. 110<br>274.55 (M − H)<br>0.86 min |

TABLE 10-continued (LCMS Data[2]: Molecular ion and retention time)

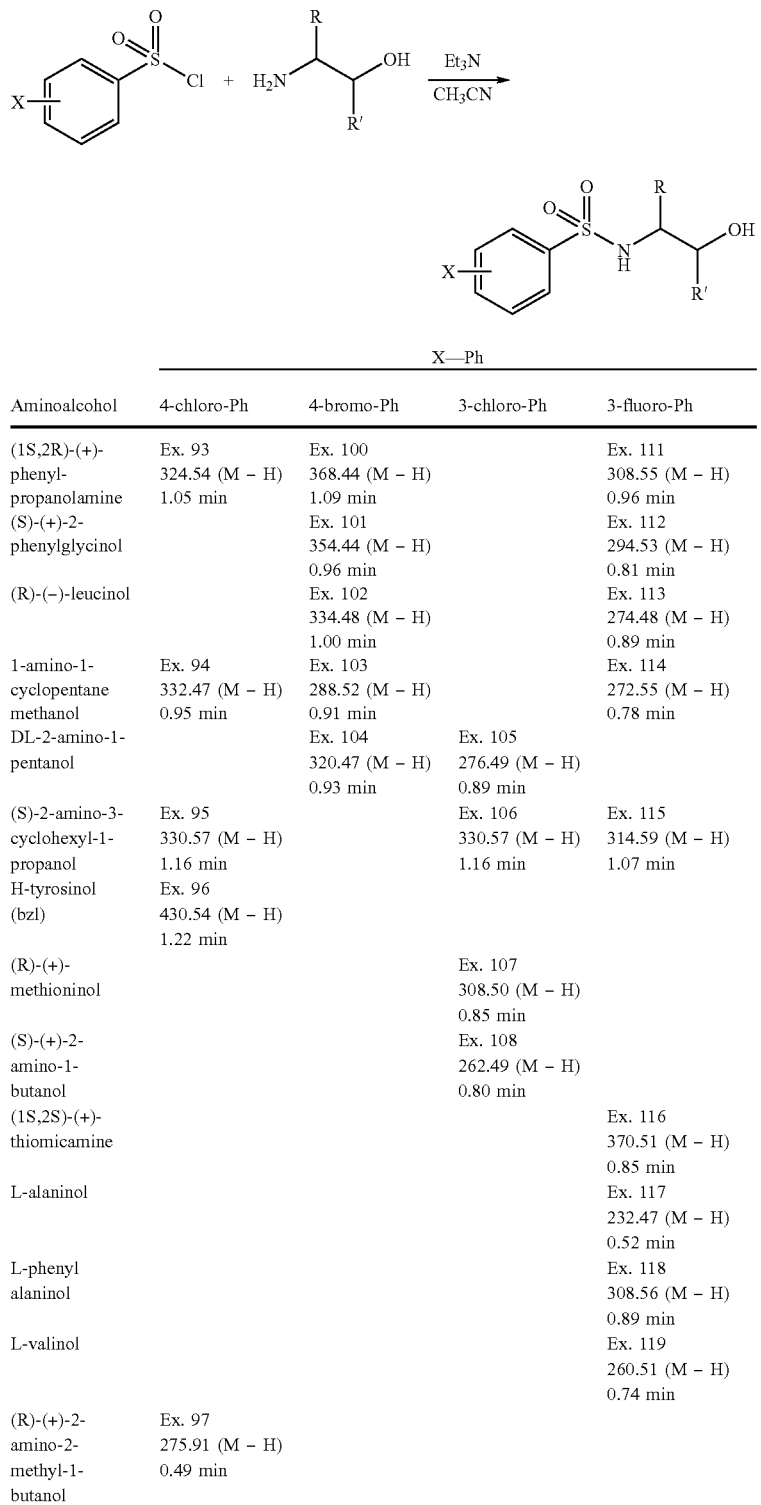

| | X—Ph | | | |
|---|---|---|---|---|
| Aminoalcohol | 4-chloro-Ph | 4-bromo-Ph | 3-chloro-Ph | 3-fluoro-Ph |
| (1S,2R)-(+)-phenyl-propanolamine | Ex. 93<br>324.54 (M − H)<br>1.05 min | Ex. 100<br>368.44 (M − H)<br>1.09 min | | Ex. 111<br>308.55 (M − H)<br>0.96 min |
| (S)-(+)-2-phenylglycinol | | Ex. 101<br>354.44 (M − H)<br>0.96 min | | Ex. 112<br>294.53 (M − H)<br>0.81 min |
| (R)-(−)-leucinol | | Ex. 102<br>334.48 (M − H)<br>1.00 min | | Ex. 113<br>274.48 (M − H)<br>0.89 min |
| 1-amino-1-cyclopentane methanol | Ex. 94<br>332.47 (M − H)<br>0.95 min | Ex. 103<br>288.52 (M − H)<br>0.91 min | | Ex. 114<br>272.55 (M − H)<br>0.78 min |
| DL-2-amino-1-pentanol | | Ex. 104<br>320.47 (M − H)<br>0.93 min | Ex. 105<br>276.49 (M − H)<br>0.89 min | |
| (S)-2-amino-3-cyclohexyl-1-propanol | Ex. 95<br>330.57 (M − H)<br>1.16 min | | Ex. 106<br>330.57 (M − H)<br>1.16 min | Ex. 115<br>314.59 (M − H)<br>1.07 min |
| H-tyrosinol (bzl) | Ex. 96<br>430.54 (M − H)<br>1.22 min | | | |
| (R)-(+)-methioninol | | | Ex. 107<br>308.50 (M − H)<br>0.85 min | |
| (S)-(+)-2-amino-1-butanol | | | Ex. 108<br>262.49 (M − H)<br>0.80 min | |
| (1S,2S)-(+)-thiomicamine | | | | Ex. 116<br>370.51 (M − H)<br>0.85 min |
| L-alaninol | | | | Ex. 117<br>232.47 (M − H)<br>0.52 min |
| L-phenyl alaninol | | | | Ex. 118<br>308.56 (M − H)<br>0.89 min |
| L-valinol | | | | Ex. 119<br>260.51 (M − H)<br>0.74 min |
| (R)-(+)-2-amino-2-methyl-1-butanol | Ex. 97<br>275.91 (M − H)<br>0.49 min | | | |

[2]LCMS conditions: ZMD (Waters) or Platform (Micromass) or LCZ (Micromass); column: Zorbax SB-C8; solvent: AcCN + $H_2O$ containing 0.1% TFA or 0.1% FA; gradient: 2.5 min 15% AcCN-95% AcCN; flow rate: 3 mL/min; detection: ELSD detection (SEDEX 55); UV253 detection (Schimadzu).

Example 120

4-Bromo-N-[1-(hydroxymethyl)-cyclohexyl]-benzenesulfonamide

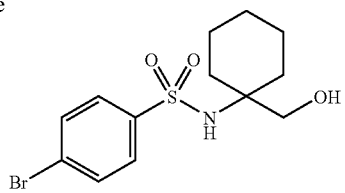

Part 1:

To a suspension of 1-amino-1-cyclohexane carboxylic acid (5 g, 35 mmol) and THF (100 mL) was added borane dimethyl sulfide (50 mL, 2M in THF) at 0° C. The cold bath was allowed to expire and the reaction was stirred at 25° C. for 24 hours. NaOH (3M, 100 mL) was added and the mixture was stirred for 4 hours. The reaction mixture was saturated with $K_2CO_3$ and extracted with $Et_2O$ (2×100 mL). The combined organic extracts were washed with brine (100 mL) and dried over $MgSO_4$ and evaporated to give 4.35 g (96%) of the desired amino alcohol.

Part 2:

The amino alcohol was sulfonylated as in example 91.

The following compounds (Examples 120-125, Table 11) were prepared using the following amino acids: 1-amino-1-cyclohexane carboxylic acid, 2-amino-2-norbornane carboxylic acid, d, 1-1-aminoindane-1-carboxylic acid, and d-1-2-cyclobutyl-2-phenylglycine with 4-bromo and 4-chlorobenzenesulfonyl chloride following the procedure outlined for example 120. This procedure is outlined in the following Scheme.

TABLE 11

(LCMS Data[2]: Molecular ion and retention time)

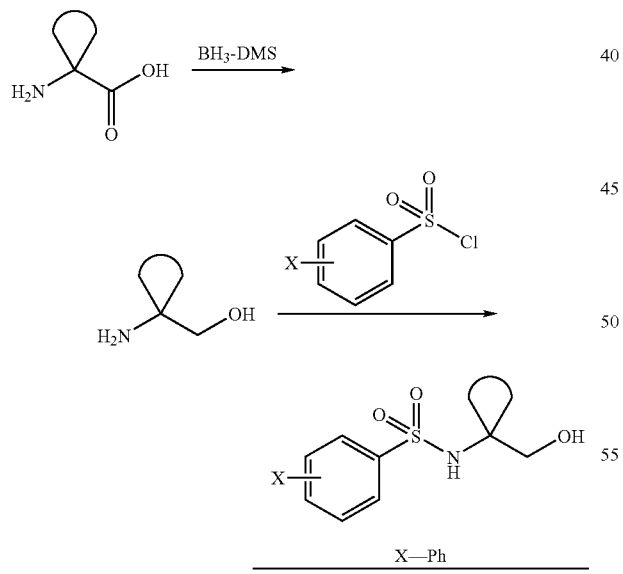

| Amino Acid | 4-bromo-Ph | 4-chloro-Ph |
|---|---|---|
| 1-amino-1-cyclohexane carboxylic acid | Example 120<br>348.07 (M − H)<br>1.02 min | Example 123<br>302.18 (M − H)<br>1.00 min |
| 2-amino-2-norbornane carboxylic acid | Example 121<br>360.05 (M − H)<br>1.07 min | |
| d,l-1-aminoindane-1-carboxylic acid | Example 122<br>381.96 (M − H)<br>1.06 min | Example 124<br>336.17 (M − H)<br>1.04 min |
| d,l-2-cyclobutyl-2-phenylglycine | | Example 125<br>364.21 (M − H)<br>1.22 min |

Example 165A

4-Chloro-N-[(1S,2S)-1-formyl-2-methylbutyl]benzenesulfonamide

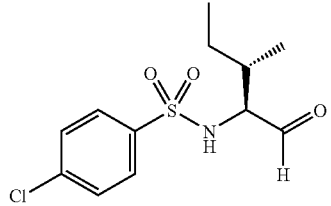

To a solution of 4-chlorobenzenesulfonyl chloride (1.93 g, 9.1 mmol) in $CH_3CN$ (25 mL) and (S)-isoleucinol (1.07 g, 9.1 mmol) was added $Et_3N$ (1.91 mL, 13.7 mmol). The reaction mixture was stirred at 25° C. for 30 minutes. The solvent was removed and the oil was dissolved in $CH_2Cl_2$ (20 mL). The solution was washed with water (2×20 mL) and dried over $Na_2SO_4$. The solvent was removed to give N-4-chloro benzenesulfonyl isoleucinol, which was carried on without further purification.

To a stirred solution of N-4-chlorobenzenesulfonyl isoleucinol (~9.1 mmol) in $CH_2Cl_2$ (100 mL) was added a mixture of pyridinium chlorochromate (5.88 g, 27.3 mmol) and silica gel (~6 g). The resulting slurry was stirred at 25° C. until the alcohol was consumed by TLC analysis. The reaction mixture was diluted with $Et_2O$ (250 mL) and filtered through wet silica gel (eluant: 20% EtOAc/hex). Following removal of solvent, the residue was subjected to a Biotage™ eluting with 10→20% EtOAc/hex to give 1.94 g (74%, two steps) of the aldehyde (LCMS=288.14 (M−H), rt=1.07 min).

Example 165

4-Chloro-N-[(1S,2S)-1-(hydroxyethyl)-2-methylbutyl]benzenesulfonamide

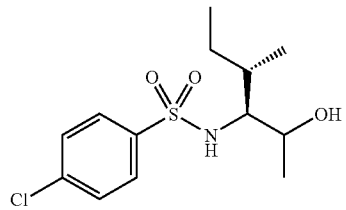

To a solution of the aldehyde from Example 165A (23.1 mg, 80 mmol) in THF (400 μL) was added methyl magnesium bromide (400 μL, 1.0 M in THF, 5 eq). The vial was capped and agitated at 50° C. for 12 hours. The reaction was quenched with saturated aqueous $NH_4Cl$ (1.5 mL) and EtOAc (1 mL). The organic layer was transferred into a tared vial and the aqueous layer was extracted with EtOAc (1 mL). The combined organics were concentrated (Savant, medium heat) and the resulting mixture of diastereomers was dissolved in DMSO such that the final concentration was 30 mM.

The following compounds (Examples 126-210, Table 12) were prepared using N-4-fluoro, 4-bromo, 4-chloro, 3-chloro and 2-fluorophenylsulfonyl isoleucinal with methylmagnesium bromide, cyclopentylmagnesium bromide, hexylmagnesium bromide, pentylmagnesium bromide, butylmagnesium bromide, isopropylmagnesium bromide, o-tolylmagnesium bromide, tert-butylmagnesium bromide, isobutylmagnesium bromide, vinylmagnesium bromide, allylmagnesium bromide, ethylmagnesium bromide, 4-fluorophenylmagnesium bromide, 4-chlorophenylmagnesium bromide, 2-methyl-1-propenylmagnesium bromide, isopropenylmagnesium bromide, 4-anisylmagnesium bromide, 1-methyl-1-propenylmagnesium bromide, 2-[2-(1,3-dioxanyl)]ethylmagnesium bromide, 3-butenylmagnesium bromide, 1-propynylmagnesium bromide, 4-thioanisolemagnesium bromide, 4-N,N-dimethylanilinemagnesium bromide, and 1-naphthylmagnesium bromide following the procedures outlined in examples 165A and 165. This procedure is outlined in the following Scheme.

TABLE 12

(LCMS Data[2]: Molecular ion and retention time(s))

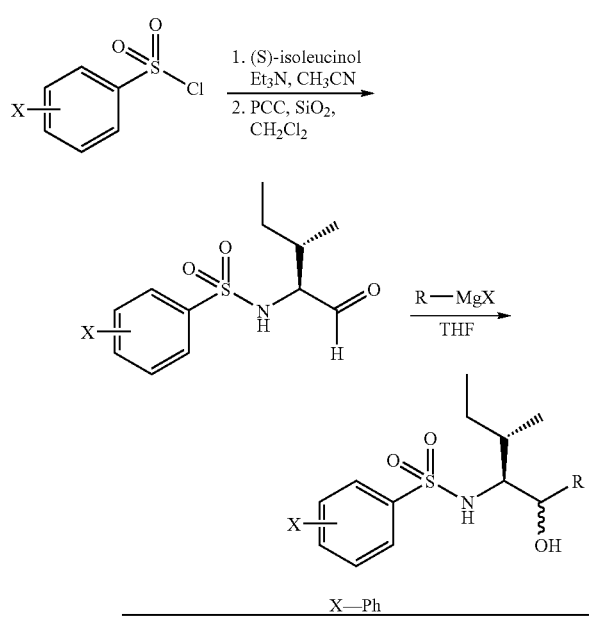

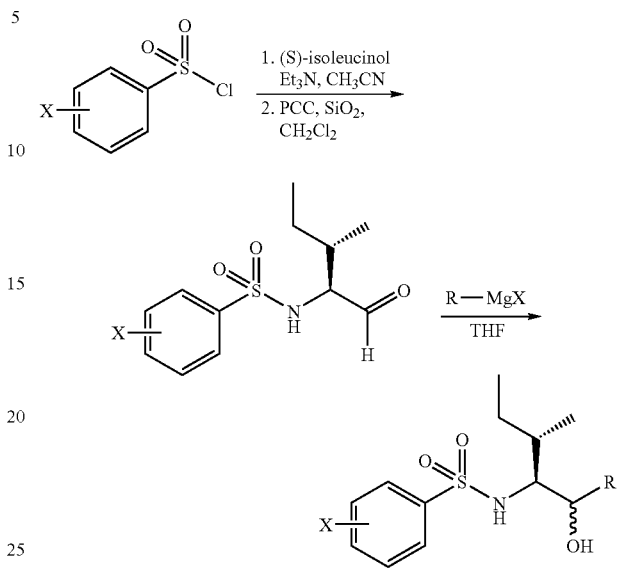

X—Ph

| RMgX | 4-fluoro-Ph | 4-bromo-Ph | 4-chloro-Ph | 3-chloro-Ph | 2-fluoro-Ph |
|---|---|---|---|---|---|
| Methyl magnesium bromide | Ex. 126 288.18 (M − H) 1.01 min | Ex. 145 350.05 (M − H) 1.12 min | Ex. 165 304.10 (M − H) 1.04 min, 1.10 min | Ex. 185 394.15 (M − H) 1.05 min, 1.12 min | |
| Cyclopentyl magnesium bromide | Ex. 127 242.21 (M − H) 1.30 min | Ex. 146 404.05 (M − H) 1.40 min | Ex. 166 358.18 (M − H) 1.37 min | Ex. 186 358.18 (M − H) 1.39 min | Ex. 202 342.22 (M − H) 1.29 min |
| Hexyl magnesium bromide | Ex. 128 358.24 (M − H), 1.40 min, 1.44 min | | Ex. 167 374.21 (M − H) 1.48 min, 1.52 min | Ex. 187 374.22 (M − H) 1.48 min, 1.53 min | Ex. 203 358.24 (M − H) 1.41 min, 1.46 min |
| Pentyl magnesium bromide | Ex. 129 344.23 (M − H) 1.32 min, 1.36 min | Ex. 147 406.10 (M − H), 1.40 min, 1.46 min | Ex. 168 360.19 (M − H) 1.40 min, 1.45 min | Ex. 188 360.20 (M − H) 1.40 min, 1.46 min | Ex. 204 344.22 (M − H) 1.32 min, 1.36 min |
| Butyl magnesium bromide | Ex. 130 330.21 (M − H) 1.24 min, 1.28 min | Ex. 148 392.07 (M − H), 1.34 min, 1.39 min | Ex. 169 346.18 (M − H) 1.33 min, 1.37 min | Ex. 189 346.17 (M − H) 1.33 min, 1.38 min | Ex. 205 330.23 (M − H) 1.25 min, 1.30 min |
| Isopropyl magnesium bromide | | | Ex. 170 332.17 (M − H) 1.25 min, 1.30 min | Ex. 190 332.18 (M − H) 1.26 min, 1.31 min | |
| o-tolyl magnesium bromide | Ex. 131 364.19 (M − H) 1.28 min | | Ex. 171 380.17 (M − H) 1.36 min | | |
| tert-butyl magnesium bromide | Ex. 132 330.21 (M − H) 1.31 min | Ex. 149 392.08 (M − H) 1.42 min | Ex. 172 346.17 (M − H) 1.40 min | Ex. 191 346.18 (M − H) 1.40 min | |
| Isobutyl magnesium bromide | | Ex. 150 392.06 (M − H) 1.37 min | Ex. 173 346.17 (M − H) 1.33 min, 1.36 min | Ex. 192 346.18 (M − H) 1.31 min, 1.37 min | 1.32 min, |
| Vinyl magnesium bromide | Ex. 133 300.18 (M − H) 1.04 min, 1.08 min | Ex. 151 362.07 (M − H) 1.16 min, 1.20 min | Ex. 174 316.14 (M − H) 1.13 min, 1.17 min | Ex. 193 316.16 (M − H) 1.13 min, 1.18 min | Ex. 206 300.18 (M − H) 1.03 min, 1.08 min |
| Allyl magnesium bromide | Ex. 134 314.19 (M − H) 1.12 min, 1.16 min | Ex. 152 376.05 (M − H) 1.22 min, 1.26 min | Ex. 175 330.14 (M − H) 1.21 min, 1.25 min | Ex. 194 330.17 (M − H) 1.20 min, 1.25 min | |
| Ethyl magnesium bromide | Ex. 135 302.19 (M − H) 1.06 min, 1.11 min | Ex. 153 364.09 (M − H) 1.18 min, 1.23 min | Ex. 176 318.16 (M − H) 1.16 min, 1.21 min | Ex. 195 318.16 (M − H) 1.16 min, 1.21 min | |

TABLE 12-continued (LCMS Data[2]: Molecular ion and retention time(s))

[Reaction scheme: X-substituted benzenesulfonyl chloride reacts with (S)-isoleucinol (Et3N, CH3CN), then PCC, SiO2, CH2Cl2 to give the sulfonamide aldehyde, which reacts with R—MgX in THF to give the hydroxy sulfonamide product.]

X—Ph

| RMgX | 4-fluoro-Ph | 4-bromo-Ph | 4-chloro-Ph | 3-chloro-Ph | 2-fluoro-Ph |
|---|---|---|---|---|---|
| 4-fluoro phenyl magnesium bromide | | Ex. 154 429.99 (M − H) 1.28 min, 1.33 min | | | Ex. 207 368.17 (M − H) 1.18 min, 1.23 min |
| 4-chloro phenyl magnesium bromide | Ex. 136 384.14 (M − H) 1.26 min, 1.30 min | Ex. 155 446.01 (M − H) 1.35 min, 1.40 min | Ex. 177 402.03 (M − H) 1.33 min, 1.35 min | Ex. 196 402.06 (M − H) 1.33 min, 1.38 min | Ex. 208 384.14 (M − H) 1.25 min, 1.30 min |
| 2-methyl-1-propenyl magnesium bromide | Ex. 137 238.18 (M − H) 1.16 min, 1.21 min | Ex. 156 390.04 (M − H) 1.25 min, 1.31 min | | Ex. 197 344.19 (M − H) 1.24 min 1.30 min | |
| Isopropenyl magnesium bromide | Ex. 138 314.19 (M − H) 1.14 min, 1.17 min | Ex. 157 376.06 (M − H) 1.24 min, 1.28 min | | | |
| 4-anisyl magnesium bromide | Ex. 139 380.20 (M − H) 1.15 min, 1.21 min | Ex. 158 442.01 (M − H) 1.24 min, 1.30 min | Ex. 178 396.16 (M − H) 1.23 min, 1.29 min | Ex. 198 396.19 (M − H) 1.22 min, 1.28 min | Ex. 209 380.20 (M − H) 1.14 min, 1.19 min |
| 1-methyl-1-propenyl magnesium bromide | | Ex. 159 390.03 (M − H) 1.26 min, 1.35 min | | | |
| 2-[2-(1,3-dioxanyl)] ethyl magnesium bromide | Ex. 140 388.22 (M − H) 0.99 min, 1.04 min | Ex. 160 450.07 (M − H) 1.09 min, 1.15 min | Ex. 179 404.18 (M − H) 1.08 min, 1.13 min | Ex. 199 404.19 (M − H) 1.13 min | Ex. 210 388.21 (M − H) 0.98 min, 1.03 min |
| 3-butenyl magnesium bromide | Ex. 141 328.21 (M − H) 1.19 min, 1.23 min | Ex. 161 390.06 (M − H) 1.29 min, 1.33 min | Ex. 180 344.16 (M − H) 1.27 min, 1.31 min | Ex. 200 344.16 (M − H) 1.27 min, 1.31 min | |
| 1-propynyl magnesium bromide | | Ex. 162 374.01 (M − H) 1.19 min | Ex. 181 328.15 (M − H) 1.18 min | | |
| 4-thio anisole magnesium bromide | Ex.142 396.17 (M − H) 1.25 min, 1.29 min | Ex.163 458.01 (M − H) 1.33 min, 1.38 min | Ex.182 412.14 (M − H) 1.37 min | Ex.201 412.15 (M − H) 1.32 min, 1.37 min | |
| 4-N,N-dimethyl aniline magnesium bromide | Ex. 143 393.24 (M − H) 0.77 min, 0.81 min | Ex. 164 455.07 (M − H) 0.95 min | Ex. 183 409.22 (M − H) 0.92 min | | |
| 1-naphthyl magnesium bromide | Ex. 144 400.21 (M − H) 1.35 min | | Ex. 184 416.18 (M − H) 1.41 min | | |

Example 211

4-Bromo-N-[(1S,2S)-1-(1-hydroxy-1-methylethyl)-2-ethyl-butyl]benzenesulfonamide

Part 1:

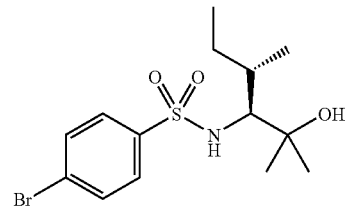

To a solution of 4-bromobenzenesulfonyl chloride (1.278 g, 5 mmol) in CH3CN (20 mL) was added (L)-isoleucine methyl ester hydrochloride (908.5 mg, 5 mmol) as a solution in CH3CN (10 mL) and Et3N (1 mL, 7.2 mmol). The reaction mixture was heated at 50° C. with shaking for 3 days. The solvent was removed and the oil was dissolved in EtOAc (10 mL). The solution was washed with water (5 mL), sat. NH₄OH (5 mL), brine (5 mL), and dried over MgSO₄. The solvent was removed to give 1.62 g (89%) of the desired sulfonamide ester.

To a solution of the sulfonamide ester (45.5 mg, 0.125 mmol) in THF (500 μL) was added methyl magnesium bromide (333 mL, 3.0 M in THF, 8 eq). The vial was capped and agitated at 50° C. for 12 hours. The reaction was quenched with saturated NH₄Cl (1.5 mL) and EtOAc (1 mL). The organic layer was transferred into a tared vial and the aqueous layer was extracted with EtOAc (1 mL). The combined organic extract was concentrated (Savant, medium heat) and the product was dissolved in DMSO such that the final concentration was 30 mM.

The following compounds (Examples 211-271, Table 13) were prepared using (from part 2) N-4-bromo, 4-chloro, 4-fluoro, 3-chloro and 2-fluorobenzenesulfonyl isoleucine methyl ester with methylmagnesium bromide, hexylmagnesium bromide, pentylmagnesium bromide, butylmagnesium bromide, isopropylmagnesium bromide, isobutylmagnesium bromide, allylmagnesium bromide, ethylmagnesium bromide, 4-fluorophenylmagnesium bromide, 4-chlorophenylmagnesium bromide, 2-methyl-1-propenylmagnesium bromide, isopropenylmagnesium bromide, 4-anisylmagnesium bromide, 1-methyl-1-propenylmagnesium bromide, 3-butenylmagnesium bromide, 1-propynylmagnesium bromide, 4-N,N-dimethylanilinemagnesium bromide, and 1-naphthylmagnesium bromide following the procedure outlined in example 211. This procedure is outlined in the following Scheme.

TABLE 13

(LCMS Data[2]: Molecular ion and retention time)

| RMgX | 4-bromo-Ph | 4-chloro-Ph | 4-fluoro-Ph | 3-chloro-Ph | 2-fluoro-Ph |
|---|---|---|---|---|---|
| Methyl magnesium bromide | Ex. 211 364.51 (M − H) 1.117 min | Ex. 223 318.61 (M − H) 1.15 min | Ex. 235 302.64 (M − H) 1.06 min | | |
| Hexyl magnesium bromide | | Ex. 224 458.78 (M − H) 1.87 min | Ex. 236 442.78 (M − H) 1.80 min | Ex. 249 458.75 (M − H) 1.87 min | Ex. 261 442.78 (M − H) 1.81 min |
| Pentyl magnesium bromide | Ex. 212 476.49 (M − H) 1.76 min | | Ex. 237 414.82 (M − H) 1.70 min | Ex. 250 430.76 (M − H) 1.76 min | Ex. 262 414.74 (M − H) 1.70 min |
| Butyl magnesium bromide | Ex. 213 448.59 (M − H) 1.65 min | Ex. 225 402.72 (M − H) 1.63 min | Ex. 238 386.73 (M − H) 1.58 min | Ex. 251 402.68 (M − H) 1.65 min | |
| Isopropyl magnesium bromide | | | Ex. 239 358.70 (M − H) 1.47 min | | |
| Isobutyl magnesium bromide | Ex. 214 448.58 (M − H) 1.65 min | Ex. 226 402.70 (M − H) 1.63 min | Ex. 240 386.73 (M − H) 1.58 min | Ex. 252 402.74 (M − H) 1.65 min | |
| Phenyl magnesium bromide | Ex. 215 488.51 (M − H) 1.50 min | Ex. 227 442.65 (M − H) 1.48 min | | Ex. 253 442.64 (M − H) 1.50 min | Ex. 263 426.67 (M − H) 1.43 min |
| Allyl magnesium bromide | Ex. 216 416.53 (M − H) 1.43 min | Ex. 228 370.65 (M − H) 1.41 min | Ex. 241 354.69 (M − H) 1.34 min | Ex. 254 370.64 (M − H) 1.43 min | Ex. 264 354.67 (M − H) 1.35 min |
| Ethyl magnesium bromide | Ex. 217 392.55 (M − H) 1.37 min | Ex. 229 346.67 (M − H) 1.35 min | Ex. 242 330.67 (M − H) 1.28 min | Ex. 255 346.66 (M − H) 1.37 min | Ex. 265 330.74 (M − H) 1.28 min |
| 4-fluoro phenyl magnesium bromide | | | | | Ex. 266 462.64 (M − H) 1.45 min |
| 4-chloro phenyl magnesium bromide | Ex. 218 556.39 (M − H) 1.61 min | | | Ex. 256 511.96 (M − H) 1.66 min | Ex. 267 494.57 (M − H) 1.56 min |

TABLE 13-continued (LCMS Data[2]: Molecular ion and retention time)

![Reaction scheme]

X—Ph

| RMgX | 4-bromo-Ph | 4-chloro-Ph | 4-fluoro-Ph | 3-chloro-Ph | 2-fluoro-Ph |
|---|---|---|---|---|---|
| isopropenyl magnesium bromide | Ex. 219<br>416.51<br>(M − H)<br>150 min | Ex. 230<br>370.64<br>(M − H)<br>1.48 min | Ex. 243<br>354.69<br>(M − H)<br>1.43 min | Ex. 257<br>370.66<br>(M − H)<br>1.48 min | Ex. 268<br>354.68<br>(M − H)<br>1.43 min |
| 4-anisyl magnesium bromide | | Ex. 231<br>502.64<br>(M − H)<br>1.43 min | Ex. 244<br>486.67<br>(M − H)<br>1.38 min | Ex. 258<br>502.62<br>(M − H)<br>1.43 min | Ex. 269<br>486.71<br>(M − H)<br>1.37 min |
| 1-methyl-1-propenyl magnesium bromide | Ex. 220<br>444.59<br>(M − H)<br>1.63 min | Ex. 232<br>398.69<br>(M − H)<br>1.61 min | Ex. 245<br>382.73<br>(M − H)<br>1.54 min | Ex. 259<br>398.65<br>(M − H)<br>1.61 min | Ex. 270<br>382.50<br>(M − H)<br>1.56 min |
| 3-butenyl magnesium bromide | Ex. 221<br>444.60<br>(M − H)<br>1.54 min | Ex. 233<br>398.66<br>(M − H)<br>1.52 min | Ex. 246<br>382.71<br>(M − H)<br>1.46 min | Ex. 260<br>518.68<br>(M − H)<br>1.21 min | Ex. 271<br>382.70<br>(M − H)<br>1.46 min |
| 4-N,N-dimethyl aniline magnesium bromide | | Ex. 247<br>512.73<br>(M − H)<br>0.97 min | | | |
| 1-naphthyl magnesium bromide | Ex. 222<br>558.46<br>(M − H)<br>1.65 min | Ex. 234<br>542.56<br>(M − H)<br>1.63 min | Ex. 248<br>526.69<br>(M − H)<br>1.58 min | | |

Example 272

4-Chloro-N-[(1S)-1-cyclohexyl-2-hydroxyethyl]benzenesulfonamide

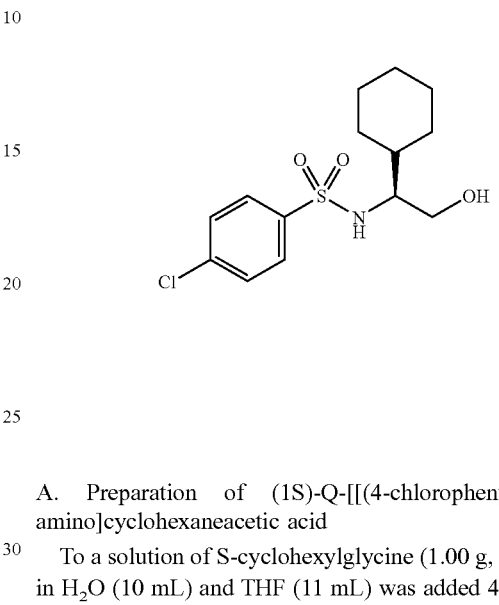

A. Preparation of (1S)-α-[[(4-chlorophenyl)sulfonyl]amino]cyclohexaneacetic acid To a solution of S-cyclohexylglycine (1.00 g, 5.16 mmol) in H$_2$O (10 mL) and THF (11 mL) was added 4-chlorobenzenesulfonyl chloride (1.53 g, 7.23 mmol) followed by 2.5N NaOH (8.26 mL) at 25° C. with stirring. After 24 hours, the reaction was quenched by addition of 6 N HCl until pH=2. The reaction mixture was then extracted with EtOAc (2×50 mL). The combined organic extracts were washed with saturated brine (2×50 mL), dried over MgSO$_4$, and evaporated to afford a white solid. This white solid was taken up in Et$_2$O, filtered and evaporated to afford an amorphous white solid which after washing with hexane afforded 0.90 g (52%) of product, mp 120-128° C. Mass Spectrum (+ESI): 354 ([M+Na]$^+$). Anal: Calc'd for $C_{14}H_{18}ClNO_4S$: C, 50.68; H, 5.47; N, 4.22. Found: C, 50.59; H, 5.46; N, 4.19.

B. Preparation of 4-Chloro-N-[(1S)-1-cyclohexyl-2-hydroxyethyl] benzenesulfonamide To a solution of LAH (1.0 M in THF, 1.5 mL, 1.5 mmol) was added dropwise at 0° C. a solution of (αS)-α-[[(4-chlorophenyl)sulfonyl]amino]cyclohexaneacetic acid (0.50 g, 1.507 mmol) in THF (8.0 mL). After the addition was complete, the reaction mixture was allowed to warm to 25° C. After 24 hours, the reaction was quenched by sequential addition of H$_2$O (60 μL), 15% NaOH (60 μL) and H$_2$O (180 μL). The precipitate was filtered and washed with THF. The combined THF solution was evaporated to a clear oil which afforded a white solid after washing with hexane. This white solid was purified by flash chromatography (eluant: 1-1 hexane/ethyl acetate), washed with hexane and pumped on to afford 0.179 g (37%) of the desired product as a white solid, mp 115-118° C. Mass Spectrum (+APCI): 318 ([M+H]$^+$). Anal: Calc'd for $C_{14}H_{20}ClNO_3S$: C, 52.91; H, 6.34; N, 4.41. Found: C, 52.16; H, 6.25; N, 4.40.

Example 273

4-Chloro-N-[(1S)-2-hydroxy-1-phenylethyl]benzenesulfonamide

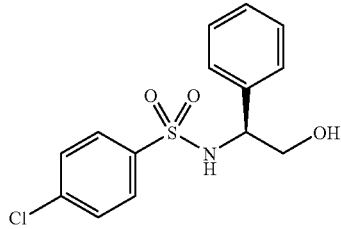

To a solution of S-2-phenyl-glycinol (0.50 g, 3.645 mmol) and Et₃N (0.561 mL, 4.01 mmol) in CH₂Cl₂ (7.5 mL) was added dropwise at 0° C. a solution of 4-chloro benzenesulfonyl chloride (0.769 g, 3.645 mmol) in CH₂Cl₂ (7.5 mL). After the addition was complete, the reaction mixture was allowed to warm to 25° C. After 24 hours, the reaction was diluted with CH₂Cl₂ (20 mL) and washed sequentially with saturated sodium bicarbonate (30 mL), 1N HCl (30 mL), H₂O (30 mL) and saturated brine (30 mL), dried over MgSO₄ and evaporated to a white solid which was washed with hexane twice. This white solid was purified by flash chromatography (eluant: 1-1 hexane/ethyl acetate), washed with hexane and pumped on to afford 0.347 g (29%) of the desired product as a white solid, mp 127-128° C. Mass Spectrum (+APCI): 329 ([M+NH₄]⁺). Anal: Calc'd for C₁₄H₁₄ClNO₃S: C, 53.93; H, 4.53; N, 4.49. Found: C, 53.96; H, 4.49; N, 4.39.

Example 274

4-Chloro-N-[(1S)-1-(hydroxymethyl)-2-methylpropyl]benzenesulfonamide

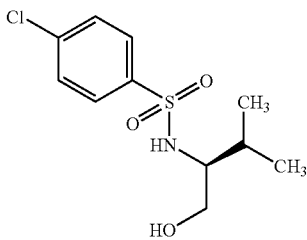

To a solution of S-valinol (0.52 g, 5.0 mmol), triethylamine (0.55 g, 5.5 mmol) and methylene chloride (10 mL) at 0° C., was added a solution of 4-chlorobenzenesulfonyl chloride (1.06 g, 5.0 mmol) in CH₂Cl₂ (5 mL). After 15 minutes the ice bath was removed and the reaction allowed to reach 25° C. After 16 hours, the reaction was quenched by pouring into saturated sodium bicarbonate solution (20 mL) and additional methylene chloride (15 mL). The organic phase was separated and washed sequentially with 1N HCl solution (20 mL), distilled water and brine, dried over MgSO₄ and evaporated to give a colorless oil that crystallized upon standing, mp 83-85° C. (1.30 g, 94%). MS (+ESI) 278.1 ([M+H]⁺); 257.2; 237.1. Anal. Calc'd for C₁₁H₁₆ClNO₃S: C, 47.56; H, 5.81; N, 5.04. Found: C, 47.78; H, 5.81; N, 4.99.

Example 275

4-Bromo-N-[(1S)-1-(hydroxymethyl)-2-methylpropyl]benzenesulfonamide

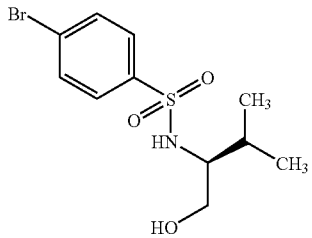

To a solution of S-valinol (0.52 g, 5.0 mmol), triethylamine (0.55 g, 5.5 mmol) and methylene chloride (10 mL) at 0° C., was added a solution of 4-bromobenzenesulfonyl chloride (1.28 g, 5.0 mmol) in CH₂Cl₂ (5 mL). After 15 minutes the ice bath was removed and the reaction allowed to reach 25° C. After 16 hours, the reaction was quenched by pouring into saturated sodium bicarbonate solution (20 mL) and additional methylene chloride (15 mL). The organic phase was separated and washed sequentially with 1N HCl solution (20 mL), distilled water and brine, dried over MgSO₄ and evaporated to give a colorless oil that crystallized upon standing under vacuum, mp 89-94° C. (1.49 g, 93%). MS (+APCI) 324.03 ([M+H]⁺). Anal. Calc'd for C₁₁H₁₆BrNO₃S: C, 41.00; H, 5.00; N, 4.35; Found: C, 41.09; H, 4.85; N, 4.28.

Example 276

4-Iodo-N-[(1S,2S)-1-(hydroxymethyl)-2-methylbutyl]benzenesulfonamide

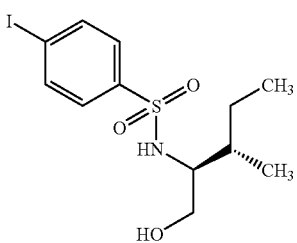

To a solution of S-isoleucinol (0.50 g, 4.26 mmol), triethylamine (0.47 g, 4.68 mmol) and methylene chloride (10 mL) at 0° C., was added a solution of 4-iodo benzenesulfonyl chloride (1.29 g, 4.26 mmol) in CH₂Cl₂ (5 mL). After 15 minutes the ice bath was removed and the reaction allowed to reach 25° C. After 16 hours, the reaction was quenched by pouring into saturated sodium bicarbonate solution (22 mL) and additional methylene chloride (15 mL). The organic phase was separated and washed sequentially with 1N HCl solution (25 mL), distilled water and brine, dried over MgSO₄ and evaporated to give a crude solid that was recrystallized from ethyl acetate-hexane, mp 118-120° C. (1.07 g, 66%). MS (+APCI) 383.96 ([M+H]⁺); 283.81; 191.95. Anal. Calc'd for C₁₂H₁₈INO₃S: C, 37.61; H, 4.73; N, 3.65; Found: C, 37.55; H, 4.61; N, 3.61.

Example 277

4-Chloro-N-[(1S)-1-(hydroxymethyl)-2,2-dimethylpropyl]benzenesulfonamide

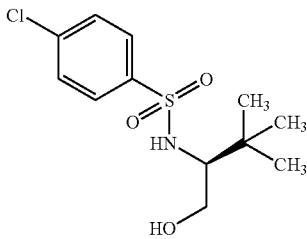

To a solution of S-tert-leucinol (0.20 g, 1.70 mmol), triethylamine (0.19 g, 1.87 mmol) and methylene chloride (10 mL) at 0° C., was added a solution of 4-chloro benzenesulfonyl chloride (0.36 g, 1.70 mmol) in $CH_2Cl_2$ (5 mL). After 15 minutes the ice bath was removed and the reaction allowed to reach 25° C. After 16 hours, the reaction was quenched by pouring into saturated sodium bicarbonate solution (20 mL) and additional-methylene chloride (15 mL). The organic phase was separated and washed sequentially with 1N HCl solution (20 mL), distilled water and brine, dried over $MgSO_4$ and evaporated to give the desired product as a white solid, mp 128-130° C. (0.46 g, 94%). MS (+APCI) 292.06 ([M+H]$^+$). Anal. Calc'd for $C_{12}H_{18}ClNO_3S$: C, 49.39; H, 6.22; N, 4.80; Found: C, 49.40; H, 6.17; N, 4.79.

TABLE 14

| Ex # | Compound |
|---|---|
| 1 | 2-bromo-N-[(1S,2S)-1-(hydroxymethyl)-2-methylbutyl]benzenesulfonamide |
| 2 | 3-bromo-N-[(1S,2S)-1-(hydroxymethyl)-2-methylbutyl]benzenesulfonamide |
| 3 | 3-chloro-N-[(1S,2S)-1-(hydroxymethyl)-2-methylbutyl]benzenesulfonamide |
| 4 | 4-chloro-N-[(1S,2S)-1-(hydroxymethyl)-2-methylbutyl]-1,2,3-benzoxadiazole-7-sulfonamide |
| 5 | 2-chloro-4-fluoro-N-[(1S,2S)-1-(hydroxymethyl)-2-methylbutyl]benzenesulfonamide |
| 6 | 5-chloro-N-[(1S,2S)-1-(hydroxymethyl)-2-methylbutyl]-2-methoxy benzenesulfonamide |
| 7 | 2-chloro-N-[(1S,2S)-1-(hydroxymethyl)-2-methylbutyl]-6-methyl benzenesulfonamide |
| 8 | 3,5-dichloro-N-[(1S,2S)-1-(hydroxymethyl)-2-methylbutyl]benzenesulfonamide |
| 9 | 2,4-difluoro-N-[(1S,2S)-1-(hydroxymethyl)-2-methylbutyl]benzenesulfonamide |
| 10 | 4-fluoro-N-[(1S,2S)-1-(hydroxymethyl)-2-methylbutyl]benzenesulfonamide |
| 11 | 2-fluoro-N-[(1S,2S)-1-(hydroxymethyl)-2-methylbutyl]benzenesulfonamide |
| 12 | N-[(1S,2S)-1-(hydroxymethyl)-2-methylbutyl]naphthalene-1-sulfonamide |
| 13 | N-[(1S,2S)-1-(hydroxymethyl)-2-methylbutyl]naphthalene-2-sulfonamide |
| 14 | 3-amino-4-chloro-N-[(1S,2S)-1-(hydroxymethyl)-2-methylbutyl] benzenesulfonamide |
| 15 | N-[(1S)-1-benzyl-2-hydroxyethyl]-4-bromobenzenesulfonamide |
| 16 | 4-bromo-N-[(1S)-1-cyclohexyl-2-hydroxyethyl]benzenesulfonamide |
| 17 | 4-bromo-N-[(1R)-2-hydroxy-1-(4-hydroxyphenyl)ethyl]benzenesulfonamide |
| 18 | 4-bromo-N-[(1S)-1-(hydroxymethyl)-3-methylbutyl]benzenesulfonamide |
| 19 | 4-bromo-N-[(1S)-2-hydroxy-1-(1H-indol-2-ylmethyl)ethyl]benzenesulfonamide |
| 20 | 4-bromo-2,5-difluoro-N-[(1S,2S)-1-(hydroxymethyl-2-methylbutyl] benzenesulfonamide |
| 21 | 2,5-dibromo-N-[(1S,2S)-1-(hydroxymethyl)-2-methylbutyl]benzenesulfonamide |
| 22 | 3,4-dibromo-N-[(1S,2S)-1-(hydroxymethyl)-2-methylbutyl]benzenesulfonamide |
| 23 | 2,3-dichloro-N-[(1S,2S)-1-(hydroxymethyl)-2-methylbutyl]benzenesulfonamide |
| 24 | 3,4-dichloro-N-[(1S,2S)-1-(hydroxymethyl)-2-methylbutyl]benzenesulfonamide |
| 25 | 2,4,5-trichloro-N-[(1S,2S)-1-(hydroxymethyl)-2-methylbutyl] benzenesulfonamide |
| 26 | 4-bromo-2,5-difluoro-N-[(1S)-1-(hydroxymethyl)-2-methylpropyl]benzenesulfonamide |
| 27 | 3,4-dichloro-N-[(1S)-1-(hydroxymethyl)-2-methylpropyl]benzenesulfonamide |
| 28 | 2,4,6-trichloro-N-[(1S)-1-(hydroxymethyl)-2-methylpropyl]benzenesulfonamide |
| 29 | 3,4-dibromo-N-[(1S)-1-(hydroxymethyl)-2,2-dimethylpropyl] benzenesulfonamide |
| 30 | 3,4-dichloro-N-[(1S)-1-(hydroxymethyl)-2,2-dimethylpropyl] benzenesulfonamide |
| 31 | 2,4,5-trichloro-N-[(1S)-1-(hydroxymethyl)-2,2-dimethylpropyl] benzenesulfonamide |
| 32 | 2,4,6-trichloro-N-[(1S)-1-(hydroxymethyl)-2,2-dimethylpropyl] benzenesulfonamide |
| 33 | 4-bromo-N-[(1R,2R)-1-(hydroxymethyl)-2-methylbutyl]benzenesulfonamide |
| 34 | 4-bromo-N-[(1S)-1-(hydroxymethyl)-1,2-dimethylpropyl]benzenesulfonamide |
| 35 | 4-bromo-N-[1-(hydroxymethyl)-2-phenylpropyl]benzenesulfonamide |
| 36 | 4-bromo-N-[(1S,2R)-1-(hydroxymethyl)-2-methylbutyl]benzenesulfonamide |
| 37 | 4-chloro-N-[(1S)-1-(hydroxymethyl)-1,2-dimethylpropyl]benzenesulfonamide |
| 38 | 4-chloro-N-[1-(hydroxymethyl)-2-phenylpropyl]benzenesulfonamide |
| 39 | 4-chloro-N-[(1S,2R)-1-(hydroxymethyl)-2-methylbutyl]benzenesulfonamide |
| 40 | N-allyl-4-chloro-N-[(1S,2S)-1-(hydroxymethyl)-2-methylbutyl] benzenesulfonamide |
| 41 | N-([1,1'-biphenyl]-4-ylmethyl)-4-chloro-N-[(1S,2S)-1-(hydroxymethyl)-2-methylbutyl]benzenesulfonamide |

TABLE 14-continued

| Ex # | Compound |
|---|---|
| 42 | tert-butyl 2-{[(4-chlorophenyl)sulfonyl][(1S,2S)-1-(hydroxymethyl)-2-methylbutyl]amino}ethylcarbamate |
| 43 | 4-chloro-N-(4-chlorobenzyl)-N-[(1S,2S)-1-(hydroxymethyl)-2-methylbutyl]benzenesulfonamide |
| 44 | 4-chloro-N-(cyclobutylmethyl)-N-[(1S,2S)-1-(hydroxymethyl)-2-methylbutyl]benzenesulfonamide |
| 45 | 4-chloro-N-(3,4-dimethoxybenzyl)-N-[(1S,2S)-1-(hydroxymethyl)-2-methylbutyl]benzenesulfonamide |
| 46 | 4-chloro-N-(2-furylmethyl)-N-[(1S,2S)-1-(hydroxymethyl)-2-methylbutyl]benzenesulfonamide |
| 47 | 4-chloro-N-[(1S,2S)-1-(hydroxymethyl)-2-methylbutyl]-N-[2-(methylthio)ethyl]benzenesulfonamide |
| 48 | 4-chloro-N-[(1S,2S)-1-(hydroxymethyl)-2-methylbutyl]-N-(3-phenylprop-2-ynyl)benzenesulfonamide |
| 49 | 4-chloro-N-[(1S,2R)-1-(hydroxymethyl)-2-(4-methoxyphenyl)propyl]benzenesulfonamide |
| 50 | 4-chloro-N-[(1S,2R)-1-(hydroxymethyl)-2-methyloctyl]benzenesulfonamide |
| 51 | 4-chloro-N-[(1S,2R)-1-(hydroxymethyl)-2-phenylpropyl]benzenesulfonamide |
| 52 | 4-chloro-N-[(1S)-2-ethyl-1-(hydroxymethyl)butyl]benzenesulfonamide |
| 53 | 4-chloro-N-[(1S,2R)-2-ethyl-1-(hydroxymethyl)-4-methylpentyl]benzenesulfonamide |
| 54 | 4-chloro-N-[(1S,2S)-1-(hydroxymethyl)-2-methylpentyl]benzenesulfonamide |
| 55 | 4-chloro-N-[(1S,2S)-2-ethyl-1-(hydroxymethyl)pentyl]benzenesulfonamide |
| 56 | 4-chloro-N-[(1S,2R)-1-(hydroxymethyl)-4-methyl-2-propylpentyl]benzenesulfonamide |
| 57 | 4-chloro-N-[(1S,2R)-1-(hydroxymethyl)-2-(4-methoxyphenyl)pentyl]benzenesulfonamide |
| 58 | 4-chloro-N-[(1S,2R)-1-(hydroxymethyl)-2-propyloctyl]benzenesulfonamide |
| 59 | 4-chloro-N-[(1S,2R)-1-(hydroxymethyl)-2-phenylpentyl]benzenesulfonamide |
| 60 | 4-chloro-N-[(1S,2S)-1-(hydroxymethyl)-2-methylheptyl]benzenesulfonamide |
| 61 | 4-chloro-N-[(1S,2S)-2-ethyl-1-(hydroxymethyl)heptyl]benzenesulfonamide |
| 62 | 4-chloro-N-[(1S,2R)-1-(hydroxymethyl)-2-pentyloctyl]benzenesulfonamide |
| 63 | 4-chloro-N-[(1S,2S)-1-(hydroxymethyl)-2-phenylpropyl]benzenesulfonamide |
| 64 | 4-chloro-N-[(1S,2S)-1-(hydroxymethyl)-4-methyl-2-phenylpentyl]benzenesulfonamide |
| 65 | 4-chloro-N-[(1S,2S)-1-(hydroxymethyl)-2-phenyloctyl]benzenesulfonamide |
| 66 | 4-chloro-N-[(1S,2R)-2-(2-furyl)-1-(hydroxymethyl)butyl]benzenesulfonamide |
| 67 | 4-chloro-N-[(1S,2R)-2-(2-furyl)-1-(hydroxymethyl)-4-methylpentyl]benzenesulfonamide |
| 68 | 4-chloro-N-[(1S,2R)-2-(2-furyl)-1-(hydroxymethyl)octyl]benzenesulfonamide |
| 69 | 4-chloro-N-[(1S,2S)-1-(hydroxymethyl)-2,3-dimethylbutyl]benzenesulfonamide |
| 70 | 4-chloro-N-[(1S,2S)-1-(hydroxymethyl)-2-isopropyloctyl]benzenesulfonamide |
| 71 | 4-bromo-N-[(1S,2R)-1-(hydroxymethyl)-2-(4-methoxyphenyl)propyl]benzenesulfonamide |
| 72 | 4-bromo-N-[(1S,2R)-1-(hydroxymethyl)-2-methyloctyl]benzenesulfonamide |
| 73 | 4-bromo-N-[(1S,2R)-2-ethyl-1-(hydroxymethyl)-4-methylpentyl]benzenesulfonamide |
| 74 | 4-bromo-N-[(1S,2R)-1-(hydroxymethyl)-2-(4-methoxyphenyl)butyl]benzenesulfonamide |
| 75 | 4-bromo-N-[(1S,2R)-2-ethyl-1-(hydroxymethyl)octyl]benzenesulfonamide |
| 76 | 4-bromo-N-[(1S,2S)-1-(hydroxymethyl)-2-methylpentyl]benzenesulfonamide |
| 77 | 4-bromo-N-[(1S,2S)-2-ethyl-1-(hydroxymethyl)pentyl]benzenesulfonamide |
| 78 | 4-bromo-N-[(1S,2R)-1-(hydroxymethyl)-4-methyl-2-propylpentyl]benzenesulfonamide |
| 79 | 4-bromo-N-[(1S,2R)-1-(hydroxymethyl)-2-propyloctyl]benzenesulfonamide |
| 80 | 4-bromo-N-[(1S,2S)-1-(hydroxymethyl)-2-methylheptyl]benzenesulfonamide |
| 81 | 4-bromo-N-[(1S,2S)-2-ethyl-1-(hydroxymethyl)heptyl]benzenesulfonamide |
| 82 | 4-bromo-N-[(1S,2S)-1-(hydroxymethyl)-2-phenylpropyl]benzenesulfonamide |
| 83 | 4-bromo-N-[(1S,2S)-1-(hydroxymethyl)-2-phenylbutyl]benzenesulfonamide |
| 84 | 4-bromo-N-[(1S,2R)-2-(2-furyl)-1-(hydroxymethyl)propyl]benzenesulfonamide |
| 85 | 4-bromo-N-[(1S,2R)-2-(2-furyl)-1-(hydroxymethyl)butyl]benzenesulfonamide |
| 86 | 4-bromo-N-[(1S,2R)-2-(2-furyl)-1-(hydroxymethyl)-4-methylpentyl]benzenesulfonamide |
| 87 | 4-bromo-N-[(1S,2S)-1-(hydroxymethyl)-isopropyl-4-methylpentyl]benzenesulfonamide |
| 88 | 4-chloro-N-[(1S,2S)-2-ethyl-1-(hydroxymethyl)octyl]benzenesulfonamide |
| 89 | 4-chloro-N-[(1S,2R)-2-ethyl-1-(hydroxymethyl)octyl]benzenesulfonamide |
| 90 | 4-chloro-N-methyl-N-[(1S,2S)-1-(hydroxymethyl)-2-methylbutyl]benzenesulfonamide |
| 91 | 4-chloro-N-[(1S,2S)-1-(hydroxymethyl)-2-methylbutyl]-benzenesulfonamide |
| 92 | 4-chloro-N-[(1S)-1-(hydroxymethyl)-3-methylbutyl]benzenesulfonamide |
| 93 | 4-chloro-N-[(1R,2S)-2-hydroxy-1-methyl-2-phenylethyl]benzenesulfonamide |
| 94 | 4-bromo-N-[1-(hydroxymethyl)cyclopentyl]benzenesulfonamide |
| 95 | 4-chloro-N-[(1S)-2-cyclohexyl-1-(hydroxymethyl)ethyl]benzenesulfonamide |
| 96 | N-{(1S)-1-[4-(benzyloxy)benzyl]-2-hydroxyethyl}-4-chlorobenzenesulfonamide |
| 97 | 4-chloro-N-[(1R)-1-(hydroxymethyl)-1-methylpropyl]benzenesulfonamide |
| 98 | 4-bromo-N-[(1S,2S)-1-(hydroxymethyl)-2-methylbutyl]-benzenesulfonamide |

TABLE 14-continued

| Ex # | Compound |
|---|---|
| 99 | 4-bromo-N-[1-(hydroxymethyl)pentyl]benzenesulfonamide |
| 100 | 4-bromo-N-[(1R,2S)-2-hydroxy-1-methyl-2-phenylethyl]benzenesulfonamide |
| 101 | 4-bromo-N-[(1S)-2-hydroxy-1-phenylethyl]benzenesulfonamide |
| 102 | 4-bromo-N-[(1R)-1-(hydroxymethyl)-3-methylbutyl]benzenesulfonamide |
| 103 | 4-chloro-N-[1-(hydroxymethyl)cyclopentyl]benzenesulfonamide |
| 104 | 4-bromo-N-[1-(hydroxymethyl)butyl]benzenesulfonamide |
| 105 | 3-chloro-N-[1-(hydroxymethyl)butyl]benzenesulfonamide |
| 106 | 3-chloro-N-[(1S)-2-cyclohexyl-1-(hydroxymethyl)ethyl]benzenesulfonamide |
| 107 | 3-chloro-N-[(1R)-1-(hydroxymethyl)-3-(methylthio)propyl]benzenesulfonamide |
| 108 | 3-chloro-N-[(1S)-1-(hydroxymethyl)propyl]benzenesulfonamide |
| 109 | 2-fluoro-N-[(1S)-1-(hydroxymethyl)-3-methylbutyl]benzenesulfonamide |
| 110 | 2-fluoro-N-[1-(hydroxymethyl)pentyl]benzenesulfonamide |
| 111 | 2-fluoro-N-(1R,2S)-2-hydroxy-1-methyl-2-phenylethyl]benzenesulfonamide |
| 112 | 2-fluoro-N-[(1S)-2-hydroxy-1-phenylethyl]benzenesulfonamide |
| 113 | 2-fluoro-N-[(1R)-1-(hydroxymethyl)-3-methylbutyl]benzenesulfonamide |
| 114 | 2-fluoro-N-[1-(hydroxymethyl)cyclopentyl]benzenesulfonamide |
| 115 | N-[(1S)-2-cyclohexyl-1-(hydroxymethyl)ethyl]-2-fluorobenzenesulfonamide |
| 116 | 2-fluoro-N-{(1S,2S)-2-hydroxy-1-(hydroxymethyl)-2-[4-(methylthio)phenyl]ethyl}benzenesulfonamide |
| 117 | 2-fluoro-N-[(1S)-1-(hydroxyl-methylethyl]benzenesulfonamide |
| 118 | N-[(1S)-1-benzyl-2-hydroxyethyl]-2-fluorobenzenesulfonamide |
| 119 | 2-fluoro-N-[(1S)-1-(hydroxymethyl)-2-methylpropyl]benzenesulfonamide |
| 120 | 4-bromo-N-[1-(hydroxymethyl)cyclohexyl]benzenesulfonamide |
| 121 | 4-bromo-N-[2-(hydroxymethyl)bicyclo[2.2.1].hept-2-yl]benzenesulfonamide |
| 122 | 4-bromo-N-[1-(hydroxymethyl)-2,3-dihydro-1H-inden-1-yl]benzenesulfonamide |
| 123 | 4-chloro-N-[1-(hydroxymethyl)cyclohexyl]benzenesulfonamide |
| 124 | 4-chloro-N-[1-(hydroxymethyl)-2,3-dihydro-1H-inden-1-yl]benzenesulfonamide |
| 125 | 4-chloro-N-(1-cyclobutyl-2-hydroxy-1-phenylethyl)benzenesulfonamide |
| 126 | 4-fluoro-N-[(1S,2S)-1-(1-hydroxyethyl)-2-methylbutyl]benzenesulfonamide |
| 127 | N-{(1S,2S)-1-[cyclopentyl(hydroxy)methyl]-2-methylbutyl}-4-fluoro benzenesulfonamide |
| 128 | 4-fluoro-N-{(1S)-2-hydroxy-1-[(1S)-1-methylpropyl]octyl}benzenesulfonamide |
| 129 | 4-fluoro-N-{(1S)-2-hydroxy-1-[(1S)-1-methylpropyl]heptyl}benzenesulfonamide |
| 130 | 4-fluoro-N-{(1S)-2-hydroxy-1-[(1S)-1-methylpropyl]hexyl}benzenesulfonamide |
| 131 | 4-fluoro-N-{(1S,2S)-1-[hydroxy(2-methylphenyl)methyl]-2-methylbutyl}benzenesulfonamide |
| 132 | 4-fluoro-N-{(1S)-2-hydroxy-3,3-dimethyl-1-[(1S)-1-methylpropyl]butyl}benzenesulfonamide |
| 133 | 4-fluoro-N-{(1S)-2-hydroxy-1-[(1S)-1-methylpropyl]-3-butenyl}benzenesulfonamide |
| 134 | 4-fluoro-N-{(1S)-2-hydroxy-1-[(1S)-1-methylpropyl]-4-pentenyl}benzenesulfonamide |
| 135 | 4-fluoro-N-{(1S)-2-hydroxy-1-[(1S)-1-methylpropyl]butyl}benzenesulfonamide |
| 136 | N-{(1S,2S)-1-[(4-chlorophenyl)(hydroxy)methyl]-2-methylbutyl}-4-fluorobenzenesulfonamide |
| 137 | 4-fluoro-N-{(1S)-2-hydroxy-4-methyl-1-[(1S)-1-methylpropyl]-3-pentenyl}benzenesulfonamide |
| 138 | 4-fluoro-N-{(1S)-2-hydroxy-3-methyl-1-[(1S)-1-methylpropyl]-3-butenyl}benzenesulfonamide |
| 139 | 4-fluoro-N-{(1S,2S)-1-[hydroxy(4-methoxyphenyl)methyl]-2-methylbutyl}benzenesulfonamide |
| 140 | N-{(1S)-4-(1,3-dioxan-2-yl)-2-hydroxy-1-[(1S)-1-methylpropyl]butyl}-4-fluorobenzenesulfonamide |
| 141 | 4-fluoro-N-{(1S)-2-hydroxy-1-[(1S)-1-methylpropyl]-5-hexenyl}benzenesulfonamide |
| 142 | 4-fluoro-N-((1S,2S)-1-{hydroxy[4-(methylsulfanyl)phenyl]methyl}-2-methylbutyl)benzenesulfonamide |
| 143 | N-{(1S,2S)-1-[[4-(dimethylamino)phenyl](hydroxy)methyl]-2-methylbutyl}-4-fluorobenzenesulfonamide |
| 144 | 4-fluoro-N-{(1S,2S)-1-[hydroxy(1-naphthyl)methyl]-2-methylbutyl}benzenesulfonamide |
| 145 | 4-bromo-N-[(1S,2S)-1-(1-hydroxyethyl)-2-methylbutyl]benzenesulfonamide |
| 146 | 4-bromo-N-{(1S,2S)-1-[cyclopentyl(hydroxy)methyl]-2-methylbutyl}benzenesulfonamide |
| 147 | 4-bromo-N-{(1S)-2-hydroxy-1-[(1S)-1-methylpropyl]heptyl}benzenesulfonamide |
| 148 | 4-bromo-N-{(1S)-2-hydroxy-1-[(1S)-1-methylpropyl]hexyl}benzenesulfonamide |
| 149 | 4-bromo-N-{(1S)-2-hydroxy-3,3-dimethyl-1-[(1S)-1-methylpropyl]butyl}benzenesulfonamide |
| 150 | 4-bromo-N-{(1S)-2-hydroxy-4-methyl-1-[(1S)-1-methylpropyl]pentyl}benzenesulfonamide |
| 151 | 4-bromo-N-{(1S)-2-hydroxy-1-[(1S)-1-methylpropyl]-3-butenyl}benzenesulfonamide |
| 152 | 4-bromo-N-{(1S)-2-hydroxy-1-[(1S)-1-methylpropyl]-4-pentenyl}benzenesulfonamide |
| 153 | 4-bromo-N-{(1S)-2-hydroxy-1-[(1S)-1-methylpropyl]butyl}benzenesulfonamide |

TABLE 14-continued

| Ex # | Compound |
|---|---|
| 154 | 4-bromo-N-{(1S,2S)-1-[(4-fluorophenyl)(hydroxy)methyl]-2-methylbutyl}benzenesulfonamide |
| 155 | 4-bromo-N-{(1S,2S)-1-[(4-chlorophenyl)(hydroxy)methyl]-2-methylbutyl}benzenesulfonamide |
| 156 | 4-bromo-N-{(1S)-2-hydroxy-4-methyl-1-[(1S)-1-methylpropyl]-3-pentenyl}benzenesulfonamide |
| 157 | 4-bromo-N-{(1S)-2-hydroxy-3-methyl-1-[(1S)-1-methylpropyl]-3-butenyl}benzenesulfonamide |
| 158 | 4-bromo-N-{(1S,2S)-1-[hydroxy(4-methoxyphenyl)methyl]-2-methylbutyl}benzenesulfonamide |
| 159 | 4-bromo-N-{(1S,3E)-2-hydroxy-3-methyl-1-[(1S)-1-methylpropyl]-3-pentenyl}benzenesulfonamide |
| 160 | 4-bromo-N-{(1S)-4-(1,3-dioxan-2-yl)-2-hydroxy-1-[(1S)-1-methylpropyl]butyl}benzenesulfonamide |
| 161 | 4-bromo-N-{(1S)-2-hydroxy-1-[(1S)-1-methylpropyl]-5-hexenyl}benzenesulfonamide |
| 162 | 4-bromo-N-{(1S)-2-hydroxy-1-[(1S)-1-methylpropyl]-3-pentynyl}benzenesulfonamide |
| 163 | 4-bromo-N-((1S,2S)-1-{hydroxy[4-(methylsulfanyl)phenyl]methyl}-2-methylbutyl)benzenesulfonamide |
| 164 | 4-bromo-N-{(1S,2S)-1-[[4-(dimethylamino)phenyl](hydroxy)methyl]-2-methylbutyl}benzenesulfonamide |
| 165A | 4-chloro-N-[(1S,2S)-1-formyl-2-methylbutyl]benzenesulfonamide |
| 165 | 4-chloro-N-[(1S,2S)-1-(1-hydroxyethyl)-2-methylbutyl]benzenesulfonamide |
| 166 | 4-chloro-N-{(1S,2S)-1-[cyclopentyl(hydroxy)methyl]-2-methylbutyl}benzenesulfonamide |
| 167 | 4-chloro-N-{(1S)-2-hydroxy-1-[(1S)-1-methylpropyl]octyl}benzenesulfonamide |
| 168 | 4-chloro-N-{(1S)-2-hydroxy-1-[(1S)-1-methylpropyl]heptyl}benzenesulfonamide |
| 169 | 4-chloro-N-{(1S)-2-hydroxy-1-[(1S)-1-methylpropyl]hexyl}benzenesulfonamide |
| 170 | 4-chloro-N-{(1S)-2-hydroxy-3-methyl-1-[(1S)-1-methylpropyl]butyl}benzenesulfonamide |
| 171 | 4-chloro-N-{(1S,2S)-1-[hydroxy(2-methylphenyl)methyl]-2-methylbutyl}benzenesulfonamide |
| 172 | 4-chloro-N-{(1S)-2-hydroxy-3,3-dimethyl-1-[(1S)-1-methylpropyl]butyl}benzenesulfonamide |
| 173 | 4-chloro-N-{(1S)-2-hydroxy-4-methyl-1-[(1S)-1-methylpropyl]pentyl}benzenesulfonamide |
| 174 | 4-chloro-N-{(1S)-2-hydroxy-1-[(1S)-1-methylpropyl]-3-butenyl}benzenesulfonamide |
| 175 | 4-chloro-N-{(1S)-2-hydroxy-1-[(1S)-1-methylpropyl]-4-pentenyl}benzenesulfonamide |
| 176 | 4-chloro-N-{(1S)-2-hydroxy-1-[(1S)-1-methylpropyl]butyl}benzenesulfonamide |
| 177 | 4-chloro-N-{(1S,2S)-1-[(4-chlorophenyl)(hydroxy)methyl]-2-methylbutyl}benzenesulfonamide |
| 178 | 4-chloro-N-{(1S,2S)-1-[hydroxy(4-methoxyphenyl)methyl]-2-methylbutyl}benzenesulfonamide |
| 179 | 4-chloro-N-{(1S)-4-(1,3-dioxan-2-yl)-2-hydroxy-1-[(1S)-1-methylpropyl]butyl}benzenesulfonamide |
| 180 | 4-chloro-N-{(1S)-2-hydroxy-1-[(1S)-1-methylpropyl]-5-hexenyl}benzenesulfonamide |
| 181 | 4-chloro-N-{(1S)-2-hydroxy-1-[(1S)-1-methylpropyl]-3-pentynyl}benzenesulfonamide |
| 182 | 4-chloro-N-((1S,2S)-1-{hydroxy[4-(methylsulfanyl)phenyl]methyl}-2-methylbutyl)benzenesulfonamide |
| 183 | 4-chloro-N-{(1S,2S)-1-[[4-(dimethylamino)phenyl](hydroxy)methyl]-2-methylbutyl}benzenesulfonamide |
| 184 | 4-chloro-N-{(1S,2S)-1-[hydroxy(1-naphthyl)methyl]-2-methylbutyl}benzenesulfonamide |
| 185 | 3-chloro-N-[(1S,2S)-1-(1-hydroxyethyl)-2-methylbutyl]benzenesulfonamide |
| 186 | 3-chloro-N-{(1S,2S)-1-[cyclopentyl(hydroxy)methyl]-2-methylbutyl}benzenesulfonamide |
| 187 | 3-chloro-N-{(1S)-2-hydroxy-1-[(1S)-1-methylpropyl]octyl} benzenesulfonamide |
| 188 | 3-chloro-N-{(1S)-2-hydroxy-1-[(1S)-1-methylpropyl]heptyl}benzenesulfonamide |
| 189 | 3-chloro-N-{(1S)-2-hydroxy-1-[(1S)-1-methylpropyl]hexyl}benzenesulfonamide |
| 190 | 3-chloro-N-{(1S)-2-hydroxy-3-methyl-1-[(1S)-1-methylpropyl]butyl}benzenesulfonamide |
| 191 | 3-chloro-N-{(1S)-2-hydroxy-3,3-dimethyl-1-[(1S)-1-methylpropyl]butyl}benzenesulfonamide |
| 192 | 3-chloro-N-{(1S)-2-hydroxy-4-methyl-1-[(1S)-1-methylpropyl[pentyl}benzenesulfonamide |
| 193 | 3-chloro-N-{(1S)-2-hydroxy-1-[(1S)-1-methylpropyl]-3-butenyl}benzenesulfonamide |

TABLE 14-continued

| Ex # | Compound |
|---|---|
| 194 | 3-chloro-N-{(1S)-2-hydroxy-1-[(1S)-1-methylpropyl]-4-pentenyl}benzenesulfonamide |
| 195 | 3-chloro-N-{(1S)-2-hydroxy-1-[(1S)-1-methylpropyl]butyl}benzenesulfonamide |
| 196 | 3-chloro-N-{(1S,2S)-1-[(4-chlorophenyl)(hydroxy)methyl]-2-methylbutyl}benzenesulfonamide |
| 197 | 3-chloro-N-{(1S)-2-hydroxy-4-methyl-1-[(1S)-1-methylpropyl]-3-pentenyl}benzenesulfonamide |
| 198 | 3-chloro-N-{(1S,2S)-1-[hydroxy(4-methoxyphenyl)methyl]-2-methylbutyl}benzenesulfonamide |
| 199 | 3-chloro-N-{(1S)-4-(1,3-dioxan-2-yl)-2-hydroxy-1-[(1S)-1-methylpropyl]butyl}benzenesulfonamide |
| 200 | 3-chloro-N-{(1S)-2-hydroxy-1-[(1S)-1-methylpropyl]-5-hexenyl}benzenesulfonamide |
| 201 | 3-chloro-N-((1S,2S)-1-{hydroxy[4-(methylsulfanyl)phenyl]methyl}-2-methylbutyl)benzenesulfonamide |
| 202 | N-{(1S,2S)-1-[cyclopentyl(hydroxy)methyl]-2-methylbutyl}-2-fluorobenzenesulfonamide |
| 203 | 2-fluoro-N-{(1S)-2-hydroxy-1-[(1S)-1-methylpropyl]octyl}benzenesulfonamide |
| 204 | 2-fluoro-N-{(1S)-2-hydroxy-1-[(1S)-1-methylpropyl]heptyl}benzenesulfonamide |
| 205 | 2-fluoro-N-{(1S)-2-hydroxy-1-[(1S)-1-methylpropyl]hexyl} benzenesulfonamide |
| 206 | 2-fluoro-N-{(1S)-2-hydroxy-1-[(1S)-1-methylpropyl]-3-butenyl}benzenesulfonamide |
| 207 | 2-fluoro-N-{(1S,2S)-1-[(4-fluorophenyl)(hydroxy)methyl]-2-methylbutyl}benzenesulfonamide |
| 208 | N-{(1S,2S)-1-[(4-chlorophenyl)(hydroxy)methyl]-2-methylbutyl}-2-fluorobenzenesulfonamide |
| 209 | 2-fluoro-N-{(1S,2S)-1-[hydroxy(4-methoxyphenyl)methyl]-2-methylbutyl}benzenesulfonamide |
| 210 | N-{(1S)-4-(1,3-dioxan-2-yl)-2-hydroxy-1-[(1S)-1-methylpropyl]butyl}-2-fluorobenzenesulfonamide |
| 211 | 4-bromo-N-[(1S,2S)-1-(1-hydroxy-1-methylethyl)-2-methylbutyl]benzenesulfonamide |
| 212 | 4-bromo-N-{(1S)-2-hydroxy-1-[(1S)-1-methylpropyl]-2-pentylheptyl}benzenesulfonamide |
| 213 | 4-bromo-N-{(1S)-2-butyl-2-hydroxy-1-[(1S)-1-methylpropyl]hexyl}benzenesulfonamide |
| 214 | 4-bromo-N-{(1S)-2-hydroxy-2-isobutyl-4-methyl-1-[(1S)-1-methylpropyl]pentyl}benzenesulfonamide |
| 215 | 4-bromo-N-{(1S,2S)-1-[hydroxy(diphenyl)methyl]-2-methylbutyl}benzenesulfonamide |
| 216 | N-{(1S)-2-allyl-2-hydroxy-1-[(1S)-1-methylpropyl]-4-pentenyl}-4-bromobenzenesulfonamide |
| 217 | 4-bromo-N-{(1S)-2-ethyl-2-hydroxy-1-[(1S)-1-methylpropyl]butyl}benzenesulfonamide |
| 218 | N-{(1S,2S)-1-[bis(4-chlorophenyl)(hydroxy)methyl]-2-methylbutyl}-4-bromobenzenesulfonamide |
| 219 | 4-bromo-N-{(1S)-2-hydroxy-2-isopropenyl-3-methyl-1-[(1S)-1-methylpropyl]-3-butenyl}benzenesulfonamide |
| 220 | 4-bromo-N-{(1S,3E)-2-hydroxy-3-methyl-2-[(1E)-1-methyl-1-propenyl]-1-[(1S)-1-methylpropyl]-3-pentenyl}benzenesulfonamide |
| 221 | 4-bromo-N-{(1S)-2-(3-butenyl)-2-hydroxy-1-[(1S)-1-methylpropyl]-5-hexenyl}benzenesulfonamide |
| 222 | 4-bromo-N-((1S,2S)-1-{hydroxy[di(1-naphthyl)]methyl}-2-methylbutyl)benzenesulfonamide |
| 223 | 4-chloro-N-[(1S,2S)-1-(1-hydroxy-1-methylethyl)-2-methylbutyl]benzenesulfonamide |
| 224 | 4-chloro-N-{(1S)-2-hexyl-2-hydroxy-1-[(1S)-1-methylpropyl]octyl}benzenesulfonamide |
| 225 | N-{(1S)-2-butyl-2-hydroxy-1-[(1S)-1-methylpropyl]hexyl}-4-chlorobenzenesulfonamide |
| 226 | 4-chloro-N-{(1S)-2-hydroxy-2-isobutyl-4-methyl-1-[(1S)-1-methylpropyl]pentyl}benzenesulfonamide |
| 227 | 4-chloro-N-{(1S,2S)-1-[hydroxy(diphenyl)methyl]-2-methylbutyl}benzenesulfonamide |
| 228 | N-{(1S)-2-allyl-2-hydroxy-1-[(1S)-1-methylpropyl]-4-pentenyl}-4-chlorobenzenesulfonamide |
| 229 | 4-chloro-N-{(1S)-2-ethyl-2-hydroxy-1-[(1S)-1-methylpropyl]butyl}benzenesulfonamide |
| 230 | 4-chloro-N-{(1S)-2-hydroxy-2-isopropenyl-3-methyl-1-[(1S)-1-methylpropyl]-3-butenyl}benzenesulfonamide |
| 231 | 4-chloro-N-((1S,2S)-1-{hydroxy[bis(4-methoxyphenyl)]methyl}-2-methylbutyl)benzenesulfonamide |
| 232 | 4-chloro-N-{(1S,3E)-2-hydroxy-3-methyl-2-[(1E)-1-methyl-1-propenyl]-1-[(1S)-1-methylpropyl]-3-pentenyl}benzenesulfonamide |
| 233 | N-{(1S)-2-(3-butenyl)-2-hydroxy-1-[(1S)-1-methylpropyl]-5-hexenyl}-4-chlorobenzenesulfonamide |

TABLE 14-continued

| Ex # | Compound |
|---|---|
| 234 | 4-chloro-N-((1S,2S)-1-{hydroxy[di(1-naphthyl)]methyl}-2-methylbutyl) benzenesulfonamide |
| 235 | 4-fluoro-N-[(1S,2S)-1-(1-hydroxy-1-methylethyl)-2-methylbutyl] benzenesulfonamide |
| 236 | 4-fluoro-N-{(1S)-2-hexyl-2-hydroxy-1-[(1S)-1-methylpropyl]octyl} benzenesulfonamide |
| 237 | 4-fluoro-N-{(1S)-2-hydroxy-1-[(1S)-1-methylpropyl]-2-pentylheptyl} benzenesulfonamide |
| 238 | N-{(1S)-2-butyl-2-hydroxy-1-[(1S)-1-methylpropyl]hexyl}-4-fluoro benzenesulfonamide |
| 239 | 4-fluoro-N-{(1S)-2-hydroxy-2-isopropyl-3-methyl-1-[(1S)-1-methylpropyl]butyl}benzenesulfonamide |
| 240 | 4-fluoro-N-{(1S)-2-hydroxy-2-isobutyl-4-methyl-1-[(1S)-1-methylpropyl]pentyl}benzenesulfonamide |
| 241 | N-{(1S)-2-allyl-2-hydroxy-1-[(1S)-1-methylpropyl]-4-pentenyl}-4-fluoro benzenesulfonamide |
| 242 | N-{(1S)-2-ethyl-2-hydroxy-1-[(1S)-1-methylpropyl]butyl}-4-fluoro benzenesulfonamide |
| 243 | 4-fluoro-N-{(1S)-2-hydroxy-2-isopropenyl-3-methyl-1-[(1S)-1-methylpropyl]-3-butenyl}benzenesulfonamide |
| 244 | 4-fluoro-N-((1S,2S)-1-{hydroxy[bis(4-methoxyphenyl)]methyl}-2-methylbutyl)benzenesulfonamide |
| 245 | 4-fluoro-N-{(1S,3E)-2-hydroxy-3-methyl-2-[(1E)-1-methyl-1-propenyl]-1-[(1S)-1-methylpropyl]-3-pentenyl}benzenesulfonamide |
| 246 | N-{(1S)-2-(3-butenyl)-2-hydroxy-1-[(1S)-1-methylpropyl]-5-hexenyl}-4-fluorobenzenesulfonamide |
| 247 | N-{(1S,2S)-1-[bis[4-(dimethylamino)phenyl](hydroxy)methyl]-2-methylbutyl}-4-fluorobenzenesulfonamide |
| 248 | 4-fluoro-N-((1S,2S)-1-{hydroxy[di(1-naphthyl)]methyl}-2-methylbutyl) benzenesulfonamide |
| 249 | 3-chloro-N-{(1S)-2-hexyl-2-hydroxy-1-[(1S)-1-methylpropyl]octyl} benzenesulfonamide |
| 250 | 3-chloro-N-{(1S)-2-hydroxy-1-[(1S)-1-methylpropyl]-2-pentylheptyl} benzenesulfonamide |
| 251 | N-{(1S)-2-butyl-2-hydroxy-1-[(1S)-1-methylpropyl]hexyl}-3-chloro benzenesulfonamide |
| 252 | 3-chloro-N-{(1S)-2-hydroxy-2-isobutyl-4-methyl-1-[(1S)-1-methylpropyl]pentyl}benzenesulfonamide |
| 253 | 3-chloro-N-{(1S,2S)-1-[hydroxy(diphenyl)methyl]-2-methylbutyl} benzenesulfonamide |
| 254 | N-{(1S)-2-allyl-2-hydroxy-1-[(1S)-1-methylpropyl]-4-pentenyl}-3-chloro benzenesulfonamide |
| 255 | 3-chloro-N-{(1S)-2-ethyl-2-hydroxy-1-[(1S)-1-methylpropyl]butyl} benzenesulfonamide |
| 256 | N-{(1S,2S)-1-[bis(4-chlorophenyl)(hydroxy)methyl]-2-methylbutyl}-3-chlorobenzenesulfonamide |
| 257 | 3-chloro-N-{(1S)-2-hydroxy-2-isopropenyl-3-methyl-1-[(1S)-1-methylpropyl]-3-butenyl}benzenesulfonamide |
| 258 | 3-chloro-N-((1S,2S)-1-{hydroxy[bis(4-methoxyphenyl)]methyl}-2-methylbutyl)benzenesulfonamide |
| 259 | 3-chloro-N-{(1S,3E)-2-hydroxy-3-methyl-2-[(1E)-1-methyl-1-propenyl]-1-[(1S)-1-methylpropyl]-3-pentenyl}benzenesulfonamide |
| 260 | N-{(1S)-2-(3-butenyl)-2-hydroxy-1-[(1S)-1-methylpropyl]-5-hexenyl}-3-chlorobenzenesulfonamide |
| 261 | 2-fluoro-N-{(1S)-2-hexyl-2-hydroxy-1-[(1S)-1-methylpropyl]octyl} benzenesulfonamide |
| 262 | 2-fluoro-N-{(1S)-2-hydroxy-1-[(1S)-1-methylpropyl]-2-pentylheptyl} benzenesulfonamide |
| 263 | 2-fluoro-N-{(1S,2S)-1-[hydroxy(diphenyl)methyl]-2-methylbutyl} benzenesulfonamide |
| 264 | N-{(1S)-2-allyl-2-hydroxy-1-[(1S)-1-methylpropyl]-4-pentenyl}-2-fluoro benzenesulfonamide |
| 265 | N-{(1S)-2-ethyl-2-hydroxy-1-[(1S)-1-methylpropyl]butyl}-2-fluoro benzenesulfonamide |
| 266 | N-{(1S,2S)-1-[bis(4-fluorophenyl)(hydroxy)methyl]-2-methylbutyl}-2-fluoro benzenesulfonamide |
| 267 | N-{(1S,2S)-1-[bis(4-chlorophenyl)(hydroxy)methyl]-2-methylbutyl}-2-fluoro benzenesulfonamide |
| 268 | 2-fluoro-N-{(1S)-2-hydroxy-2-isopropenyl-3-methyl-1-[(1S)-1-methylpropyl]-3-butenyl}benzenesulfonamide |
| 269 | 2-fluoro-N-((1S,2S)-1-{hydroxy[bis(4-methoxyphenyl)]methyl}-2-methylbutyl) benzenesulfonamide |
| 270 | 2-fluoro-N-{(1S,3E)-2-hydroxy-3-methyl-2-[(1E)-1-methyl-1-propenyl]-1-[(1S)-1-methylpropyl]-3-pentenyl}benzenesulfonamide |
| 271 | N-{(1S)-2-(3-butenyl)-2-hydroxy-1-[(1S)-1-methylpropyl]-5-hexenyl}-2-fluorobenzenesulfonamide |
| 272 | 4-chloro-N-[(1S)-1-cyclohexyl-2-hydroxyethyl]benzenesulfonamide |

TABLE 14-continued

| Ex # | Compound |
|---|---|
| 273 | 4-chloro-N-[(1S)-2-hydroxy-1-phenylethyl]benzenesulfonamide |
| 274 | 4-chloro-N-[(1S)-1-(hydroxymethyl)-2-methylpropyl]benzenesulfonamide |
| 275 | 4-bromo-N-[(1S)-1-(hydroxymethyl)-2-methylpropyl]benzenesulfonamide |
| 276 | 4-iodo-N-[(1S,2S)-1-(hydroxymethyl)-2-methylbutyl]benzenesulfonamide |
| 277 | 4-chloro-N-[(1S)-1-(hydroxymethyl)-2,2-dimethylpropyl]benzenesulfonamide |

Example 278

Repressor Release Assay (RRA)

The beta amyloid inhibitory activity of the compounds of the present invention was determined using the Repressor Release Assay (RRA). See, Table 17. A compound was considered active in RRA if it leads to at least a 1.5 fold increase in luciferase activity at 10 μg/mL and was non-toxic.

A. Cell Culture

CHO-K1 cells were cultured in whole DMEM media (DMEM—High Glucose with 10% fetal bovine serum, 1% Non-essential Amino Acids, and 1% Penicillin-Streptomycin) at 37° C. with 5% $CO_2$. Two million cells were plated into 10-cm dishes 24 hrs prior to transfection.

Transient transfections were completed as recommended by Gibco BRL using their Lipofectamine Plus system. First, 6 μg of pRSVO-luc and 6 μg of APP-lacI construct DNA were added to 460 μL Opti-Mem transfection media and incubated with 30 μL Plus reagent for 15 minutes. Then, a lipid mixture of 40 μL Lipofectamine reagent and 460 μL Opti-Mem transfection media was incubated with the DNA-Plus reagent mixture for 15 minutes. During the DNA-lipid incubation, the CHO-K1 cells were washed once and covered in 5.0 mL DMEM media without Penicillin-Streptomycin. The DNA-lipid preparation was then layered onto these cells and incubated at 37° C. overnight.

One and one half million transfected cells per well (100 μL total volume) were plated into sterile, opaque Packard 96-well Culture-Plates in clear DMEM whole media (DMEM—without phenol red) and incubated at 37° C. with 5% $CO_2$ for 3-5 hours.

B. Compound Dilution

Compounds were diluted using two different protocols; one protocol was used for compounds supplied neat (weighed powder in vial) and the other protocol was used for compounds supplied in solution (20 mM in DMSO in 96-well plates). For both protocols, 25 mM Hepes and 25 mM Hepes/1% DMSO were prepared fresh to be used as diluent. The Hepes/DMSO was used as the diluent control on all experimental plates.

The following table depicts the steps for compound dilution (please note that the last step was the addition of compound to cells/media in tissue culture plate).

TABLE 15

| | Concentration | Dilution |
|---|---|---|
| Stock Solution | 10 mg/mL | x mg compound (vial) diluted with 100% DMSO |
| Dilution 1 | 1 mg/mL | 20 μL stock solution 180 μL 25 mM Hepes |
| Dilution 2 | 200 μg/mL | 60 μL Dilution 1 240 μL 25 mM Hepes |

TABLE 15-continued

| | Concentration | Dilution |
|---|---|---|
| Dilution 3 (in Cell Plate) | 20 μg/mL | 11.3 μL Dilution 2 (in 100 μL cells/well) |

Because some compounds were present in 96-well format at 20 mM, the following represents the protocol for their dilution (note that an average molecular weight of these compounds was used to calculate these dilutions and as above, the last step was the addition of compound to cells/media in tissue culture plate).

TABLE 16

| | Concentration | Dilution |
|---|---|---|
| Stock Solution (original conc.) | — | 20 mM Solution |
| Dilution 1 | ~200 μg/mL | 6 μL stock solution 194 μL 25 mM Hepes |
| Dilution 2 (in Cell Plate) | ~20 μg/mL | 11.3 μL Dilution 2 (in 100 μL cells/well) |

Once the compounds were diluted, they were applied in duplicate on cells in tissue culture plates (prepared above). Cells were incubated with compound at 37° C. with 5% $CO_2$ for an additional 36-48 hours.

C. Assay Measurement

Luciferase assays (LucLite reagent, Packard) were performed and were read on a Packard TopCount instrument. Media was removed from each 96-well plate and replaced with 100 μL PBS per well (with $Mg^{2+}$ and $Ca^{2+}$). An equal volume (100 μL) of the LucLite lysis/substrate buffer was added to each well and the plates were sealed and mixed in the dark on a rotary shaker for 15-30 minutes at room temperature. Luciferase readings were then taken on the TopCount instrument. Measurements were expressed as relative light units (RLU) and are calculated and analyzed in MS Excel as follows:

D. Analysis of Data

"Fold Increase" refers to the amount of luciferase activity (measured in relative light units) over diluent control. "SEM" refers to the standard error of the mean for fold increase. "Activity": A compound is considered active if it results in at least a 1.5 fold increase in luciferase activity at 10 IM/mL. 1=non-toxic, 0=toxic in Table 17. "Toxicity" is determined by loss of signal (<0.75 fold increase).

E. Standard Beta Amyloid Inhibitor

The reference gamma secretase inhibitor DAPT (LY374973, AN37124: Dovey, H. F. et al, *J. Neurochem.* 76: 173-181 (2001)) was prepared as outlined in WO 98/22494 and tested in RRA and exhibited a 6.0-28.1 fold increase in luciferase activity at 10 μg/mL.

TABLE 17

Repressor Release Assay

| Example | Conc (μg/ml) | APPI Fold Increase | APPI % of Example #98 | (%)APPI Toxicity |
|---|---|---|---|---|
| 91 | 10 | 2.38 | 92.18 | 1 |
|  | 3 | 1.71 | 66.26 | 1 |
|  | 20 | 5 | 116.7 | 1 |
|  | 20 | 3.1 | 81 | 1 |
|  | 20 | 4.4 | 154.8 | 1 |
|  | 20 | 3.8 | 105 | 1 |
|  | 20 | 2 | 46.8 | 1 |
| 98 | 10 | 2.58 | 100 | 1 |
|  | 10 | 2.91 | 112.76 | 1 |
|  | 10 | 3.09 | 100 | 1 |
|  | 10 | 3.26 | 100 | 1 |
|  | 10 | 2.56 | 100 | 1 |
|  | 10 | 2.7 | 100 | 1 |
|  | 10 | 2.62 | 100 | 1 |
|  | 10 | 2.5 | 100 | 1 |
|  | 10 | 2.17 | 100 | 1 |
|  | 10 | 2.92 | 100 | 1 |
|  | 10 | 2.11 | 100 | 1 |
|  | 10 | 2.36 | 100 | 1 |
|  | 10 | 2.06 | 100 | 1 |
|  | 10 | 2.25 | 100 | 1 |
|  | 10 | 2.75 | 100 | 1 |
|  | 10 | 2.52 | 100 | 1 |
|  | 10 | 5.5 | 100 | 1 |
|  | 10 | 3.2 | 100 | 1 |
|  | 10 | 4.3 | 100 | 1 |
|  | 10 | 3.5 | 100 | 1 |
|  | 10 | 3.8 | 100 | 1 |
|  | 20 | 3.7 | 100 | 1 |
|  | 10 | 3.3 | 100 | 1 |
|  | 10 | 2.69 | 100 | 1 |
|  | 20 | 5.6 | 100 | 1 |
|  | 20 | 5.5 | 100 | 1 |
|  | 20 | 5.8 | 100 | 1 |
|  | 20 | 4.4 | 100 | 1 |
|  | 20 | 3.2 | 100 | 1 |
|  | 20 | 2.7 | 100 | 1 |
|  | 20 | 3.3 | 100 | 1 |
|  | 20 | 3.3 | 100 | 1 |
|  | 20 | 3.6 | 100 | 1 |
|  | 20 | 4.4 | 100 | 1 |
|  | 20 | 3.9 | 100 | 1 |
|  | 20 | 3.7 | 100 | 1 |
|  | 20 | 4.2 | 100 | 1 |
|  | 20 | 7 | 100 | 1 |
|  | 20 | 19.5 | 100 | 1 |
|  | 20 | 4.2 | 100 | 1 |
|  | 20 | 5.5 | 100 | 1 |
|  | 20 | 4 | 100 | 1 |
|  | 20 | 3.2 | 100 | 1 |
|  | 20 | 4.4 | 100 | 1 |
|  | 20 | 3.5 | 100 | 1 |
|  | 20 | 4.5 | 100 | 1 |
|  | 20 | 5.7 | 100 | 1 |
|  | 20 | 5.4 | 100 | 1 |
|  | 20 | 3.4 | 100 | 1 |
|  | 20 | 2.9 | 100 | 1 |
|  | 20 | 3.3 | 100 | 1 |
|  | 20 | 3.3 | 100 | 1 |
|  | 20 | 3.2 | 100 | 1 |
|  | 20 | 3.5 | 100 | 1 |
|  | 20 | 4.3 | 100 | 1 |
|  | 20 | 4.3 | 100 | 1 |
|  | 20 | 6.8 | 158.9 | 1 |
|  | 20 | 3.9 | 100 | 1 |
|  | 20 | 4.2 | 100 | 1 |
|  | 20 | 2.7 | 100 | 1 |
|  | 10 | 2.53 | 100 | 1 |
|  | 20 | 3 | 76.7 | 1 |
|  | 10 | 2.9 | 100 | 1 |
|  | 10 | 2.78 | 100 | 1 |
|  | 10 | 2.47 | 95.68 | 1 |
|  | 3 | 1.79 | 69.39 | 1 |
| 274 | 20 | 2.1 | 44.8 | 1 |
|  | 20 | 2.4 | 43.2 | 1 |
| 272 | 20 | 2.3 | 81.3 | 1 |
| 275 | 20 | 2 | 41.9 | 1 |
|  | 20 | 1.8 | 32.5 | 1 |
| 90 | 20 | 1.6 | 54.4 | 1 |
| 276 | 20 | 2 | 46.3 | 1 |
|  | 20 | 2.1 | 73.4 | 1 |
| 277 | 20 | 1.5 | 53.4 | 1 |
| 1 | 20 | 1.6 | 27.2 | 1 |
| 2 | 20 | 2.8 | 48.1 | 1 |
| 3 | 20 | 3.6 | 62.9 | 1 |
| 4 | 20 | 1.5 | 26.5 | 1 |
| 5 | 20 | 2.5 | 43.2 | 1 |
| 6 | 20 | 1.7 | 30.2 | 1 |
| 7 | 20 | 1.6 | 27.1 | 1 |
| 8 | 20 | 2 | 35.3 | 1 |
| 9 | 10 | 2.2 | 63.5 | 1 |
|  | 20 | 1.8 | 30.5 | 1 |
| 10 | 20 | 2.4 | 62.5 | 1 |
|  | 20 | 3.6 | 63.2 | 1 |
| 10 | 20 | 3.3 | 113.6 | 1 |
| 11 | 20 | 2.3 | 63.2 | 1 |
| 12 | 20 | 2.9 | 54 | 1 |
| 13 | 20 | 1.8 | 33.5 | 1 |
| 15 | 20 | 1.5 | 26.5 | 1 |
| 16 | 20 | 2.7 | 68.5 | 1 |
| 17 | 20 | 2.2 | 56.4 | 1 |
| 18 | 20 | 1.9 | 48.6 | 1 |
|  | 20 | 1.7 | 41.8 | 1 |
| 19 | 20 | 1.6 | 40.5 | 1 |
| 273 | 20 | 1.5 | 38.7 | 1 |
| 14 | 20 | 1.9 | 67 | 1 |
| 20 | 20 | 3.3 | 78.2 | 1 |
| 21 | 20 | 1.6 | 37.2 | 1 |
| 22 | 20 | 1.7 | 39.5 | 1 |
| 23 | 10 | 3.6 | 116.23 | 1 |
|  | 20 | 8.3 | 197.5 | 1 |
|  | 3 | 1.67 | 54.13 | 1 |
| 24 | 20 | 1.6 | 38.6 | 1 |
| 25 | 20 | 1.8 | 44.1 | 1 |
| 26 | 20 | 2.4 | 58 | 1 |
| 27 | 20 | 2.2 | 53.6 | 1 |
| 28 | 20 | 1.5 | 34.8 | 1 |
| 29 | 20 | 2.1 | 49.5 | 1 |
| 30 | 20 | 2.1 | 50.5 | 1 |
| 31 | 20 | 2.8 | 66.7 | 1 |
| 32 | 20 | 2.2 | 51.6 | 1 |
| 33 | 20 | 3.9 | 112 | 1 |
| 34 | 20 | 4.2 | 122.5 | 1 |
| 35 | 20 | 2.4 | 68.1 | 1 |
| 36 | 10 | 3.33 | 107.5 | 1 |
|  | 20 | 6.4 | 186.2 | 1 |
|  | 20 | 4.5 | 107 | 1 |
|  | 1 | 1.6 | 51.68 | 1 |
|  | 3 | 2.05 | 66.34 | 1 |
| 37 | 20 | 4.7 | 136.5 | 1 |
| 38 | 20 | 3.3 | 94.8 | 1 |
| 39 | 10 | 2.47 | 79.99 | 1 |
|  | 20 | 5.5 | 158.9 | 1 |
|  | 3 | 1.56 | 50.53 | 1 |
| 92 | 20 | 1.7 | 43.2 | 1 |
| 99 | 20 | 1.7 | 42.9 | 1 |
| 93 | 20 | 1.5 | 39.2 | 1 |
| 100 | 20 | 1.6 | 41 | 1 |
| 101 | 20 | 1.6 | 42 | 1 |
| 102 | 20 | 1.5 | 39.6 | 1 |
| 94 | 20 | 2.5 | 69.2 | 1 |
|  | 20 | 1.7 | 38 | 1 |
| 104 | 20 | 1.5 | 31.2 | 1 |
| 103 | 20 | 2.6 | 70.8 | 1 |
|  | 20 | 1.5 | 34.9 | 1 |
| 95 | 20 | 1.6 | 36.3 | 1 |
| 96 | 20 | 1.5 | 44.7 | 1 |

TABLE 17-continued

Repressor Release Assay

| Example | Conc (µg/ml) | APPI Fold Increase | APPI % of Example #98 | (%)APPI Toxicity |
|---|---|---|---|---|
| 106 | 20 | 1.6 | 32.8 | 1 |
| 107 | 1 | 2.35 | 91.1 | 1 |
| 105 | 10 | 1.54 | 47.3 | 1 |
| 108 | 3 | 1.66 | 59.78 | 1 |
| 112 | 20 | 1.8 | 50.3 | 1 |
| 113 | 20 | 1.6 | 43.9 | 1 |
| 109 | 20 | 1.9 | 52.6 | 1 |
| 110 | 20 | 1.7 | 46.5 | 1 |
| 111 | 20 | 1.7 | 47.8 | 1 |
| 116 | 20 | 1.6 | 44.8 | 1 |
| 114 | 20 | 1.5 | 30.9 | 1 |
| 117 | 20 | 1.5 | 31 | 1 |
| 115 | 20 | 1.8 | 37.3 | 1 |
| 118 | 20 | 1.6 | 33.6 | 1 |
| 119 | 20 | 1.5 | 46.5 | 1 |
| 227 | 10 | 1.65 | 75.91 | 1 |
| 165 | 10 | 2.05 | 70.81 | 1 |
|  | 10 | 1.6 | 63.92 | 1 |
| 97 | 20 | 1.5 | 47.3 | 1 |
| 126 | 10 | 1.52 | 59.52 | 1 |
|  | 3 | 1.54 | 56.2 | 1 |
| 127 | 10 | 2.97 | 116.04 | 1 |
| 128 | 10 | 10.76 | 420.7 | 1 |
|  | 10 | 2.13 | 77.43 | 1 |
| 129 | 10 | 7.12 | 278.35 | 1 |
|  | 10 | 1.62 | 59.13 | 1 |
| 130 | 10 | 2.4 | 93.87 | 1 |
| 131 | 10 | 1.65 | 64.57 | 1 |
| 132 | 10 | 1.54 | 60.21 | 1 |
| 133 | 10 | 1.79 | 79.67 | 1 |
| 134 | 10 | 3 | 133.7 | 1 |
|  | 10 | 2.6 | 47 | 1 |
|  | 3 | 1.5 | 27.5 | 1 |
| 135 | 10 | 1.91 | 84.91 | 1 |
|  | 10 | 2 | 37 | 1 |
| 136 | 10 | 3.04 | 135.09 | 1 |
| 137 | 10 | 1.61 | 71.59 | 1 |
| 138 | 10 | 1.57 | 69.78 | 1 |
| 139 | 10 | 2.12 | 94.48 | 1 |
| 140 | 10 | 1.52 | 67.81 | 1 |
| 141 | 10 | 1.79 | 76.02 | 1 |
| 142 | 10 | 2.71 | 114.62 | 1 |
| 143 | 10 | 5.72 | 242.28 | 1 |
| 144 | 10 | 1.69 | 71.37 | 1 |
| 145 | 10 | 3.9 | 152.49 | 1 |
|  | 10 | 2.57 | 102.15 | 1 |
| 146 | 10 | 4.26 | 166.6 | 1 |
|  | 3 | 1.53 | 60.66 | 1 |
|  | 10 | 2.33 | 92.64 | 1 |
| 147 | 10 | 1.94 | 75.86 | 1 |
| 148 | 10 | 1.88 | 73.4 | 1 |
| 149 | 10 | 4.29 | 167.71 | 1 |
|  | 10 | 2.02 | 80.24 | 1 |
| 150 | 10 | 3.39 | 132.65 | 1 |
|  | 10 | 1.59 | 63.18 | 1 |
| 151 | 10 | 2.9 | 129.13 | 1 |
| 152 | 10 | 6.64 | 295.59 | 1 |
|  | 10 | 3.7 | 67.7 | 1 |
|  | 3 | 1.6 | 29.7 | 1 |
| 153 | 10 | 4.77 | 212.3 | 1 |
|  | 3 | 2 | 36.2 | 1 |
|  | 10 | 2.9 | 53.4 | 1 |
| 154 | 10 | 1.68 | 74.73 | 1 |
| 155 | 10 | 4.37 | 194.25 | 1 |
| 156 | 10 | 2.01 | 89.37 | 1 |
|  | 10 | 1.64 | 106.77 | 1 |
|  | 3 | 1.52 | 98.84 | 1 |
| 157 | 10 | 1.96 | 87.36 | 1 |
| 158 | 10 | 2.28 | 101.49 | 1 |
| 159 | 10 | 2.11 | 94.03 | 1 |
| 160 | 10 | 1.66 | 73.83 | 1 |
| 161 | 10 | 1.69 | 71.57 | 1 |
| 162 | 10 | 1.63 | 68.85 | 1 |
| 163 | 10 | 1.64 | 69.41 | 1 |
| 164 | 10 | 3.53 | 149.31 | 1 |
| 166 | 10 | 5.49 | 189.28 | 1 |
|  | 10 | 2.05 | 82.01 | 1 |
| 167 | 10 | 9.66 | 332.83 | 1 |
| 168 | 10 | 8.32 | 286.71 | 1 |
|  | 10 | 2.2 | 87.86 | 1 |
| 169 | 10 | 2.85 | 98.28 | 1 |
|  | 10 | 2.01 | 80.19 | 1 |
| 170 | 10 | 1.92 | 66.13 | 1 |
| 171 | 10 | 1.54 | 53.17 | 1 |
| 172 | 10 | 2.51 | 86.45 | 1 |
|  | 10 | 1.59 | 63.78 | 1 |
| 173 | 10 | 2.56 | 88.08 | 1 |
| 174 | 10 | 2.1 | 102.08 | 1 |
| 175 | 10 | 4.24 | 205.87 | 1 |
|  | 10 | 2.01 | 124.61 | 1 |
| 176 | 10 | 2.63 | 127.84 | 1 |
|  | 10 | 1.87 | 116.42 | 1 |
| 177 | 10 | 1.95 | 94.93 | 1 |
| 178 | 10 | 1.68 | 81.88 | 1 |
| 179 | 10 | 1.63 | 79.4 | 1 |
| 180 | 10 | 1.69 | 80.17 | 1 |
| 181 | 10 | 1.76 | 83.43 | 1 |
| 182 | 10 | 2.58 | 122.24 | 1 |
| 183 | 10 | 4.49 | 212.53 | 1 |
| 184 | 10 | 1.7 | 80.39 | 1 |
| 185 | 10 | 1.51 | 51.91 | 1 |
| 186 | 10 | 3.86 | 133.06 | 1 |
| 187 | 10 | 9.02 | 310.99 | 1 |
| 188 | 10 | 3.54 | 122.17 | 1 |
| 189 | 10 | 1.51 | 52.11 | 1 |
| 190 | 10 | 1.76 | 60.57 | 1 |
| 191 | 10 | 2.42 | 83.48 | 1 |
| 192 | 10 | 2.21 | 76.01 | 1 |
| 193 | 10 | 1.78 | 86.66 | 1 |
| 194 | 10 | 3.42 | 166.42 | 1 |
|  | 10 | 1.97 | 122.18 | 1 |
| 195 | 10 | 2.16 | 104.89 | 1 |
| 196 | 10 | 1.78 | 86.69 | 1 |
| 197 | 10 | 1.54 | 74.67 | 1 |
| 198 | 10 | 1.54 | 74.68 | 1 |
| 199 | 10 | 1.61 | 78.5 | 1 |
| 200 | 10 | 1.85 | 87.52 | 1 |
| 201 | 10 | 2.45 | 116.18 | 1 |
| 202 | 10 | 1.62 | 55.79 | 1 |
| 203 | 10 | 3.47 | 119.61 | 1 |
| 204 | 10 | 3.73 | 128.72 | 1 |
| 205 | 10 | 1.72 | 59.11 | 1 |
| 206 | 10 | 1.9 | 92.42 | 1 |
| 207 | 10 | 1.81 | 87.79 | 1 |
| 208 | 10 | 2.01 | 97.83 | 1 |
| 209 | 10 | 1.81 | 88.04 | 1 |
| 210 | 10 | 1.68 | 81.7 | 1 |
| 211 | 10 | 2.09 | 71.66 | 1 |
| 212 | 10 | 4.85 | 166.42 | 1 |
|  | 10 | 2.4 | 70.1 | 1 |
| 213 | 10 | 3.03 | 103.82 | 1 |
|  | 10 | 1.6 | 46.4 | 1 |
| 214 | 10 | 4.93 | 169.16 | 1 |
|  | 10 | 1.8 | 53.2 | 1 |
| 215 | 10 | 1.65 | 75.81 | 1 |
| 216 | 10 | 1.58 | 72.76 | 1 |
| 217 | 10 | 1.68 | 77.38 | 1 |
| 218 | 10 | 1.55 | 71.25 | 1 |
| 219 | 10 | 1.8 | 82.73 | 1 |
|  | 20 | 2.8 | 75.9 | 1 |
| 220 | 10 | 3.29 | 151.23 | 1 |
| 221 | 10 | 5.73 | 263.29 | 1 |
| 222 | 10 | 1.59 | 54.46 | 1 |
| 223 | 10 | 2.33 | 79.87 | 1 |
| 224 | 10 | 2.22 | 76.16 | 1 |
| 225 | 10 | 6.82 | 234.08 | 1 |
| 226 | 10 | 4.6 | 157.69 | 1 |
| 228 | 10 | 1.56 | 71.57 | 1 |

TABLE 17-continued

Repressor Release Assay

| Example | Conc (µg/ml) | APPI Fold Increase | APPI % of Example #98 | (%)APPI Toxicity |
|---|---|---|---|---|
| 229 | 10 | 1.52 | 69.7 | 1 |
| 230 | 10 | 1.75 | 80.53 | 1 |
|  | 20 | 1.9 | 51 | 1 |
| 231 | 10 | 2.49 | 114.39 | 1 |
| 232 | 10 | 1.94 | 89.04 | 1 |
|  | 20 | 4.2 | 115 | 1 |
| 233 | 10 | 6.67 | 306.66 | 1 |
| 234 | 10 | 2.9 | 99.47 | 1 |
|  | 10 | 1.6 | 49.5 | 1 |
| 235 | 10 | 1.88 | 64.32 | 1 |
| 236 | 10 | 6.55 | 224.57 | 1 |
|  | 10 | 3.2 | 101.3 | 1 |
| 237 | 10 | 6.05 | 207.45 | 1 |
|  | 10 | 3.8 | 119.8 | 1 |
| 238 | 10 | 4.5 | 154.18 | 1 |
| 239 | 10 | 1.54 | 52.99 | 1 |
| 240 | 10 | 3.82 | 131.15 | 1 |
| 241 | 10 | 1.58 | 72.82 | 1 |
| 242 | 10 | 1.6 | 73.53 | 1 |
| 243 | 10 | 1.7 | 78.07 | 1 |
| 244 | 10 | 1.51 | 69.29 | 1 |
| 245 | 10 | 2.05 | 94.29 | 1 |
|  | 20 | 3.5 | 95.1 | 1 |
| 246 | 10 | 2.42 | 111.39 | 1 |
|  | 20 | 1.9 | 50.9 | 1 |
| 247 | 10 | 1.54 | 57.33 | 1 |
| 248 | 10 | 3.53 | 121.19 | 1 |
|  | 10 | 1.5 | 46.6 | 1 |
| 249 | 10 | 1.9 | 58.4 | 1 |
| 250 | 10 | 2.4 | 72.2 | 1 |
| 251 | 10 | 3.4 | 103.5 | 1 |
| 252 | 10 | 1.8 | 53.8 | 1 |
| 253 | 10 | 1.61 | 59.95 | 1 |
| 254 | 10 | 1.93 | 71.92 | 1 |
| 255 | 10 | 2.03 | 75.56 | 1 |
| 256 | 10 | 1.5 | 55.91 | 1 |
| 257 | 10 | 2.54 | 94.5 | 1 |
|  | 20 | 2.5 | 68.8 | 1 |
| 258 | 10 | 1.72 | 63.9 | 1 |
| 259 | 10 | 2.19 | 81.37 | 1 |
|  | 1 | 1.7 | 31.1 | 1 |
|  | 0.3 | 1.7 | 31.1 | 1 |
|  | 3 | 1.7 | 31.5 | 1 |
|  | 10 | 1.6 | 49.1 | 1 |
|  | 20 | 4.4 | 119.7 | 1 |
|  | 10 | 1.7 | 31.6 | 1 |
| 260 | 10 | 6.23 | 231.76 | 1 |
|  | 3 | 1.5 | 26.7 | 1 |
| 261 | 10 | 3.5 | 104.4 | 1 |
| 262 | 10 | 2.2 | 63.8 | 1 |
| 263 | 10 | 1.57 | 58.4 | 1 |
| 264 | 10 | 2 | 74.18 | 1 |
| 265 | 10 | 1.78 | 66.02 | 1 |
| 266 | 10 | 1.57 | 58.25 | 1 |
| 267 | 10 | 1.59 | 58.97 | 1 |
| 268 | 10 | 1.75 | 65.06 | 1 |
| 269 | 10 | 1.58 | 58.74 | 1 |
| 270 | 10 | 1.86 | 69.21 | 1 |
| 271 | 10 | 1.82 | 67.61 | 1 |
| 40 | 20 | 3.4 | 126.2 | 1 |
| 41 | 20 | 4.9 | 182.1 | 1 |
| 42 | 20 | 1.9 | 71.7 | 1 |
| 43 | 20 | 5.1 | 190 | 1 |
| 44 | 20 | 2.6 | 95.7 | 1 |
| 45 | 20 | 1.5 | 55.9 | 1 |
| 46 | 20 | 1.8 | 67.4 | 1 |
| 47 | 20 | 2.4 | 88.9 | 1 |
| 48 | 20 | 3.1 | 116.6 | 1 |
| 120 | 20 | 5 | 135.2 | 1 |
| 121 | 20 | 1.7 | 45.1 | 1 |
| 122 | 20 | 1.5 | 42.1 | 1 |
| 123 | 20 | 4.4 | 121 | 1 |
|  | 20 | 3.5 | 97.4 | 1 |
| 124 | 20 | 2 | 55.1 | 1 |
| 125 | 20 | 1.8 | 49.2 | 1 |
| 49 | 20 | 2.5 | 59.1 | 1 |
| 50 | 20 | 2.5 | 59.3 | 1 |
| 51 | 20 | 1.6 | 37.6 | 1 |
| 52 | 20 | 6.2 | 145.7 | 1 |
|  | 20 | 8.6 | 43.8 | 1 |
| 53 | 20 | 5.2 | 121.9 | 1 |
| 54 | 20 | 5 | 117 | 1 |
| 55 | 20 | 5.6 | 131.5 | 1 |
| 56 | 20 | 3.6 | 85.4 | 1 |
| 57 | 20 | 1.7 | 39.1 | 1 |
| 58 | 20 | 2.6 | 61.2 | 1 |
| 59 | 20 | 3.2 | 76.3 | 1 |
| 60 | 20 | 4.6 | 109.3 | 1 |
| 61 | 20 | 6.5 | 152.3 | 1 |
| 62 | 20 | 1.8 | 42.2 | 1 |
| 63 | 20 | 2 | 47.9 | 1 |
| 64 | 20 | 1.7 | 39.3 | 1 |
| 65 | 20 | 1.9 | 44.6 | 1 |
| 66 | 20 | 5.5 | 129.1 | 1 |
| 67 | 20 | 3.9 | 91.5 | 1 |
| 68 | 20 | 2 | 47.5 | 1 |
| 69 | 20 | 3.1 | 73 | 1 |
| 70 | 20 | 2 | 48 | 1 |
| 71 | 20 | 1.9 | 43.9 | 1 |
| 72 | 20 | 3.2 | 76.4 | 1 |
| 73 | 20 | 5.4 | 127.1 | 1 |
| 74 | 20 | 2.5 | 57.7 | 1 |
| 75 | 20 | 4.8 | 112.3 | 1 |
| 76 | 20 | 5.8 | 135.2 | 1 |
| 77 | 20 | 5.9 | 139.8 | 1 |
| 78 | 20 | 4.4 | 102.4 | 1 |
| 79 | 20 | 1.5 | 34.1 | 1 |
| 80 | 20 | 3.9 | 91.1 | 1 |
| 81 | 20 | 5 | 118 | 1 |
| 82 | 20 | 2.6 | 66 | 1 |
| 83 | 20 | 3.4 | 86.8 | 1 |
| 84 | 20 | 3.4 | 86.6 | 1 |
| 85 | 20 | 3.4 | 87.3 | 1 |
| 86 | 20 | 1.6 | 41.4 | 1 |
| 87 | 20 | 8.8 | 223.8 | 1 |
| 88 | 20 | 6.4 | 27.9 | 1 |
| 89 | 20 | 22.4 | 97.9 | 1 |

All publications cited in this specification are incorporated herein by reference. While the invention has been described with reference to a particularly preferred embodiment, it will be appreciated that modifications can be made without departing from the spirit of the invention. Such modifications are intended to fall within the scope of the appended claims.

What is claimed is:

1. A compound of Formula Ia:

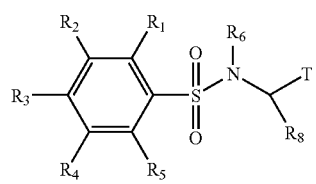

Ia wherein:
$R_1$ is selected from the group consisting of H, halogen, and O;

R₂ is selected from the group consisting of H, halogen, and N=N;
R₃ is selected from the group consisting of H and halogen;
R₄ is selected from the group consisting of H, halogen, amino, and N=N;
R₅ is selected from the group consisting of H, halogen, methoxy, methyl, and O;
R₆ is selected from the group consisting of H, lower alkyl, lower alkenyl, 3-phenyl-2-propyn-1-yl, benzyl, substituted benzyl, CH₂ cycloalkyl, CH₂-2-furan, (CH₂)₂SCH₃, and (CH₂)₂NHBOC;
R₈ is selected from the group consisting of a lower alkyl of S-stereochemistry at the carbon atom to which N and T are attached, cycloalkyl, CH₂ cycloalkyl, CH(lower alkyl)-2-furan, CH(lower alkyl)-4-methoxyphenyl, CH(lower alkyl)phenyl, CH(OH)-4-SCH₃-phenyl, and (CH₂)₂-S-lower alkyl;
T is

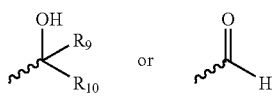

R₉ and R₁₀ are H; or
R₉ is H and R₁₀ is selected from the group consisting of lower alkyl, lower alkenyl, CF₃, methyl-substituted alkenyl, lower alkynyl, cycloalkyl, substituted phenyl, 1-naphthyl, and CH₂CH₂-1,3-dioxolane; or
R₉ and R₁₀ are independently selected from the group consisting of lower alkyl, lower alkenyl, phenyl, 4-substituted-phenyl, and 1-naphthyl;
wherein:
(i) when R₅ is a methoxy; R₂ is halogen and R₁, R₃, and R₄ are H;
(ii) when R₅ is a methyl; R₁ is halogen and R₂, R₃, and R₄ are H;
(iii) when R₄ is an amino; R₃ is halogen and R₁, R₂, and R₅ are H;
(iv) when R₂ is N=N, R₁ is O and R₂ is bound to R₁ to form a heterocyclic ring;
(v) when R₄ is N=N, R₅ is O and R₄ is bound to R₅ to form a heterocyclic ring;
(vi) one or more of R₁ to R₅ is a halogen;
(vii) when R₃ is halogen, R₈ is butyl and R₉ and R₁₀ are H, at least one of R₁, R₂, R₄, and R₅ is not H; and
(viii) when R₃ is halogen, R₈ is butyl and T is —C=O, at least one of R₁, R₂, R₄, and R₅ is not H;
or a pharmaceutically acceptable salt, hydrate, or prodrug thereof.

2. The compound according to claim 1, wherein:
T is:

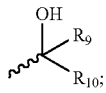

R₁, R₂, R₄, R₅, R₆, R₉, and R₁₀ are H;
R₃ is halogen; and
R₈ is lower alkyl of S-stereochemistry at the carbon atom to which N and T, are attached.

3. The compound according to claim 1, wherein said pharmaceutically acceptable salt of said compound is selected from the group consisting of salts of sodium hydroxide, potassium hydroxide, calcium hydroxide, magnesium hydroxide, diethanolamine, ethylene amine, salts of bases, and mixtures thereof.

4. A compound selected from the group consisting of 2-bromo-N-[(1S,2S)-1- (hydroxymethyl)-2-methylbutyl]benzenesulfonamide, 3-bromo-N-[(1S,2S)-1- (hydroxymethyl)-2-methylbutyl]benzenesulfonamide, 3-chloro-N-[(1S,2S)-1-(hydroxymethyl)-2-methylbutyl] benzenesulfonamide, 4-chloro-N-[(1S,2S)-1-(hydroxymethyl)-2-methylbutyl]-1,2,3-benzoxadiazole-7-sulfonamide, 2-chloro-4-fluoro- N-[(1S,2S)-1-(hydroxymethyl)-2-methylbutyl]benzenesulfonamide, 5-chloro-N-[(1S,2S)- 1-(hydroxymethyl)-2-methylbutyl]-2-methoxybenzenesulfonamide, 2-chloro-N-[(1S,2S)-1-(hydroxymethyl)-2-methylbutyl]-6-methylbenzenesulfonamide, 3,5-dichloro-N- [(1S,2S)-1-(hydroxymethyl)-2-methylbutyl]benzenesulfonamide, 2,4-difluoro-N- [(1S,2S)-1-(hydroxymethyl)-2-methylbutyl] benzenesulfonamide, 4-fluoro-N-[(1S,2S)-1-(hydroxymethyl)-2-methylbutyl]benzenesulfonamide, 2-fluoro-N-[(1S,2S)-1- (hydroxymethyl)-2-methylbutyl]benzenesulfonamide, N-[(1S,2S)-1-(hydroxymethyl)-2-methylbutyl]naphthalene-1-sulfonamide, N-[(1S,2S)-1-(hydroxymethyl)-2- methylbutyl]naphthalene-2-sulfonamide 3-amino-4-chloro-N-[(1S,2S)-1- (hydroxymethyl)-2-methylbutyl]benzenesulfonamide, N-[(1S)-1-benzyl-2-hydroxyethyl]- 4-bromobenzenesulfonamide, 4-bromo-N-[(1S)-1-cyclohexyl-2- hydroxyethyl]benzenesulfonamide, 4-bromo-N-[(1R)-2-hydroxy-1-(4- hydroxyphenyl)ethyl] benzenesulfonamide, 4-bromo-N-[(1S)-1-(hydroxymethyl)-3- methylbutyl]benzenesulfonamide, 4-bromo-N-[(1S)-2-hydroxy-1-(1H-indol-2- ylmethyl)ethyl] benzenesulfonamide, 4-bromo-2,5-difluoro-N-[(1S,2S)-1-(hydroxymethyl-2-methylbutyl]benzenesulfonamide, 2,5-dibromo-N-[(1S,2S)-1- (hydroxymethyl)-2-methylbutyl]benzenesulfonamide, 3,4-dibromo-N-[(1S,2S)-1- (hydroxymethyl)-2-methylbutyl]benzenesulfonamide, 2,3-dichloro-N-[(1S,2S)-1- (hydroxymethyl)-2-methylbutyl]benzenesulfonamide, 3,4-dichloro-N-[(1S,2S)-1-(hydroxymethyl)-2-methylbutyl]benzenesulfonamide, 2,4,5-trichloro-N-[(1S,2S)-1- (hydroxymethyl)-2-methylbutyl]benzenesulfonamide, 4-bromo-2,5-difluoro-N-[(1S)-1- (hydroxymethyl)-2-methylpropyl]benzenesulfonamide, 3,4-dichloro-N-[(1S)-1- (hydroxymethyl)-2-methylpropyl]benzenesulfonamide, 2,4,6-trichloro-N-[(1S)-1-(hydroxymethyl)-2-methylpropyl]benzenesulfonamide, 3,4-dibromo-N-[(1S)-1- (hydroxymethyl)-2,2-dimethylpropyl]benzenesulfonamide, 3,4-dichloro-N-[(1S)-1- (hydroxymethyl)-2,2-dimethylpropyl]benzenesulfonamide, 2,4,5-trichloro-N-[(1S)-1- (hydroxymethyl)-2,2-dimethylpropyl]benzenesulfonamide 2,4,6-trichloro-N-[(1S)-1-(hydroxymethyl)-2,2-dimethylpropyl]benzenesulfonamide, 4-bromo-N-[(1R,2R)-1- (hydroxymethyl)-2-methylbutyl]benzenesulfonamide, 4-bromo-N-[(1S)-1- (hydroxymethyl)-1,2-dimethylpropyl]benzenesulfonamide, 4-bromo-N-[1- (hydroxymethyl)-2-phenylpropyl]benzenesulfonamide, 4-bromo-N-[(1S,2R)-1-(hydroxymethyl)-2-methylbutyl]benzenesulfonamide, 4-chloro-N-[(1S)-1- (hydroxymethyl)-1,2-dimethylpropyl] benzenesulfonamide, 4-chloro-N-[1- (hydroxymethyl)-2-phenylpropyl]benzenesulfonamide, 4-chloro-N-[(1S,2R)-1-(hydroxymethyl)-2-methylbutyl]benzenesulfonamide, N-allyl-4-chloro-N-[(1S,2S)-1-(hydroxymethyl)-2-methylbutyl]benzenesulfonamide, N-([1,1'-biphenyl]-4-ylmethyl)-4-chloro-N-[(1S,2S)-1-(hydroxymethyl)-2-methylbutyl]benzenesulfonamide, tert-butyl 2- {[(4-chlorophenyl)sulfonyl][(1S,2S)-1-(hydroxymethyl)-2- methylbutyl]amino}ethylcarbamate, 4-chloro-N-(4-chlorobenzyl)-N-[(1S,2S)-1-(hydroxymethyl)-2-methylbutyl]benzenesulfonamide, 4-chloro-N-(cyclobutylmethyl)-N- [(1S,2S)-1-(hydroxymethyl)-2-methylbutyl]benzenesulfonamide, 4-chloro-N-(3, 4- dimethoxybenzyl)-N-[(1S,2S)-1-(hydroxymethyl)-2-methylbutyl]benzenesulfonamide, 4- chloro-N-(2-furylmethyl)-N-[(1S,2S)-1-(hydroxymethyl)-2-methylbutyl]benzenesulfonamide, 4-chloro-N-[(1S,2S)-1-(hydroxymethyl)-2-methylbutyl]-N-[2- (methylthio)ethyl]benzenesulfonamide, 4-chloro-N-[(1S,2S)-1-(hydroxymethyl)-2- methylbutyl]-N-(3-phenylprop-2-ynyl)benzenesulfonamide, 4-chloro-N-[(1S,2R)-1-(hydroxymethyl)-2-(4-methoxyphenyl)propyl]benzenesulfonamide, 4-chloro-N-[(1S,2R)- 1-(hydroxymethyl)-2-methyloctyl]benzenesulfonamide, 4-chloro-N-[(1S,2R)-1-(hydroxymethyl)-2-phenylpropyl]benzenesulfonamide, 4-chloro-N-[(1S)-2-ethyl-1- (hydroxymethyl)butyl]benzenesulfonamide, 4-chloro-N-[(1S,2R)-2-ethyl-1- (hydroxymethyl)-4-methylpentyl]benzenesulfonamide, 4-chloro-N-[(1S,2S)-1- (hydroxymethyl)-2-methylpentyl]benzenesulfonamide, 4-chloro-N-[(1S,2S)-2-ethyl-1-(hydroxymethyl)pentyl]benzenesulfonamide, 4-chloro-N-[(1S,2R)-1-(hydroxymethyl)-4- methyl-2-propylpentyl]benzenesulfonamide, 4-chloro-N-[(1S,2R)-1-(hydroxymethyl)-2- (4-methoxyphenyl)pentyl]benzenesulfonamide, 4-chloro-N-[(1S,2R)-1-(hydroxymethyl)- 2-propyloctyl]benzenesulfonamide, 4-chloro-N-[(1S,2R)-1-(hydroxymethyl)-2- phenylpentyl]benzenesulfonamide, 4-chloro-N-[(1S,2S)-1-(hydroxymethyl)-2- methylheptyl]benzenesulfonamide, 4-chloro-N-[(1S,2S)-2-ethyl-1-(hydroxymethyl) heptyl]benzenesulfonamide, 4-chloro-N-[(1S,2R)-1-(hydroxymethyl)-2-pentyloctyl]benzenesulfonamide, 4-chloro-N-[(1S,2S)-1-(hydroxymethyl)-2-phenylpropyl]benzenesulfonamide, 4-chloro-N-[(1S,2S)-1-(hydroxymethyl)-4-methyl-2-phenylpentyl]benzenesulfonamide, 4-chloro-N-[(1S,2S)-1-(hydroxymethyl)-2-phenyloctyl]benzenesulfonamide, 4-chloro-N-[(1S,2R)-2-(2-furyl)-1-(hydroxymethyl)butyl]benzenesulfonamide, 4-chloro-N-[(1S,2R)-2-(2-furyl)-1-(hydroxymethyl)-4- methylpentyl]benzenesulfonamide, 4-chloro-N-[(1S,2R)-2-(2-furyl)-1-(hydroxymethyl)octyl]benzenesulfonamide, 4-chloro-N-[(1S,2S)-1-(hydroxymethyl)- 2,3-dimethylbutyl]benzenesulfonamide, 4-chloro-N-[(1S,2S)-1-(hydroxymethyl)-2-isopropyloctyl]benzenesulfonamide, 4-bromo-N-[(1S,2R)-1-(hydroxymethyl)-2-(4- methoxyphenyl)propyl]benzenesulfonamide, 4-bromo-N-[(1S,2R)-1-(hydroxymethyl)-2-methyloctyl]benzenesulfonamide, 4-bromo-N-[(1S,2R)-2-ethyl-1-(hydroxymethyl)-4- methylpentyl]benzenesulfonamide, 4-bromo-N-[(1S,2R)-1-(hydroxymethyl)-2-(4- methoxyphenyl)butyl]benzenesulfonamide, 4-bromo-N-[(1S,2R)-2-ethyl-1- (hydroxymethyl)octyl]benzenesulfonamide, 4-bromo-N-[(1S,2S)-1-(hydroxymethyl)-2- methylpentyl]benzenesulfonamide, 4-bromo-N-[(1S,2S)-2-ethyl-1- (hydroxymethyl)pentyl]benzenesulfonamide, 4-bromo-N-[(1S,2R)-1-(hydroxymethyl)-4- methyl-2-propylpentyl]benzenesulfonamide, 4-bromo-N-[(1S,2R)-1-(hydroxymethyl)-2- propyloctyl]benzenesulfonamide, 4-bromo-N-[(1S,2S)-1-(hydroxymethyl)-2- methylheptyl]benzenesulfonamide, 4-bromo-N-[(1S,2S)-2-ethyl-1-(hydroxymethyl)heptyl]benzenesulfonamide, 4-bromo-N-[(1S,2S)-1-(hydroxymethyl)-2-phenylpropyl]benzenesulfonamide, 4-bromo-N-[(1S,2S)-1-(hydroxymethyl)-2-phenylbutyl]benzenesulfonamide, 4-bromo-N-[(1S,2R)-2-(2-furyl)-1-(hydroxymethyl)propyl]benzenesulfonamide, 4-bromo-N-[(1S,2R)-2-(2-furyl)-1-(hydroxymethyl)butyl]benzenesulfonamide, 4-bromo-N-[(1S,2R)-2-(2-furyl)-1-(hydroxymethyl)- 4-methylpentyl]benzenesulfonamide, 4-bromo-N-[(1S,2S)-1-(hydroxymethyl)-2-isopropyl- 4-methylpentyl]benzenesulfonamide, 4-chloro-N-[(1S,2S)-2-ethyl-1-(hydroxymethyl)octyl]benzenesulfonamide, 4-chloro-N-[(1S,2R)-2-ethyl-1- (hydroxymethyl)octyl]benzenesulfonamide, 4-chloro-N-methyl-N-[(1S,2S)-1- (hydroxymethyl)-2-methylbutyl]benzenesulfonamide, 4-chloro-N-[(1S)-1-(hydroxymethyl)-3-methylbutyl]benzenesulfonamide, 4-chloro-N-[(1R,2S)-2-hydroxy-1- methyl-2-phenylethyl]benzenesulfonamide, 4-bromo-N-[1- (hydroxymethyl)cyclopentyl]benzenesulfonamide, 4-chloro-N-[(1S)-2-cyclohexyl-1- (hydroxymethyl)ethyl]benzenesulfonamide, N-{(1S)-1-[4-(benzyloxy)benzyl]-2- hydroxyethyl}-4-chlorobenzenesulfonamide, 4-chloro-N-[(1R)-1-(hydroxymethyl)-1- methylpropyl]benzenesulfonamide, 4-bromo-N-[(1S,2S)-1-(hydroxymethyl)-2- methylbutyl]-benzenesulfonamide, 4-bromo-N-[1-(hydroxymethyl) pentyl]benzenesulfonamide, 4-bromo-N-[(1R,2S)-2-hydroxy-1-methyl-2-phenylethyl]benzenesulfonamide, 4-bromo-N-[(1S)-2-hydroxy-1-phenylethyl]benzenesulfonamide, 4-bromo-N-[(1R)-1-(hydroxymethyl)-3-methylbutyl]benzenesulfonamide, 4-chloro-N-[1- (hydroxymethyl)cyclopentyl]benzenesulfonamide, 4-bromo-N-[1-(hydroxymethyl)butyl]benzenesulfonamide, 3-chloro-N-[1-(hydroxymethyl)butyl]benzenesulfonamide, 3- chloro-N-[(1S)-2-cyclohexyl-1-(hydroxymethyl)ethyl]benzenesulfonamide, 3-chloro-N-[(1R)-1-(hydroxymethyl)-3-(methylthio)propyl]benzenesulfonamide, 3-chloro-N-[(1S)-1- (hydroxymethyl)propyl]benzenesulfonamide, 2-fluoro-N-[(1S)-1-(hydroxymethyl)-3- methylbutyl]benzenesulfonamide, 2-fluoro-N-[1-(hydroxymethyl)pentyl]benzenesulfonamide, 2-fluoro-N-[(1R,2S)-2-hydroxy-1-methyl-2-phenylethyl]benzenesulfonamide, 2-fluoro-N-[(1S)-2-hydroxy-1-phenylethyl]benzenesulfonamide, 2- fluoro-N-[(1R)-1-(hydroxymethyl)-3-methylbutyl]benzenesulfonamide, 2-fluoro-N-[1- (hydroxymethyl)cyclopentyl]benzenesulfonamide, N-[(1S)-2-cyclohexyl-1- (hydroxymethyl)ethyl]-2-fluorobenzenesulfonamide, 2-fluoro-N-{(1S,2S)-2-hydroxy-1- (hydroxymethyl)-2-[4-(methylthio)phenyl]ethyl}benzenesulfonamide, 2-fluoro-N-[(1S)- 1-(hydroxylmethylethyl]benzenesulfonamide, N-[(1S)-1-benzyl-2-hydroxyethyl]-2- fluorobenzenesulfonamide, 2-fluoro-N-[(1S)-1-(hydroxymethyl)-2-methylpropyl]benzenesulfonamide, 4-bromo-N-[1-(hydroxymethyl)cyclohexyl]benzenesulfonamide, 4- bromo-N-[2-(hydroxymethyl)bicyclo[2.2.1.]hept-2-yl]benzenesulfonamide, 4-bromo-N- [1-(hydroxymethyl)-2,3-dihydro-1H-inden-1-yl]benzenesulfonamide, 4-chloro-N-[1- (hydroxymethyl)cyclohexyl]benzenesulfonamide, 4-chloro-N-[1-(hydroxymethyl)-2,3- dihydro-1H-inden-1-yl]benzenesulfonamide, 4-chloro-N-(1-cyclobutyl-2-hydroxy-1- phenylethyl)benzenesulfonamide, 4-fluoro-N-[(1S,2S)-1-(1-hydroxyethyl)-2-methylbutyl]benzenesulfonamide, N-{(1S,2S)-1-[cyclopentyl(hydroxy)methyl]-2- methylbutyl}-4-fluorobenzenesulfonamide, 4-fluoro-N-{(1S)-2-hydroxy-1-[(1S)-1- methylpropyl]octyl}benzenesulfonamide, 4-fluoro-N-{(1S)-2-hydroxy-1-[(1S)-1- methylpropyl]heptyl}benzenesulfonamide, 4-fluoro-N-{(1S)-2-hydroxy-1-[(1S)-1- methylpropyl]hexyl}benzenesulfonamide, 4-fluoro-N-{(1S,2S)-1-[hydroxy(2- methylphenyl)methyl]-2-methylbutyl}benzenesulfonamide, 4-fluoro-N-{(1S)-2-hydroxy- 3,3-dimethyl-1-[(1S)-1-methylpropyl]butyl}benzenesulfonamide, 4-fluoro-N-{(1S)-2- hydroxy-1-[(1S)-1-methylpropyl]-3-butenyl}benzenesulfonamide, 4-fluoro-N-{(1S)-2- hydroxy-1-[(1S)-1-methylpropyl]-4-pentenyl}benzenesulfonamide, 4-fluoro-N-{(1S)-2- hydroxy-1-[(1S)-1-methylpropyl]butyl}benzenesulfonamide, N-{(1S,2S)-1-[(4-chlorophenyl)(hydroxy)methyl]-2-methylbutyl}-4-fluorobenzenesulfonamide, 4-fluoro-N-{(1S)-2-hydroxy-4-methyl-1-[(1S)-1-methylpropyl]-3-pentenyl}benzenesulfonamide, 4-fluoro- N-{(1S)-2-hydroxy-3-methyl-1-[(1S)-1-methylpropyl]-3-butenyl}benzenesulfonamide, 4-fluoro-N-{(1S,2S)-1-[hydroxy(4-methoxyphenyl)methyl]-2-methylbutyl}benzenesulfonamide, N-{(1S)-4-(1,3-dioxan-2-yl)-2-hydroxy-1-[(1S)-1- methylpropyl]butyl}-4-fluorobenzenesulfonamide, 4-fluoro-N-{(1S)-2-hydroxy-1-[(1S)- 1-methylpropyl]-5-hexenyl}benzenesulfonamide, 4-fluoro-N-((1S,2S)-1-{hydroxy[4- (methylsulfanyl)phenyl]methyl}-2-methylbutyl)benzenesulfonamide, N-{(1S,2S)-1-[[4- (dimethylamino)phenyl](hydroxy)methyl]-2-methylbutyl}-4-fluorobenzenesulfonamide, 4-fluoro-N-{(1S,2S)-1-[hydroxy(1-naphthyl)methyl]-2-methylbutyl}benzenesulfonamide, 4-bromo-N-[(1S,2S)-1-(1-hydroxyethyl)-2-methylbutyl]benzenesulfonamide, 4-bromo-N-{(1S,2S)-1-[cyclopentyl(hydroxy)methyly]-2-methylbutyl}benzenesulfonamide, 4-bromo-N-{(1S)-2-hydroxy-1-[(1S)-1- methylpropyl]heptyl}benzenesulfonamide, 4-bromo-N-{(1S)-2-hydroxy-1-[(1S)-1- methylpropyl]hexyl}benzenesulfonamide, 4-bromo-N-{(1S)-2-hydroxy-3,3-dimethyl-1- [(1S)-1-methylpropyl]butyl}benzenesulfonamide, 4-bromo-N-{(1S)-2-hydroxy-4-methyl-1-[(1S)-1-methylpropyl]pentyl}benzenesulfonamide, 4-bromo-N-{(1S)-2- hydroxy-1-[(1S)-1-methylpropyl]-3-butenyl}benzenesulfonamide, 4-bromo-N-{(1S)-2- hydroxy-1-[(1S)-1-methylpropyl]-4-pentenyl}benzenesulfonamide, 4-bromo-N-{(1S)-2-hydroxy-1-[(1S)-1-methylpropyl]butyl}benzenesulfonamide, 4-bromo-N-{(1S,2S)-1-[(4-fluorophenyl)(hydroxy)methyl]-2-methylbutyl}benzenesulfonamide, 4-bromo-N- {(1S,2S)-1-[(4-chlorophenyl)(hydroxy)methyl]-2-methylbutyl}benzenesulfonamide, 4- bromo-N-{(1S)-2-hydroxy-4-methyl-1-[(1S)-1-methylpropyl]-3-pentenyl}benzenesulfonamide, 4-bromo-N-{(1S)-2-hydroxy-3-methyl-1-[(1S)-1-methylpropyl]-3-butenyl}benzenesulfonamide, 4-bromo-N-{(1S,2S)-1-[hydroxy(4-methoxyphenyl)methyl]-2-methylbutyl}benzenesulfonamide, 4-bromo-N-{(1S,3E)-2-hydroxy-3-methyl- 1-[(1S)-1-methylpropyl]-3-pentenyl}benzenesulfonamide, 4-bromo-N-{(1S)-4-(1,3-dioxan-2-yl)-2-hydroxy-1-[(1S)-1-methylpropyl]butyl}benzenesulfonamide, 4-bromo-N- {(1S)-2-hydroxy-1-[(1S)-1-methylpropyl]-5-hexenyl}benzenesulfonamide, 4-bromo-N- {(1S)-2-hydroxy-1-[(1S)-1-methylpropyl]-3-pentynyl}benzenesulfonamide, 4-bromo-N- ((1S,2S)-1-{hydroxy[4-(methylsulfanyl)phenyl]methyl}-2-methylbutyl) benzenesulfonamide, 4-bromo-N-{(1S,2S)-1-[[4-(dimethylamino)phenyl](hydroxy)methyl]-2-methylbutyl}benzenesulfonamide, 4-chloro-N-[(1S,2S)-1-(1-hydroxyethyl)-2- methylbutyl]benzenesulfonamide, 4-chloro-N-{(1S,2S)-1- [cyclopentyl(hydroxy)methyl]-2-methylbutyl}benzenesulfonamide, 4-chloro-N-{(1S)-2-hydroxy-1-[(1S)-1-methylpropyl]octyl}benzenesulfonamide, 4-chloro-N-{(1S)-2- hydroxy-1-[(1S)-1-methylpropyl]heptyl}benzenesulfonamide, 4-chloro-N-{(1S)-2- hydroxy-1-[(1S)-1-methylpropyl]hexyl}benzenesulfonamide, 4-chloro-N-{(1S)-2- hydroxy-3-methyl-1-[(1S)-1-methylpropyl]butyl}benzenesulfonamide, 4- chloro-N-{(1S,2S)-1-[hydroxy(2-methylphenyl)methyl]-2-methylbutyl}benzenesulfonamide, 4- chloro-N-{(1S)-2-hydroxy-3,3-dimethyl-1-[(1S)- 1-methylpropyl]butyl}benzenesulfonamide, 4-chloro-N-{(1S)-2-hydroxy-4-methyl-1-[(1S)-1- methylpropyl]pentyl}benzenesulfonamide, 4-chloro-N-{(1S)-2-hydroxy-1-[(1S)-1- methylpropyl]-3-butenyl}benzenesulfonamide, 4-chloro-N-{(1S)-2-hydroxy-1-[(1S)-1- methylpropyl]-4-pentenyl}benzenesulfonamide, 4-chloro-N-{(1S)-2-hydroxy-1-[(1S)-1- methylpropyl]butyl}benzenesulfonamide, 4-chloro-N-{(1S,2S)-1-[(4- chlorophenyl)(hydroxy)methyl]-2-methylbutyl}benzenesulfonamide, 4-chloro-N- {(1S,2S)-1-[hydroxy(4-methoxyphenyl)methyl]-2-methylbutyl}benzenesulfonamide, 4- chloro-N-{(1S)-4-(1,3-dioxan-2-yl)-2-hydroxy-1-[(1S)-1-methylpropyl]butyl}benzenesulfonamide, 4-chloro-N-{(1S)-2-hydroxy-1-[(1S)-1-methylpropyl]-5-hexenyl}benzenesulfonamide, 4-chloro-N-{(1S)-2-hydroxy-1-[(1S)-1-methylpropyl]-3-pentynyl}benzenesulfonamide, 4-chloro-N-((1S,2S)-1-{hydroxy[4- (methylsulfanyl)phenyl]methyl}-2-methylbutyl)benzenesulfonamide, 4-chloro-N- {(1S,2S)-1-[[4-(dimethylamino)phenyl](hydroxy)methyl]-2-methylbutyl}benzenesulfonamide, 4-chloro-N-{(1S,2S)-1-[hydroxy(1-naphthyl)methyl]-2-methylbutyl}benzenesulfonamide, 3-chloro-N-[(1S,2S)-1-(1-hydroxyethyl)-2- methylbutyl]benzenesulfonamide, 3-chloro-N-{(1S,2S)-1-[cyclopentyl (hydroxy)methyl]-2-methylbutyl}benzenesulfonamide, 3-chloro-N-{(1S)-2-hydroxy-1- [(1S)-1-methylpropyl]octyl}benzenesulfonamide, 3-chloro-N-{(1S)-2-hydroxy-1-[(1S)- 1-methylpropyl]heptyl}benzenesulfonamide, 3-chloro-N-{(1S)-2-hydroxy-1-[(1S)-1- methylpropyl]hexyl}benzenesulfonamide, 3-chloro-N-{(1S)-2-hydroxy-3-methyl-1- [(1S)-1-methylpropyl]butyl}benzenesulfonamide, 3-chloro-N-{(1S)-2-hydroxy-3,3- dimethyl-1-[(1S)-1-methylpropyl]butyl}benzenesulfonamide, 3-chloro-N-{(1S)-2- hydroxy-4-methyl-1-[(1S)-1-methylpropyl]pentyl}benzenesulfonamide, 3-chloro-N- {(1S)-2-hydroxy-1-[(1S)-1-methylpropyl]-3-butenyl}benzenesulfonamide, 3-chloro-N- {(1S)-2-hydroxy-1-[(1S)-1-methylpropyl]-4-pentenyl}benzenesulfonamide, 3-chloro-N- {(1S)-2-hydroxy-1-[(1S)-1-methylpropyl]butyl}benzenesulfonamide, 3-chloro-N- {(1S,2S)-1-[(4-chlorophenyl)(hydroxy)methyl]-2-methylbutyl}benzenesulfonamide, 3- chloro-N-{(1S)-2-hydroxy-4-methyl-1-[(1S)-1-methylpropyl]-3-pentenyl}benzenesulfonamide, 3-chloro-N-{(1S,2S)-1-[hydroxy(4-methoxyphenyl)methyl]-2-methylbutyl}benzenesulfonamide, 3-chloro-N-{(1S)-4-(1,3-dioxan-2-yl)-2-hydroxy-1- [(1S)-1-methylpropyl]butyl}benzenesulfonamide, 3-chloro-N-{(1S)-2-hydroxy-1-[(1S)- 1-methylpropyl]-5-hexenyl}benzenesulfonamide, 3-chloro-N-((1S,2S)-1-{hydroxy[4- (methylsulfanyl)phenyl]methyl}-2-methylbutyl)benzenesulfonamide, N-{(1S,2S)-1- [cyclopentyl(hydroxy)methyl]-2-methylbutyl}-2-fluorobenzenesulfonamide, 2-fluoro-N- {(1S)-2-hydroxy-1-[(1S)-1-methylpropyl]octyl}benzenesulfonamide, 2-fluoro-N-{(1S)- 2-hydroxy-1-[(1S)-1-methylpropyl]heptyl}benzenesulfonamide, 2-fluoro-N-{(1S)- 2-hydroxy-1-[(1S)-1-methylpropyl]hexyl}benzenesulfonamide, 2-fluoro-N-{(1S)-2- hydroxy-1-[(1S)-1-methylpropyl]-3-butenyl}benzenesulfonamide, 2-fluoro-N-{(1S,2S)- 1-[(4-fluorophenyl)(hydroxy)methyl]-2-methylbutyl}benzenesulfonamide, N-{(1S,2S)- 1-[(4-chlorophenyl)(hydroxy)methyl]-2-methylbutyl}-2-fluorobenzenesulfonamide, 2- fluoro-N-{(1S,2S)-1-[hydroxy(4-methoxyphenyl)methyl]-2-methylbutyl}benzenesulfonamide, N-{(1S)-4-(1,3-dioxan-2-yl)-2-hydroxy-1-[(1S)-1-methylpropyl]butyl}-2-fluorobenzenesulfonamide, 4-bromo-N-[(1S,2S)-1-(1-hydroxy-1-methylethyl)- 2-methylbutyl]

benzenesulfonamide, 4-bromo-N-{(1S)-2-hydroxy-1-[(1S)-1-methylpropyl]-2-pentylheptyl}benzenesulfonamide, 4-bromo-N-{(1S)-2-butyl-2-hydroxy-1-[(1S)-1-methylpropyl]hexyl}benzenesulfonamide, 4-bromo-N-{(1S)-2-hydroxy-2-isobutyl-4-methyl-1-[(1S)-1-methylpropyl]pentyl}benzenesulfonamide, 4-bromo-N-{(1S,2S)-1-[hydroxy(diphenyl)methyl]-2-methylbutyl}benzenesulfonamide, N-{(1S)-2-allyl-2-hydroxy-1-[(1S)-1-methylpropyl]-4-pentenyl}-4-bromobenzenesulfonamide, 4-bromo-N-{(1S)-2-ethyl-2-hydroxy-1-[(1S)-1-methylpropyl]butyl}benzenesulfonamide, N-{(1S,2S)-1-[bis(4-chlorophenyl)(hydroxy)methyl]-2-methylbutyl}-4-bromobenzenesulfonamide, 4-bromo-N-{(1S)-2-hydroxy-2-isopropenyl-3-methyl-1-[(1S)-1-methylpropyl]-3-butenyl}benzenesulfonamide, 4-bromo-N-{(1S,3E)-2-hydroxy-3-methyl-2-[(1E)-1-methyl-1-propenyl]-1-[(1S)-1-methylpropyl]-3-pentenyl}benzenesulfonamide, 4-bromo-N-{(1S)-2-(3-butenyl)-2-hydroxy-1-[(1S)-1-methylpropyl]-5-hexenyl}benzenesulfonamide, 4-bromo-N-((1S,2S)-1-{hydroxy[di(1-naphthyl)]methyl}-2-methylbutyl)benzenesulfonamide, 4-chloro-N-[(1S,2S)-1-(1-hydroxy-1-methylethyl)-2-methylbutyl]benzenesulfonamide, 4-chloro-N-{(1S)-2-hexyl-2-hydroxy-1-[(1S)-1-methylpropyl]octyl}benzenesulfonamide, N-{(1S)-2-butyl-2-hydroxy-1-[(1S)-1-methylpropyl]hexyl}-4-chlorobenzenesulfonamide, 4-chloro-N-{(1S)-2-hydroxy-2-isobutyl-4-methyl-1-[(1S)-1-methylpropyl]pentyl}benzenesulfonamide, 4-chloro-N-{(1S,2S)-1-[hydroxy(diphenyl)methyl]-2-methylbutyl}benzenesulfonamide, N-{(1S)-2-allyl-2-hydroxy-1-[(1S)-1-methylpropyl]-4-pentenyl}-4-chlorobenzenesulfonamide, 4-chloro-N-{(1S)-2-ethyl-2-hydroxy-1-[(1S)-1-methylpropyl]butyl}benzenesulfonamide, 4-chloro-N-{(1S)-2-hydroxy-2-isopropenyl-3-methyl-1-[(1S)-1-methylpropyl]-3-butenyl}benzenesulfonamide, 4-chloro-N-((1S,2S)-1-{hydroxy[bis(4-methoxyphenyl)]methyl}-2-methylbutyl)benzenesulfonamide, 4-chloro-N-{(1S,3E)-2-hydroxy-3-methyl-2-[(1E)-1-methyl-1-propenyl]-1-[(1S)-1-methylpropyl]3-pentenyl}benzenesulfonamide, N-{(1S)-2-(3-butenyl)-2-hydroxy-1-[(1S)-1-methylpropyl]-5-hexenyl}-4-chlorobenzenesulfonamide, 4-chloro-N-((1S,2S)-1-{hydroxy[di(1-naphthyl)]methyl}-2-methylbutyl)benzenesulfonamide, 4-fluoro-N-[(1S,2S)-1-(1-hydroxy-1-methylethyl)-2-methylbutyl]benzenesulfonamide, 4-fluoro-N-{(1S)-2-hexyl-2-hydroxy-1-[(1S)-1-methylpropyl]octyl}benzenesulfonamide, 4-fluoro-N-{(1S)-2-hydroxy-1-[(1S)-1-methylpropyl]-2-pentylheptyl}benzenesulfonamide, N-{(1S)-2-butyl-2-hydroxy-1-[(1S)-1-methylpropyl]hexyl}-4-fluorobenzenesulfonamide, 4-fluoro-N-{(1S)-2-hydroxy-2-isopropenyl-3-methyl-1-[(1S)-1-methylpropyl]butyl}benzenesulfonamide, 4-fluoro-N-{(1S)-2-hydroxy-2-isobutyl-4-methyl-1-[(1S)-1-methylpropyl]pentyl}benzenesulfonamide, N-{(1S)-2-allyl-2-hydroxy-1-[(1S)-1-methylpropyl]-4-pentenyl}-4-fluorobenzenesulfonamide, N-{(1S)-2-ethyl-2-hydroxy-1-[(1S)-1-methylpropyl]butyl}-4-fluorobenzenesulfonamide, 4-fluoro-N-{(1S)-2-hydroxy-2-isopropenyl-3-methyl-1-[(1S)-1-methylpropyl]-3-butenyl}benzenesulfonamide, 4-fluoro-N-((1S,2S)-1-{hydroxy[bis(4-methoxyphenyl)]methyl}-2-methylbutyl)benzenesulfonamide, 4-fluoro-N-{(1S,3E)-2-hydroxy-3-methyl-2-[(1E)-1-methyl-1-propenyl]-1-[(1S)-1-methylpropyl]-3-pentenyl}benzenesulfonamide, N-{(1S)-2-(3-butenyl)-2-hydroxy-1-[(1S)-1-methylpropyl]-5-hexenyl}-4-fluorobenzenesulfonamide, N-{(1S,2S)-1-[bis[4-(dimethylamino)phenyl](hydroxy)methyl]-2-methylbutyl}-4-fluorobenzenesulfonamide, 4-fluoro-N-((1S,2S)-1-{hydroxy[di(1-naphthyl)]methyl}-2-methylbutyl)benzenesulfonamide, 3-chloro-N-{(1S)-2-hexyl-2-hydroxy-1-[(1S)-1-methylpropyl]octyl}benzenesulfonamide, 3-chloro-N-{(1S)-2-hydroxy-1-[(1S)-1-methylpropyl]-2-pentylheptyl}benzenesulfonamide, N-{(1S)-2-butyl-2-hydroxy-1-[(1S)-1-methylpropyl]hexyl}-3-chlorobenzenesulfonamide, 3-chloro-N-{(1S)-2-hydroxy-2-isobutyl-4-methyl-1-[(1S)-1-methylpropyl]pentyl}benzenesulfonamide, 3-chloro-N-{(1S,2S)-1-[hydroxy(diphenyl)methyl]-2-methylbutyl}benzenesulfonamide, N-{(1S)-2-allyl-2-hydroxy-1-[(1S)-1-methylpropyl]-4-pentenyl}-3-chlorobenzenesulfonamide, 3-chloro-N-{(1S)-2-ethyl-2-hydroxy-1-[(1S)-1-methylpropyl]butyl}benzenesulfonamide, N-{(1S,2S)-1-[bis(4-chlorophenyl)(hydroxy)methyl]-2-methylbutyl}-3-chlorobenzenesulfonamide, 3-chloro-N-{(1S)-2-hydroxy-2-isopropenyl-3-methyl-1-[(1S)-1-methylpropyl]-3-butenyl}benzenesulfonamide, 3-chloro-N-((1S,2S)-1-{hydroxy[bis(4-methoxyphenyl)]methyl}-2-methylbutyl)benzenesulfonamide, 3-chloro-N-{(1S,3E)-2-hydroxy-3-methyl-2-[(1E)-1-methyl-1-propenyl]-1-[(1S)-1-methylpropyl]-3-pentenyl}benzenesulfonamide, N-{(1S)-2-(3-butenyl)-2-hydroxy-1-[(1S)-1-methylpropyl]-5-hexenyl}-3-chlorobenzenesulfonamide, 2-fluoro-N-{(1S)-2-hexyl-2-hydroxy-1-[(1S)-1-methylpropyl]octyl}benzenesulfonamide, 2-fluoro-N-{(1S)-2-hydroxy-1-[(1S)-1-methylpropyl]-2-pentylheptyl}benzenesulfonamide, 2-fluoro-N-{(1S,2S)-1-[hydroxy(diphenyl)methyl]-2-methylbutyl}benzenesulfonamide, N-{(1S)-2-allyl-2-hydroxy-1-[(1S)-1-methylpropyl]-4-pentenyl}-2-fluorobenzenesulfonamide, N-{(1S)-2-ethyl-2-hydroxy-1-[(1S)-1-methylpropyl]butyl}-2-fluorobenzenesulfonamide, N-{(1S,2S)-1-[bis(4-fluorophenyl)(hydroxy)methyl]-2-methylbutyl}-2-fluorobenzenesulfonamide, N-{(1S,2S)-1-[bis(4-chlorophenyl)(hydroxy)methyl]-2-methylbutyl}-2-fluorobenzenesulfonamide, 2-fluoro-N-{(1S)-2-hydroxy-2-isopropenyl-3-methyl-1-[(1S)-1-methylpropyl]-3-butenyl}benzenesulfonamide, 2-fluoro-N-((1S,2S)-1-{hydroxy[bis(4-methoxyphenyl)]methyl}-2-methylbutyl)benzenesulfonamide, 2-fluoro-N-{(1S,3E)-2-hydroxy-3-methyl-2-[(1E)-1-methyl-1-propenyl]-1-[(1S)-1-methylpropyl]-3-pentenyl}benzenesulfonamide, N-{(1S)-2-(3-butenyl)-2-hydroxy-1-[(1S)-1-methylpropyl]-5-hexenyl}-2-fluorobenzenesulfonamide, 4-chloro-N-[(1S)-1-cyclohexyl-2-hydroxyethyl]benzenesulfonamide, 4-chloro-N-[(1S)-2-hydroxy-1-phenylethyl]benzenesulfonamide, 4-chloro-N-[(1S)-1-(hydroxymethyl)-2-methylpropyl]benzenesulfonamide, 4-bromo-N-[(1S)-1-(hydroxymethyl)-2-methylpropyl]benzenesulfonamide, 4-iodo-N-[(1S,2S)-1-(hydroxymethyl)-2-methylbutyl]benzenesulfonamide, and 4-chloro-N-[(1S)-1-(hydroxymethyl)-2,2-dimethylpropyl]benzenesulfonamide;

or a pharmaceutically acceptable salt, hydrate, or prodrug thereof.

5. The compound according to claim 1, which is 4-chloro-N-[(1S, 2S)-2-ethyl-1-(hydroxymethyl)butyl]benzenesulfonamide or a pharmaceutically acceptable salt, hydrate, or prodrug thereof.

6. The compound according to claim 1, wherein $R_3$ is halogen and $R_8$ is a lower alkyl of S-stereochemistry at the carbon atom to which N and T are attached; or a pharmaceutically acceptable salt.

7. A pharmaceutical composition comprising a physiologically compatible carrier and a compound according to claim 1.

8. A compound of Formula I:

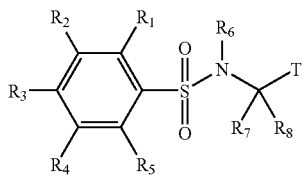

wherein:
R₁ is selected from the group consisting of H, halogen, and O;
R₂ is selected from the group consisting of H, halogen, and N═N;
R₃ is selected from the group consisting of H and halogen;
R₄ is selected from the group consisting of H, halogen, amino, and N═N;
R₅ is selected from the group consisting of H, halogen, methoxy, methyl, and O;
or
R₁ and R₂ or R₄ and R₅ are fused to form a carbon-based, unsaturated ring;
R₆ is selected from the group consisting of H, lower alkyl, lower alkenyl, 3-phenyl-2-propyn-1-yl, benzyl, substituted benzyl, CH₂ cycloalkyl, CH₂-2-furan, (CH₂)₂SCH₃, and (CH₂)₂NHBOC;
R₇ is selected from the group consisting of H, lower alkyl, and cycloalkyl;
R₈ is selected from the group consisting of benzyl and substituted benzyl;
T is

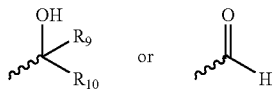

R₉ and R₁₀ are H; or
R₉ is H and R₁₀ is selected from the group consisting of lower alkyl, lower alkenyl, CF₃, methyl-substituted alkenyl, lower alkynyl, cycloalkyl, substituted phenyl, 1-naphthyl, and CH₂CH₂-1,3-dioxolane; or
R₉ and R₁₀ are independently selected from the group consisting of lower alkyl, lower alkenyl, phenyl, 4-substituted-phenyl, and 1-naphthyl;
wherein:
(i) when R₅ is a methoxy; R₂ is halogen and R₁, R₃, and R₄ are H;
(ii) when R₅ is a methyl; R₁ is halogen and R₂, R₃, and R₄ are H;
(iii) when R₄ is an amino; R₃ is halogen and R₁, R₂, and R₅ are H;
(iv) when R₂ is N═N, R₁ is O and R₂ is bound to R₁ to form a heterocyclic ring;
(v) when R₄ is N═N, R₅ is O and R₄ is bound to R₅ to form a heterocyclic ring; and
(vi) one or more of R₁ to R₅ is a halogen; or a pharmaceutically acceptable salt, hydrate, or prodrug thereof.

9. A pharmaceutical composition comprising a physiologically compatible carrier and a compound according to claim 8.

10. A compound of Formula Ib:

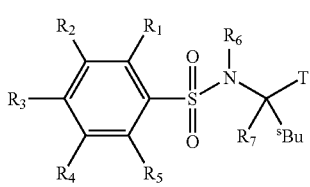

wherein:
R₁ is selected from the group consisting of H, halogen, and O;
R₂ is selected from the group consisting of H, halogen, and N═N;
R₃ is selected from the group consisting of H, bromine, fluorine, and iodine;
R₄ is selected from the group consisting of H, halogen, amino, and N═N;
R₅ is selected from the group consisting of H, halogen, methoxy, methyl, and O;
R₆ is selected from the group consisting of H, lower alkyl, lower alkenyl, 3-phenyl-2-propyn-1-yl, benzyl, substituted benzyl, CH₂ cycloalkyl, CH₂-2-furan, (CH₂)₂SCH₃, and (CH₂)₂NHBOC;
R₇ is selected from the group consisting of H, lower alkyl, and cycloalkyl;
T is

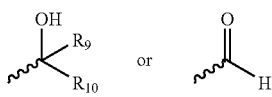

R₉ and R₁₀ are H; or
R₉ is H and R₁₀ is selected from the group consisting of lower alkyl, lower alkenyl, CF₃, methyl-substituted alkenyl, lower alkynyl, cycloalkyl, substituted phenyl, 1-naphthyl, and CH₂CH₂-1,3-dioxolane; or
R₉ and R₁₀ are independently selected from the group consisting of lower alkyl, lower alkenyl, phenyl, 4-substituted-phenyl, and 1-naphthyl;
wherein:
(i) when R₅ is a methoxy; R₂ is halogen and R₁, R₃, and R₄ are H;
(ii) when R₅ is a methyl; R₁ is halogen and R₂, R₃, and R₄ are H;
(iii) when R₄ is an amino; R₃ is halogen and R₁, R₂, and R₅ are H;
(iv) when R₂ or R₄ is N═N; R₁ or R₅ is O and R₂ or R₄ is bound to R₁ or R₅ to form a heterocyclic ring; and
(v) one or more of R₁ to R₅ is a halogen;
or a pharmaceutically acceptable salt, hydrate, or prodrug thereof.

11. A pharmaceutical composition comprising a physiologically compatible carrier and a compound according to claim 10.

12. A compound of Formula I:

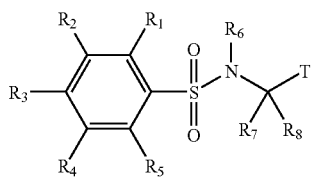

wherein:
  $R_1$ is selected from the group consisting of H, halogen, and O;
  $R_2$ is selected from the group consisting of H, halogen, and N=N;
  $R_3$ is selected from the group consisting of H and halogen;
  $R_4$ is selected from the group consisting of H, halogen, amino, and N=N;
  $R_5$ is selected from the group consisting of H, halogen, methoxy, methyl, and O;
  $R_6$ is selected from the group consisting of H, lower alkyl, lower alkenyl, 3-phenyl-2-propyn-1-yl, benzyl, substituted benzyl, $CH_2$ cycloalkyl, $CH_2$-2-furan, $(CH_2)_2 SCH_3$, and $(CH_2)_2NHBOC$;
  $R_7$ is selected from the group consisting of lower alkyl and cycloalkyl;
  $R_8$ is selected from the group consisting of cycloalkyl, phenyl, substituted phenyl, $CH_2$ cycloalkyl, CH(lower alkyl)-2-furan, CH(lower alkyl)-4-methoxyphenyl, CH(lower alkyl)phenyl, and CH(OH)-4-$SCH_3$-phenyl;
  T is

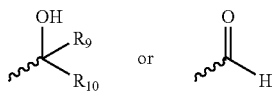

$R_9$ and $R_{10}$ are H; or
  $R_9$ is H and $R_{10}$ is selected from the group consisting of lower alkyl, lower alkenyl, $CF_3$, methyl-substituted alkenyl, lower alkynyl, cycloalkyl, substituted phenyl, 1-naphthyl, and $CH_2CH_2$-1,3-dioxolane; or
  $R_9$ and $R_{10}$ are independently selected from the group consisting of lower alkyl, lower alkenyl, phenyl, 4-substituted-phenyl, and 1-naphthyl;
  wherein:
    (i) when $R_5$ is a methoxy; $R_2$ is halogen and $R_1$, $R_3$, and $R_4$ are H;
    (ii) when $R_5$ is a methyl; $R_1$ is halogen and $R_2$, $R_3$, and $R_4$ are H;
    (iii) when $R_4$ is an amino; $R_3$ is halogen and $R_1$, $R_2$, and $R_5$ are H;
    (iv) when $R_2$ is N=N, $R_1$ is O and $R_2$ is bound to $R_1$ to form a heterocyclic ring;
    (v) when $R_4$ is N=N, $R_5$ is O and $R_4$ is bound to $R_5$ to form a heterocyclic ring; and
    (vi) one or more of $R_1$ to $R_5$ is a halogen;
or a pharmaceutically acceptable salt, hydrate, or prodrug thereof.

13. A pharmaceutical composition comprising a physiologically compatible carrier and a compound according to claim 12.

14. A compound of Formula I:

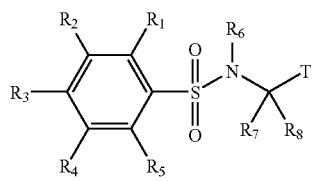

wherein:
  $R_1$ is selected from the group consisting of H, halogen, and O;
  $R_2$ is selected from the group consisting of H, halogen, and N=N;
  $R_3$ is selected from the group consisting of H and halogen;
  $R_4$ is selected from the group consisting of H, halogen, amino, and N=N;
  $R_5$ is selected from the group consisting of H, halogen, methoxy, methyl, and O;
or
  $R_1$ and $R_2$; $R_2$ and $R_3$; $R_4$ and $R_5$; or $R_3$ and $R_4$ are fused to form a carbon-based, naphthalene ring with the benzene ring;
  $R_6$ is selected from the group consisting of H, lower alkyl, lower alkenyl, 3-phenyl-2-propyn-1-yl, benzyl, substituted benzyl, $CH_2$ cycloalkyl, $CH_2$-2-furan, $(CH_2)_2 SCH_3$, and $(CH_2)_2NHBOC$;
  $R_7$ is selected from the group consisting of H, lower alkyl, and cycloalkyl;
  $R_8$ is selected from the group consisting of cycloalkyl, phenyl, substituted phenyl, benzyl, substituted benzyl, $CH_2$ cycloalkyl, CH(lower alkyl)-2-furan, CH(lower alkyl)-4-methoxyphenyl, CH(lower alkyl)phenyl, and CH(OH)-4-$SCH_3$-phenyl; or
  $R_7$ and $R_8$ are fused to form a saturated carbon-based ring;
  T is

wherein:
  (i) when $R_5$ is a methoxy; $R_2$ is halogen and $R_1$, $R_3$, and $R_4$ are H;
  (ii) when $R_5$ is a methyl; $R_1$ is halogen and $R_2$, $R_3$, and $R_4$ are H;
  (iii) when $R_4$ is an amino; $R_3$ is halogen and $R_1$, $R_2$, and $R_5$ are H;
  (iv) when $R_2$ is N=N, $R_1$ is O and $R_2$ is bound to $R_1$ to form a heterocyclic ring;
  (v) when $R_4$ is N=N, $R_5$ is O and $R_4$ is bound to $R_5$ to form a heterocyclic ring;
  (vi) when each of $R_1$, $R_2$, $R_4$, $R_5$, and $R_6$ is H, $R_3$ is halogen, and $R_7$ is H, then $R_8$ is $C_5$ to $C_8$ alkyl or $R_7$ and $R_8$ are fused to form a saturated carbon-based ring;
  (vii) when each of $R_3$, $R_4$, $R_5$, $R_6$, and $R_7$ is H and $R_1$ and $R_2$ are fused to form a carbon-based naphthalene ring, then $R_8$ is selected from the group consisting of lower alkyl, cycloalkyl, phenyl, substituted phenyl, benzyl, substituted benzyl, $CH_2$ cycloalkyl, CH(lower alkyl)-2-furan, CH(lower alkyl)-4-methoxyphenyl; CH(lower alkyl)phenyl, and CH(OH)-4-SCH$_3$-phenyl;

(viii) when each of R$_1$, R$_2$, R$_4$, R$_5$, and R$_6$ is H and R$_3$ is halogen, then R$_7$ and R$_8$ are not both CH$_3$; and (ix) at least one of R$_1$, R$_2$, R$_3$, R$_4$, and R$_5$ is halogen unless R$_1$ and R$_2$; R$_2$ and R$_3$; R$_4$ and R$_5$; or R$_3$ and R$_4$ are fused to form a carbon-based, naphthalene ring with the benzene ring;

or a pharmaceutically acceptable salt, hydrate, or prodrug thereof.

15. A pharmaceutical composition comprising a physiologically compatible carrier and a compound according to claim 14.

16. A compound of Formula I:

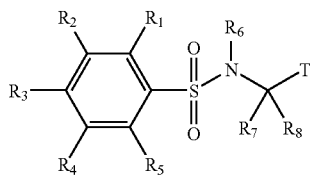

I wherein:
R$_1$ is selected from the group consisting of H, halogen, and O;

R$_2$ is selected from the group consisting of H, halogen, and N═N;

R$_3$ is selected from the group consisting of H and halogen;

R$_4$ is selected from the group consisting of H, halogen, amino, and N═N;

R$_5$ is selected from the group consisting of H, halogen, methoxy, methyl, and O;

or

R$_1$ and R$_2$; R$_2$ and R$_3$; R$_4$ and R$_5$; or R$_3$ and R$_4$ are fused to form a carbon-based, naphthalene ring with the benzene ring;

R$_6$ is selected from the group consisting of lower alkyl, lower alkenyl, 3-phenyl-2-propyn-1-yl, benzyl, substituted benzyl, CH$_2$ cycloalkyl, CH$_2$-2-furan, (CH$_2$)$_2$SCH$_3$, and (CH$_2$)$_2$NHBOC;

R$_7$ and R$_8$ are fused to form a saturated carbon-based ring;

T is

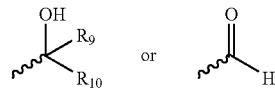

R$_9$ and R$_{10}$ are H; or

R$_9$ is H and R$_{10}$ is selected from the group consisting of lower alkyl, lower alkenyl, CF$_3$, methyl-substituted alkenyl, lower alkynyl, cycloalkyl, substituted phenyl, 1-naphthyl, and CH$_2$CH$_2$-1,3-dioxolane; or R$_9$ and R$_{10}$ are independently selected from the group consisting of lower alkyl, lower alkenyl, phenyl, 4-substituted-phenyl, and 1-naphthyl;

wherein:
(i) when R$_5$ is a methoxy; R$_2$ is halogen and R$_1$, R$_3$, and R$_4$ are H;

(ii) when R$_5$ is a methyl; R$_1$ is halogen and R$_2$, R$_3$, and R$_4$ are H;

(iii) when R$_4$ is an amino; R$_3$ is halogen and R$_1$, R$_2$, and R$_5$ are H;

(iv) when R$_2$ is N═N, R$_1$ is O and R$_2$ is bound to R$_1$ to form a heterocyclic ring;

(v) when R$_4$ is N═N, R$_5$ is O and R$_4$ is bound to R$_5$ to form a heterocyclic ring; and (vi) at least one of R$_1$, R$_2$, R$_3$, R$_4$, and R$_5$ is halogen unless R$_1$ and R$_2$; R$_2$ and R$_3$; R$_4$ and R$_5$; or R$_3$ and R$_4$ are fused to form a carbon-based, naphthalene ring with the benzene ring;

or a pharmaceutically acceptable salt, metabolite, hydrate, or prodrug thereof.

17. A pharmaceutical composition comprising a physiologically compatible carrier and a compound according to claim 16.

* * * * *

UNITED STATES PATENT AND TRADEMARK OFFICE
CERTIFICATE OF CORRECTION

PATENT NO. : 7,166,622 B2
APPLICATION NO. : 10/457641
DATED : January 23, 2007
INVENTOR(S) : Kreft et al.

It is certified that error appears in the above-identified patent and that said Letters Patent is hereby corrected as shown below:

Col. 10, line 54, replace "(11S)" with -- (1S) --.

Col. 12, line 42, replace "[(1 S,2 S)" with -- [(1R, 2S) --.

Col. 13, line 3, replace "-N{" with -- -N-{ --.

Col. 13, line 13, replace "1-[(1S)" with -- -1-[(1S) --.

Col. 13, line 29, replace "N-1-{" with -- N-{ --.

Col. 13, line 35, replace "(S)" with -- (1S) --.

Col. 13, line 49, replace "(11 S,2S)" with -- (1S, 2S) --.

Col. 14, line 59, replace "N-{((S," with -- N-{(1S --.

Col. 14, line 66, replace "[(1S)l-" with -- [(1S)-1- --.

Col. 15, line 17, replace "1-[(1S)" with -- -1-[(1S) --.

Col. 16, line 28, replace "(18)" with -- (1S) --.

Col. 16, line 32, replace "(1    F)" with -- (1E) --.

Col. 16, line 36, replace "(18)" with -- (1S) --.

Col. 24, Scheme 4, replace the second occurrence of "XI" with -- XII --.

Col. 32, line 33, table 1, replace "$Et_2N$, THF" with -- $Et_3N$, THF --.

Col. 38, line 54, table 6, replace "$Ph_3$, DEAD" with -- $Ph_3P$, DEAD --.

UNITED STATES PATENT AND TRADEMARK OFFICE
CERTIFICATE OF CORRECTION

PATENT NO. : 7,166,622 B2
APPLICATION NO. : 10/457641
DATED : January 23, 2007
INVENTOR(S) : Kreft et al.

It is certified that error appears in the above-identified patent and that said Letters Patent is hereby corrected as shown below:

Col. 52, table 12, delete table 12 and replace with the following:

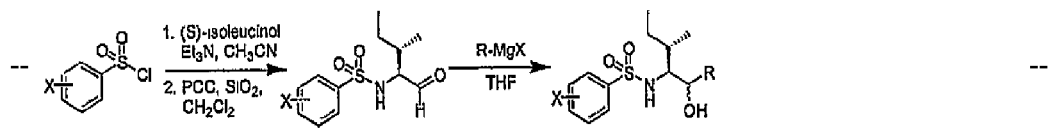

Table 12 (LCMS Data[2]: Molecular ion and retention time(s))

| RMgX | X-Ph | | | | |
|---|---|---|---|---|---|
| | 4-fluoro-Ph | 4-bromo-Ph | 4-chloro-Ph | 3-chloro-Ph | 2-fluoro-Ph |
| Methyl magnesium bromide | Ex. 126 288.18 (M-H) 1.01 min | Ex. 145 350.05 (M-H) 1.12 min | Ex. 165 304.10 (M-H) 1.04 min, 1.10 min | Ex. 185 304.15 (M-H) 1.05 min, 1.12 min | |
| Cyclopentyl magnesium bromide | Ex. 127 242.21 (M-H) 1.30 min | Ex. 146 404.05 (M-H) 1.40 min | Ex. 166 358.18 (M-H) 1.37 min | Ex. 186 358.18 (M-H) 1.39 min | Ex. 202 342.22 (M-H) 1.29 min |
| Hexyl magnesium bromide | Ex. 128 358.24 (M-H), 1.40 min, 1.44 min | | Ex. 167 374.21 (M-H) 1.48 min, 1.52 min | Ex. 187 374.22 (M-H) 1.48 min, 1.53 min | Ex. 203 358.24 (M-H) 1.41 min, 1.46 min |
| Pentyl magnesium bromide | Ex. 129 344.23 (M-H) 1.32 min, 1.36 min | Ex. 147 406.10 (M-H), 1.40 min, 1.46 min | Ex. 168 360.19 (M-H) 1.40 min, 1.45 min | Ex. 188 360.20 (M-H) 1.40 min, 1.46 min | Ex. 204 344.22 (M-H) 1.32 min, 1.36 min |
| Butyl magnesium bromide | Ex. 130 330.21 (M-H) 1.24 min, 1.28 min | Ex. 148 392.07 (M-H), 1.34 min, 1.39 min | Ex. 169 346.18 (M-H) 1.33 min, 1.37 min | Ex. 189 346.17 (M-H) 1.33 min, 1.38 min | Ex. 205 330.23 (M-H) 1.25 min, 1.30 min |
| Isopropyl magnesium bromide | | | Ex. 170 332.17 (M-H) 1.25 min, 1.30 min | Ex. 190 332.18 (M-H) 1.26 min, 1.31 min | |
| o-tolyl magnesium bromide | Ex. 131 364.19 (M-H) 1.28 min | | Ex. 171 380.17 (M-H) 1.36 min | | |

UNITED STATES PATENT AND TRADEMARK OFFICE
CERTIFICATE OF CORRECTION

PATENT NO. : 7,166,622 B2
APPLICATION NO. : 10/457641
DATED : January 23, 2007
INVENTOR(S) : Kreft et al.

It is certified that error appears in the above-identified patent and that said Letters Patent is hereby corrected as shown below:

Col. 52, table 12...(cont'd):

| | Ex. 132 | Ex. 149 | Ex. 172 | Ex. 191 | |
|---|---|---|---|---|---|
| tert-butyl magnesium bromide | 330.21 (M-H) 1.31 min | 392.08 (M-H) 1.42 min | 346.17 (M-H) 1.40 min | 346.18 (M-H) 1.40 min | |
| Isobutyl magnesium bromide | | Ex. 150 392.06 (M-H) 1.33 min, 1.37 min | Ex. 173 346.17 (M-H) 1.31 min, 1.36 min | Ex. 192 346.18 (M-H) 1.32 min, 1.37 min | |
| Vinyl magnesium bromide | Ex. 133 300.18 (M-H) 1.04 min, 1.08 min | Ex. 151 362.07 (M-H) 1.16 min, 1.20 min | Ex. 174 316.14 (M-H) 1.13 min, 1.17 min | Ex. 193 316.16 (M-H) 1.13 min, 1.18 min | Ex. 206 300.18 (M-H) 1.03 min, 1.08 min |
| Allyl magnesium bromide | Ex. 134 314.19 (M-H) 1.12 min, 1.16 min | Ex. 152 376.05 (M-H) 1.22 min, 1.26 min | Ex. 175 330.14 (M-H) 1.21 min, 1.25 min | Ex. 194 330.17 (M-H) 1.20 min, 1.25 min | |
| Ethyl magnesium bromide | Ex. 135 302.19 (M-H) 1.06 min, 1.11 min | Ex. 153 364.09 (M-H) 1.18 min, 1.23 min | Ex. 176 318.16 (M-H) 1.16 min, 1.21 min | Ex. 195 318.16 (M-H) 1.16 min, 1.21 min | |
| 4-fluoro phenyl magnesium bromide | | Ex. 154 429.99 (M-H) 1.28 min, 1.33 min | | | Ex. 207 368.17 (M-H) 1.18 min, 1.23 min |
| 4-chloro phenyl magnesium bromide | Ex. 136 384.14 (M-H) 1.26 min, 1.30 min | Ex. 155 446.01 (M-H) 1.35 min, 1.40 min | Ex. 177 402.03 (M-H) 1.33 min, 1.35 min | Ex. 196 402.06 (M-H) 1.33 min, 1.38 min | Ex. 208 384.14 (M-H) 1.25 min, 1.30 min |
| 2-methyl-1-propenyl magnesium bromide | Ex. 137 238.18 (M-H) 1.16 min, 1.21 min | Ex. 156 390.04 (M-H) 1.25 min, 1.31 min | | Ex. 197 344.19 (M-H) 1.24 min, 1.30 min | |

UNITED STATES PATENT AND TRADEMARK OFFICE
CERTIFICATE OF CORRECTION

| | |
|---|---|
| PATENT NO. | : 7,166,622 B2 |
| APPLICATION NO. | : 10/457641 |
| DATED | : January 23, 2007 |
| INVENTOR(S) | : Kreft et al. |

It is certified that error appears in the above-identified patent and that said Letters Patent is hereby corrected as shown below:

Col. 55, line 7, replace "(333 mL," with -- (333μL, --.

Col. 55, table 13, delete table 13 and replace with the following:
-- --

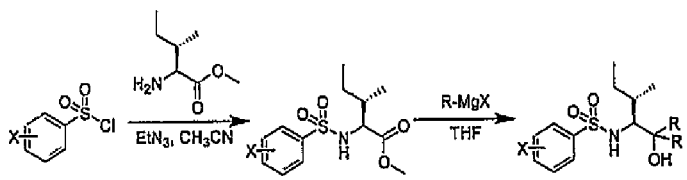

Table 13 (LCMS Data[2]: Molecular ion and retention time)

| RMgX | X-Ph | | | | |
|---|---|---|---|---|---|
| | 4-bromo-Ph | 4-chloro-Ph | 4-fluoro-Ph | 3-chloro-Ph | 2-fluoro-Ph |
| Methyl magnesium bromide | Ex. 211 364.51 (M-H) 1.117 min | Ex. 223 318.61 (M-H) 1.15 min | Ex. 235 302.64 (M-H) 1.06 min | | |
| Hexyl magnesium bromide | | Ex. 224 458.78 (M-H) 1.87 min | Ex. 236 442.78 (M-H) 1.80 min | Ex. 249 458.75 (M-H) 1.87 min | Ex. 261 442.78 (M-H) 1.81 min |

UNITED STATES PATENT AND TRADEMARK OFFICE
CERTIFICATE OF CORRECTION

PATENT NO. : 7,166,622 B2
APPLICATION NO. : 10/457641
DATED : January 23, 2007
INVENTOR(S) : Kreft et al.

It is certified that error appears in the above-identified patent and that said Letters Patent is hereby corrected as shown below:

Col. 55, table 13...(cont'd):

| | | | | | | |
|---|---|---|---|---|---|---|
| -- | Pentyl magnesium bromide | Ex. 212 476.49 (M-H) 1.76 min | | Ex. 237 414.82 (M-H) 1.70 min | Ex. 250 430.76 (M-H) 1.76 min | Ex. 262 414.74 (M-H) 1.70 min | -- |
| | Butyl magnesium bromide | Ex. 213 448.59 (M-H) 1.65 min | Ex. 225 402.72 (M-H) 1.63 min | Ex. 238 386.73 (M-H) 1.58 min | Ex. 251 402.68 (M-H) 1.65 min | |
| | Isopropyl magnesium bromide | | | Ex. 239 358.70 (M-H) 1.47 min | | |
| | Isobutyl magnesium bromide | Ex. 214 448.58 (M-H) 1.65 min | Ex. 226 402.70 (M-H) 1.63 min | Ex. 240 386.73 (M-H) 1.58 min | Ex. 252 402.74 (M-H) 1.65 min | |
| | Phenyl magnesium bromide | Ex. 215 488.51 (M-H) 1.50 min | Ex. 227 442.65 (M-H) 1.48 min | | Ex. 253 442.64 (M-H) 1.50 min | Ex. 263 426.67 (M-H) 1.43 min |
| | Allyl magnesium bromide | Ex. 216 416.53 (M-H) 1.43 min | Ex. 228 370.65 (M-H) 1.41 min | Ex. 241 354.69 (M-H) 1.34 min | Ex. 254 370.64 (M-H) 1.43 min | Ex. 264 354.67 (M-H) 1.35 min |
| -- | Ethyl magnesium bromide | Ex. 217 392.55 (M-H) 1.37 min | Ex. 229 346.67 (M-H) 1.35 min | Ex. 242 330.67 (M-H) 1.28 min | Ex. 255 346.66 (M-H) 1.37 min | Ex. 265 330.74 (M-H) 1.28 min | -- |
| | 4-fluoro phenyl magnesium bromide | | | | | Ex. 266 462.64 (M-H) 1.45 min |
| | 4-chloro phenyl magnesium bromide | Ex. 218 556.39 (M-H) 1.61 min | | | Ex. 256 511.96 (M-H) 1.66 min | Ex. 267 494.57 (M-H) 1.56 min |
| | isopropenyl magnesium bromide | Ex. 219 416.51 (M-H) 1.50 min | Ex. 230 370.64 (M-H) 1.48 min | Ex. 243 354.69 (M-H) 1.43 min | Ex. 257 370.66 (M-H) 1.48 min | Ex. 268 354.68 (M-H) 1.43 min |
| | 4-anisyl magnesium bromide | | Ex. 231 502.64 (M-H) 1.43 min | Ex. 244 486.67 (M-H) 1.38 min | Ex. 258 502.62 (M-H) 1.43 min | Ex. 269 486.71 (M-H) 1.37 min |

Page 5 of 7

UNITED STATES PATENT AND TRADEMARK OFFICE
CERTIFICATE OF CORRECTION

PATENT NO. : 7,166,622 B2
APPLICATION NO. : 10/457641
DATED : January 23, 2007
INVENTOR(S) : Kreft et al.

It is certified that error appears in the above-identified patent and that said Letters Patent is hereby corrected as shown below:

Col.55, table 13 (cont'd)
-- --

| | | | | | |
|---|---|---|---|---|---|
| 1-methyl-1-propenyl magnesium bromide | Ex. 220 444.59 (M-H) 1.63 min | Ex. 232 398.69 (M-H) 1.61 min | Ex. 245 382.73 (M-H) 1.54 min | Ex. 259 398.65(M-H) 1.61 min | Ex. 270 382.50 (M-H) 1.56 min |
| 3-butenyl magnesium bromide | Ex. 221 444.60 (M-H) 1.54 min | Ex. 233 398.66 (M-H) 1.52 min | Ex. 246 382.71 (M-H) 1.46 min | Ex. 260 518.68 (M-H) 1.21 min | Ex. 271 382.70 (M-H) 1.46 min |
| 4-$N,N$-dimethyl aniline magnesium bromide | | | Ex. 247 512.73 (M-H) 0.97 min | | |
| 1-naphthyl magnesium bromide | Ex. 222 558.46 (M-H) 1.65 min | Ex. 234 542.56 (M-H) 1.63 min | Ex. 248 526.69 (M-H) 1.58 min | | |

Col. 58, line 28, replace "(1S)-Q-" with -- (αS)-α- --.

Col. 60, line 67, replace "NO₃S:" with -- lNO₃S: --.

Col. 62, line 9, replace "additional-methylene" with -- additional methylene --.

Col. 74, line 59, replace "10 IM/mL." with -- 10μM/mL. --.

UNITED STATES PATENT AND TRADEMARK OFFICE
CERTIFICATE OF CORRECTION

PATENT NO. : 7,166,622 B2
APPLICATION NO. : 10/457641
DATED : January 23, 2007
INVENTOR(S) : Kreft et al.

It is certified that error appears in the above-identified patent and that said Letters Patent is hereby corrected as shown below:

Col. 74, line 60, replace "<0.75" with -- ≤0.75 --.

Signed and Sealed this

Twenty-seventh Day of November, 2007

JON W. DUDAS
*Director of the United States Patent and Trademark Office*